US011371994B2

(12) United States Patent
Heath et al.

(10) Patent No.: US 11,371,994 B2
(45) Date of Patent: Jun. 28, 2022

(54) PHOSPHORYLATED AKT-SPECIFIC CAPTURE AGENTS, COMPOSITIONS, AND METHODS OF USING AND MAKING

(71) Applicant: California Institute of Technology, Pasadena, CA (US)

(72) Inventors: James R. Heath, Pasadena, CA (US); Arundhati Nag, Pasadena, CA (US); Samir Das, Pasadena, CA (US); Joseph O. Varghese, Pasadena, CA (US); Ryan K. Henning, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 14/485,243

(22) Filed: Sep. 12, 2014

(65) Prior Publication Data

US 2015/0219657 A1    Aug. 6, 2015

Related U.S. Application Data

(60) Provisional application No. 61/877,685, filed on Sep. 13, 2013.

(51) Int. Cl.
| | | |
|---|---|---|
| *C07K 7/06* | (2006.01) | |
| *C12Q 1/48* | (2006.01) | |
| *G01N 33/574* | (2006.01) | |
| *C07K 7/08* | (2006.01) | |
| *G01N 33/58* | (2006.01) | |

(52) U.S. Cl.
CPC .......... *G01N 33/5748* (2013.01); *C07K 7/06* (2013.01); *C07K 7/08* (2013.01); *C12Q 1/485* (2013.01); *G01N 33/574* (2013.01); *G01N 33/582* (2013.01); *G01N 2333/91205* (2013.01); *G01N 2440/14* (2013.01); *G01N 2800/52* (2013.01)

(58) Field of Classification Search
CPC ............ G01N 33/5748; G01N 33/574; G01N 33/582; G01N 2800/52; G01N 2333/91205; G01N 2440/14; C07K 7/08; C07K 7/06; C12Q 1/485
See application file for complete search history.

(56) References Cited

U.S. PATENT DOCUMENTS

| | | | |
|---|---|---|---|
| 6,566,088 B1 * | 5/2003 | McKnight | C12Q 1/34 435/18 |
| 9,239,332 B2 * | 1/2016 | Heath | A61K 49/0043 |

(Continued)

FOREIGN PATENT DOCUMENTS

| | | |
|---|---|---|
| WO | WO2011057347 | 5/2011 |
| WO | WO2012106671 | 8/2012 |
| WO | WO2013009869 | 1/2013 |

OTHER PUBLICATIONS

Schweinsberg et al., Bioconjugate Chem., 2008, vol. 19, pp. 2432-2439, published Nov. 19, 2008.*

(Continued)

*Primary Examiner* — Tracy Vivlemore
*Assistant Examiner* — Nam P Nguyen
(74) *Attorney, Agent, or Firm* — Pabst Patent Group LLP

(57) ABSTRACT

The present application provides stable peptide-based Akt capture agents and methods of use as detection and diagnosis agents and in the treatment of diseases and disorders. The application further provides methods of manufacturing Akt capture agents using iterative on-bead in situ click chemistry.

55 Claims, 69 Drawing Sheets

Specification includes a Sequence Listing.

(56) References Cited

U.S. PATENT DOCUMENTS

| | | | | |
|---|---|---|---|---|
| 2010/0009896 A1* | 1/2010 | Agnew | ............... | G01N 33/531 |
| | | | | 514/1.1 |
| 2015/0099658 A1* | 4/2015 | Pfeilsticker | .............. | C07K 7/08 |
| | | | | 506/9 |
| 2015/0344523 A1* | 12/2015 | Deyle | ................. | C07K 14/001 |
| | | | | 514/19.3 |

OTHER PUBLICATIONS

Pi-Han et al., Journal of Virology, vol. 85, No. 17, pp. 9114-9126, published Jun. 22, 2011.*
Chauhan et al. "The Taming of the Cell Penetrating Domain of the HIV Tat: Myths and Realities", J. Control Release, vol. 117, No. 2 , pp. 148-162, published Feb. 12, 2007.*
Nag et al., Angew. Chem. Int. Ed. Engl. Dec. 23, 2013; 52(52): 13975-13979.
TANG et al., Asian Journal of Andrology (2009) 11: 119-126.
Millward et al. J. Am. Chem. Soc. 2011, 133, 18280-18288.
International Search Report and Written Opinion dated Feb. 6, 2015, International Application No. PCT/US2014/055451.

* cited by examiner

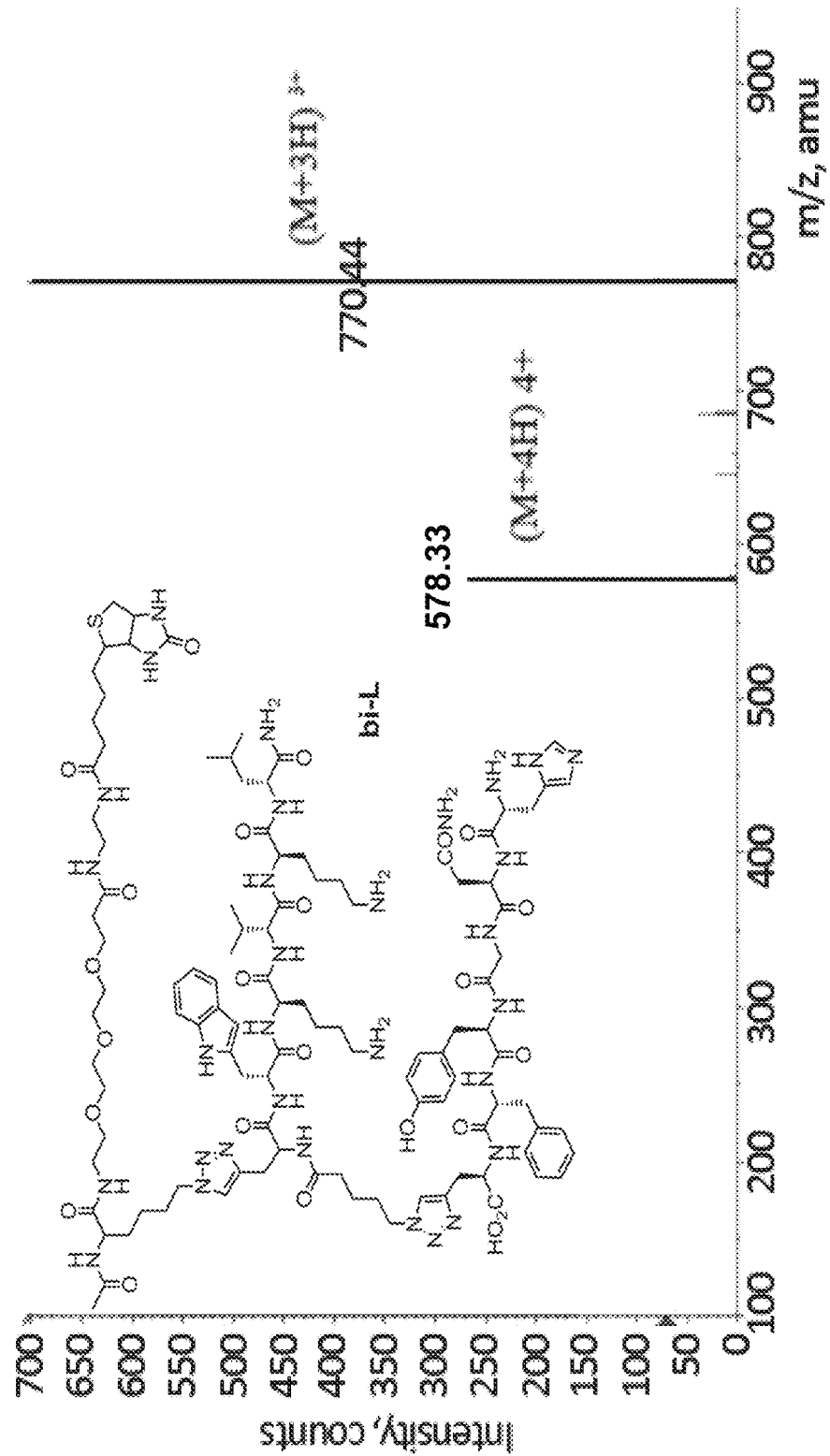

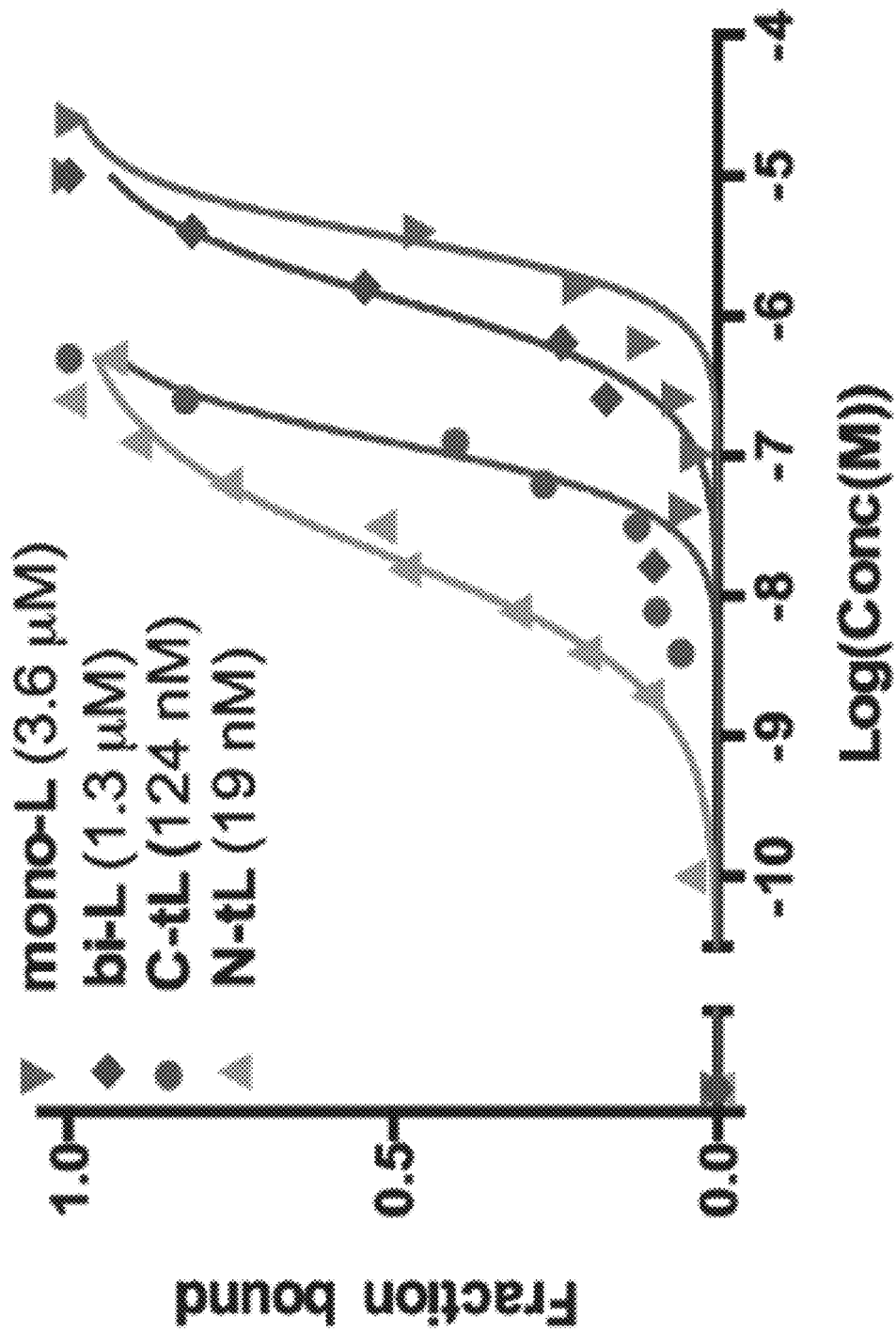

FIG. 23D

Akt2  ITPPDRYDSLGLLELDQRTH
      FPQF(pS)YSASIRE

Akt1  ITPPDQDDSMECVDSERRPH
      FPQF(pS)YSASGTA

Akt3  PEKYDEDGMDCMDNERRPH
      FPQF(pS)YSASGRE

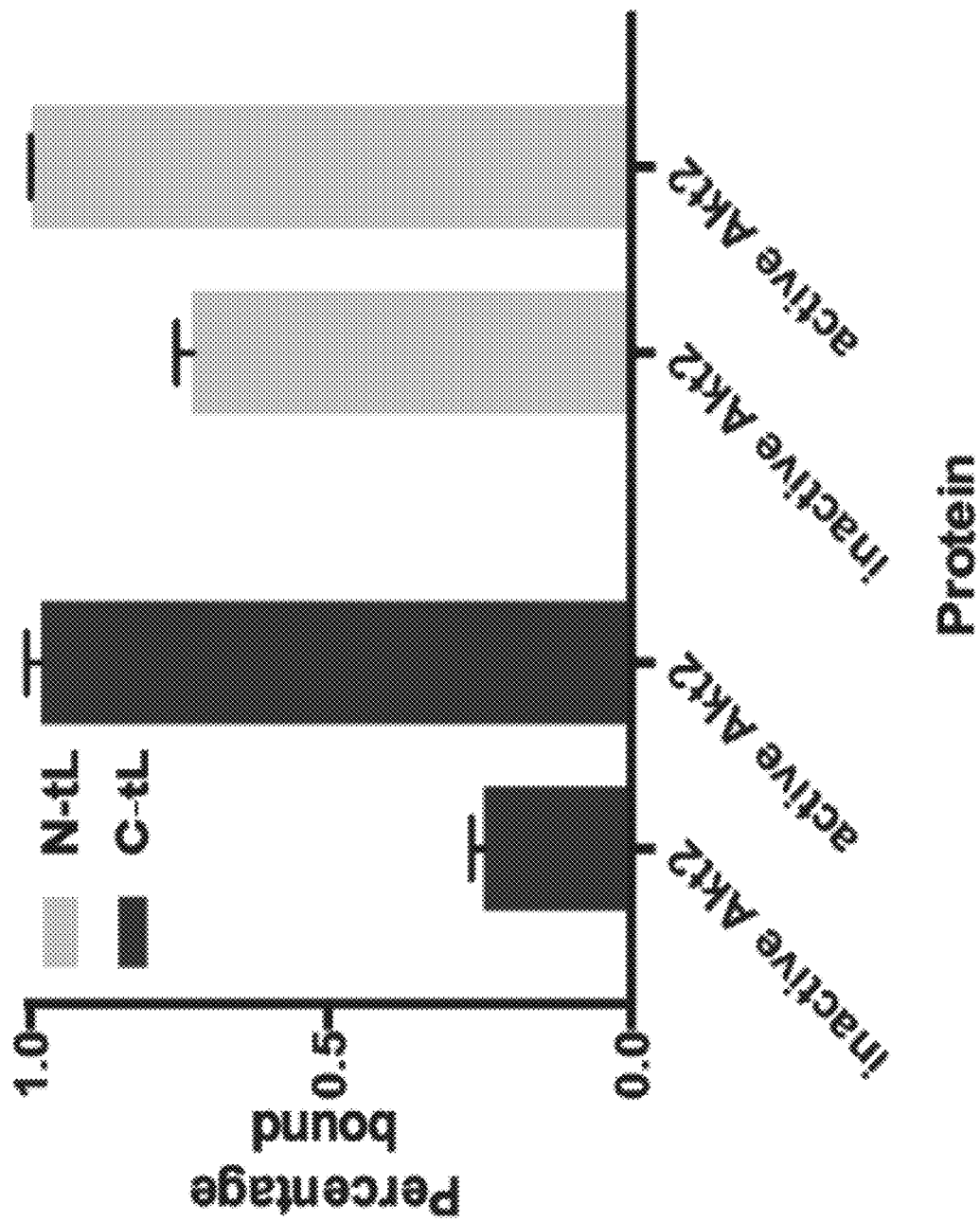

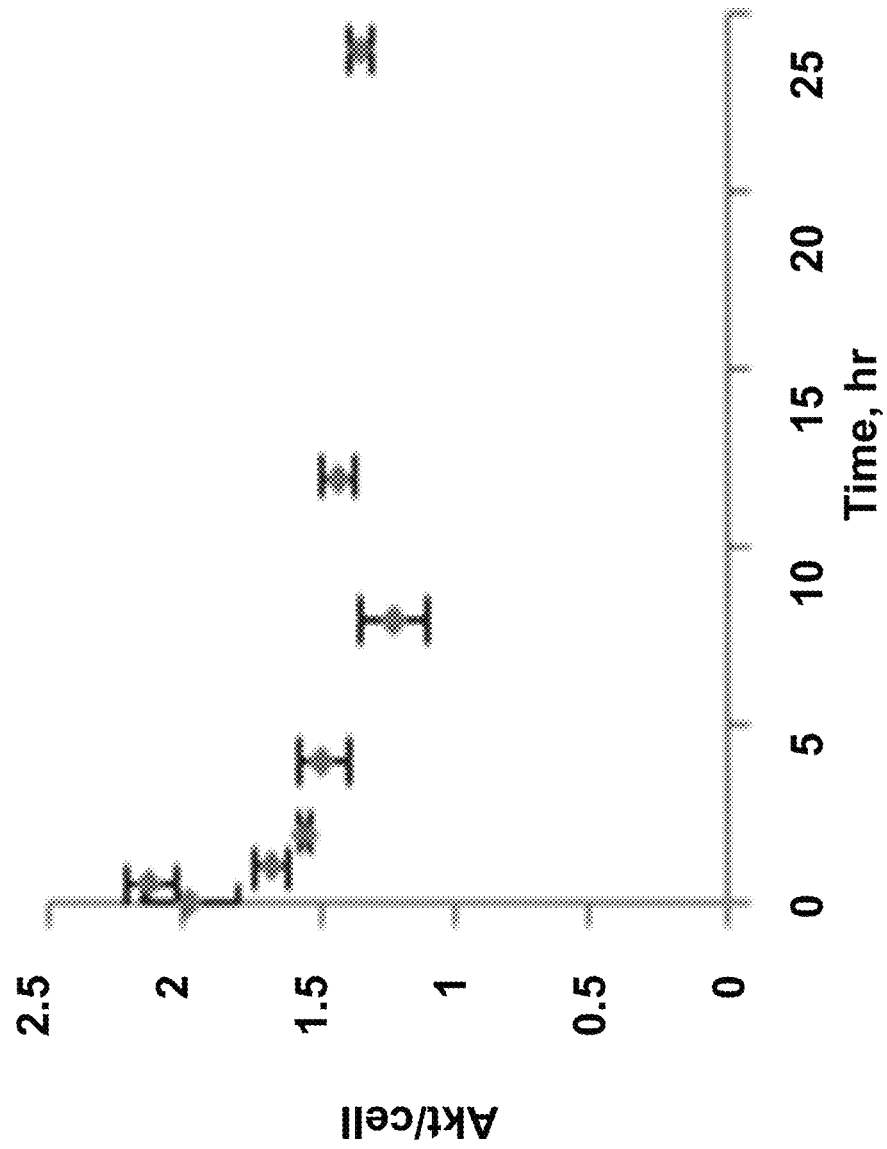

FIG. 37

P31749 - AKT1_HUMAN (SEQ ID NO: 87)
>sp|P31749|AKT1_HUMAN RAC-alpha serine/threonine-protein kinase
OS=Homo sapiens
GN=AKT1
PE=1
SV=2
MSDVAIVKEGWLHKRGEYIKTWRPRYFLLKNDGTFIGYKERPQDVDQREAPLNNFS
VAQCQLMKTERPRPNTFIIRCLQWTTVIERTFHVETPEEREEWTTAIQTVADGLKKQE
EEEMDFRSGSPSDNSGAEEMEVSLAKPKHRVTMNEFEYLKLLGKGTFGKVILVKEK
ATGRYYAMKILKKEVIVAKDEVAHTLTENRVLQNSRHPFLTALKYSFQTHDRLCFVME
YANGGELFFHLSRERVFSEDRARFYGAEIVSALDYLHSEKNVVYRDLKLENLMLDKD
GHIKITDFGLCKEGIKDGATMKTFCGTPEYLAPEVLEDNDYGRAVDWWGLGVVMYE
MMCGRLPFYNQDHEKLFELILMEEIRFPRTLGPEAKSLLSGLLKKDPKQRLGGGSED
AKEIMQHRFFAGIVWQHVYEKKLSPPFKPQVTSETDTRYFDEEFTAQMIT*ITPPDQDD*
*SMECVDSERRPHFPQFSYSASGTA*

FIG. 38

P31751 - AKT2_HUMAN (SEQ ID NO: 88)
>sp|P31751|AKT2_HUMAN RAC-beta serine/threonine-protein kinase
OS=Homo sapiens
GN=AKT2
PE=1 SV=2
MNEVSVIKEGWLHKRGEYIKTWRPRYFLLKSDGSFIGYKERPEAPDQTL
PPLNNFSVAECQLMKTERPRPNTFVIRCLQWTTVIERTFHVDSPDEREE
WMRAIQMVANSLKQRAPGEDPMDYKCGSPSDSSTTEEMEVAVSKARA
KVTMNDFDYLKLLGKGTFGKVILVREKATGRYYAMKILRKEVIIAKDEVAH
TVTESRVLQNTRHPFLTALKYAFQTHDRLCFVMEYANGGELFFHLSRER
VFTEERARFYGAEIVSALEYLHSRDVVYRDIKLENLMLDKDGHIKITDFGL
CKEGISDGATMKTFCGTPEYLAPEVLEDNDYGRAVDWWGLGVVMYEM
MCGRLPFYNQDHERLFELILMEEIRFPRTLSPEAKSLLAGLLKKDPKQRL
GGGPSDAKEVMEHRFFLSINWQDVVQKKLLPPFKPQVTSEVDTRYFDD
EFTAQSIT*ITPPDRYDSLGLLELDQRTHFPQFSYSASIRE*

FIG. 39

Q9Y243-1 - AKT3_HUMAN (SEQ ID NO: 89)
>sp|Q9Y243|AKT3_HUMAN RAC-gamma serine/threonine-protein kinase
OS=Homo sapiens
GN=AKT3
PE=1
SV=1

MSDVTIVKEGWVQKRGEYIKNWRPRYFLLKTDGSFIGYKEKPQDVDLPYP
LNNFSVAKCQLMKTERPKPNTFIIRCLQWTTVIERTFHVDTPEEREEWTEAI
QAVADRLQRQEEERMNCSPTSQIDNIGEEEMDASTTHHKRKTMNDFDYL
KLLGKGTFGKVILVREKASGKYYAMKILKKEVIIAKDEVAHTLTESRVLKNTR
HPFLTSLKYSFQTKDRLCFVMEYVNGGELFFHLSRERVFSEDRTRFYGAEI
VSALDYLHSGKIVYRDLKLENLMLDKDGHIKITDFGLCKEGITDAATMKTFC
GTPEYLAPEVLEDNDYGRAVDWWGLGVVMYEMMCGRLPFYNQDHEKLF
ELILMEDIKFPRTLSSDAKSLLSGLLIKDPNKRLGGGPDDAKEIMRHSFFSG
VNWQDVYDKKLVPPFKPQVTSETDTRYFDEEFTAQTITITPPEKYDEDGM
DCMDNERRPHFPQFSYSASGRE

SEQUENCE LISTING

```
<160> NUMBER OF SEQ ID NOS: 89

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(4)
```

```
<223> OTHER INFORMATION: D-amino acid

<400> SEQUENCE: 1

Trp Lys Val Lys
1

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: D-amino acid

<400> SEQUENCE: 2

Trp Lys Val Lys Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 3

Xaa Trp Lys Val Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 4

Xaa Trp Lys Val Lys Leu
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
```

```
<222> LOCATION: (4)..(5)
<223> OTHER INFORMATION: Xaa is independently selected from non-natural
      (D) steroisomers of the 20 natural amino acids excluding cysteine
      and methionine

<400> SEQUENCE: 5

His Asn Gly Xaa Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid

<400> SEQUENCE: 6

His Asn Gly Tyr Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(5)
<223> OTHER INFORMATION: D-amino acid

<400> SEQUENCE: 7

His Asn Gly Tyr Phe
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(5)
<223> OTHER INFORMATION: D-amino acid

<400> SEQUENCE: 8

His Asn Gly Arg Glu
1               5

<210> SEQ ID NO 9
<211> LENGTH: 5
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(5)
<223> OTHER INFORMATION: D-amino acid

<400> SEQUENCE: 9

His Asn Gly Ala Ile
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(5)
<223> OTHER INFORMATION: Xaa is independently selected from non-natural
      (D) steroisomers of the 20 natural amino acids excluding cysteine
      and methionine

<400> SEQUENCE: 10

His Asp Gly Xaa Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: D-amino acid

<400> SEQUENCE: 11

Tyr Tyr Arg Phe Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(5)
<223> OTHER INFORMATION: D-amino acid

<400> SEQUENCE: 12

Ser Ser Gly Arg Tyr
1               5

<210> SEQ ID NO 13
<211> LENGTH: 6
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 13

Xaa Tyr Tyr Arg Phe Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (5)..(6)
<223> OTHER INFORMATION: D-amino acid

<400> SEQUENCE: 14

Xaa Ser Ser Gly Arg Tyr
1               5

<210> SEQ ID NO 15
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (25)..(25)
<223> OTHER INFORMATION: PHOSPHORYLATION

<400> SEQUENCE: 15

Ile Thr Pro Pro Asp Arg Tyr Asp Ser Leu Gly Leu Leu Glu Leu Asp
1               5                   10                  15

Gln Arg Thr His Phe Pro Gln Phe Ser Tyr Ser Ala Ser Ile Arg Glu
            20                  25                  30

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (14)..(14)
<223> OTHER INFORMATION: AMIDATION

<400> SEQUENCE: 16

Gly Arg Lys Lys Arg Arg Gln Arg Arg Arg Pro Pro Gln Gln
1               5                   10
```

```
<210> SEQ ID NO 17
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: PEG2-phospho-Akt2

<400> SEQUENCE: 17

His His His His His His
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: PEG2-phospho-Akt1

<400> SEQUENCE: 18

His His His His His His
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: PEG2-phospho-Akt3

<400> SEQUENCE: 19

His His His His His His
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Xaa is independently selected from non-natural
      (D) steroisomers of the 20 natural amino acids excluding cysteine
      and methionine
<220> FEATURE:
<221> NAME/KEY: MISC_FEATURE
<222> LOCATION: (6)..(6)
<223> OTHER INFORMATION: D-propargylglycine

<400> SEQUENCE: 20

Xaa Xaa Xaa Xaa Xaa Xaa
1               5

<210> SEQ ID NO 21
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 21

His Asn Gly Tyr Phe Xaa
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 22

His Asn Gly Tyr Gly Xaa
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 23

His Asn Gly Arg Glu Xaa
1               5

<210> SEQ ID NO 24
<211> LENGTH: 6
<212> TYPE: PRT
```

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 24

His Asn Gly Ala Ile Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid

<400> SEQUENCE: 25

Xaa His Asp Gly Gly Phe
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: PHOSPHORYLATION

<400> SEQUENCE: 26

His Phe Pro Gln Phe Ser Tyr Ser Ala Ser Ile Arg Glu
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Ala Leu Ala Pro Tyr Ile Pro
1               5

<210> SEQ ID NO 28
<211> LENGTH: 6

```
<212> TYPE: PRT
<213> ORGANISM: Artificial Sequence
<220> FEATURE:
<223> OTHER INFORMATION: Synthetic peptide

<400> SEQUENCE: 28

His His His His His His
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: D-amino acid
<220> FEATURE:
<221> NAME/KEY: MISC_FEATURE
<222> LOCATION: (5)..(5)
<223> OTHER INFORMATION: allyloxycarbonyl

<400> SEQUENCE: 29

Trp Lys Val Lys Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 30

Xaa Tyr Tyr Arg Phe Gly
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(3)
<223> OTHER INFORMATION: D-amino acid
```

```
<220> FEATURE:
<221> NAME/KEY: MISC_FEATURE
<222> LOCATION: (6)..(6)
<223> OTHER INFORMATION: D-amino acid

<400> SEQUENCE: 31

Xaa His Asp Gly Gly Phe
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (7)..(7)
<223> OTHER INFORMATION: 10% D-methionine
<220> FEATURE:
<221> NAME/KEY: MISC_FEATURE
<222> LOCATION: (7)..(7)
<223> OTHER INFORMATION: polyethylene glycol-grafted polystyrene beads

<400> SEQUENCE: 32

Xaa Xaa Xaa Xaa Xaa Xaa Xaa
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine
<220> FEATURE:
<221> NAME/KEY: MISC_FEATURE
<222> LOCATION: (7)..(7)
<223> OTHER INFORMATION: 10% D-methionine
<220> FEATURE:
<221> NAME/KEY: MISC_FEATURE
<222> LOCATION: (7)..(7)
<223> OTHER INFORMATION: polyethylene glycol-grafted polystyrene beads

<400> SEQUENCE: 33

Xaa Xaa Xaa Xaa Xaa Xaa Xaa
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
```

```
<220> FEATURE:
<221> NAME/KEY: MISC_FEATURE
<222> LOCATION: (2)..(6)
<223> OTHER INFORMATION: D-amino acid
<220> FEATURE:
<221> NAME/KEY: MISC_FEATURE
<222> LOCATION: (7)..(7)
<223> OTHER INFORMATION: 10% D-methionine
<220> FEATURE:
<221> NAME/KEY: MISC_FEATURE
<222> LOCATION: (7)..(7)
<223> OTHER INFORMATION: polyethylene glycol-grafted polystyrene beads

<400> SEQUENCE: 34

Xaa Xaa Xaa Xaa Xaa Xaa Xaa
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 35

His Asn Gly Ile Ile Xaa
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 36

His Asn Gly Gly Asp Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
```

```
<220> FEATURE:
<221> NAME/KEY: MISC_FEATURE
<222> LOCATION: (4)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 37

His Asn Gly Arg Glu Xaa
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 38

His Arg Tyr Tyr Gly Xaa
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 39

Val Asn Arg Arg Phe Xaa
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 40

Ala Tyr Pro His Phe Xaa
```

```
<210> SEQ ID NO 41
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 41

Gly Phe Arg Arg Phe Xaa
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 42

Arg Gly Phe Phe Leu Xaa
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 43

Val Tyr Tyr Arg His Xaa
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
```

```
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 44

Phe His Tyr Tyr Tyr Xaa
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 45

Phe Tyr His Lys His Xaa
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 46

Pro Phe Gln His Phe Xaa
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 47

Ser His Phe Tyr Thr Xaa
1               5

<210> SEQ ID NO 48
<211> LENGTH: 6
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 48

Val His Gly Ala Ala Xaa
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (6)..(6)
<223> OTHER INFORMATION: propargylglycine

<400> SEQUENCE: 49

Tyr His Gln Tyr Gly Xaa
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (2)..(2)
<223> OTHER INFORMATION: Xaa is selected from lysine or leucine

<400> SEQUENCE: 50

Xaa Xaa Phe Gln Phe Arg
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (3)..(3)
<223> OTHER INFORMATION: Xaa is selected from aspartic acid or
      asparigine

<400> SEQUENCE: 51

Xaa Arg Xaa Arg Phe Arg
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 52

Xaa Tyr Val Tyr Arg Phe
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 53

Xaa Ser Phe Arg Arg Phe
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 54

Xaa Ser Val Arg Phe Arg
1               5
```

```
<210> SEQ ID NO 55
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (3)..(3)
<223> OTHER INFORMATION: Xaa is selected from lysine or leucine

<400> SEQUENCE: 55

Xaa Ile Xaa Arg Arg Ala
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (3)..(3)
<223> OTHER INFORMATION: Xaa is selected from glutamin or threonine
<220> FEATURE:
<221> NAME/KEY: MISC_FEATURE
<222> LOCATION: (4)..(4)
<223> OTHER INFORMATION: Xaa is selected from lysine or leucine

<400> SEQUENCE: 56

Xaa Arg Xaa Xaa Trp Arg
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (3)..(3)
<223> OTHER INFORMATION: Xaa is selected from glutamine or threonine

<400> SEQUENCE: 57

Xaa Arg Xaa Ser Arg Arg
1               5
```

```
<210> SEQ ID NO 58
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 58

Xaa Arg Arg Ile Tyr Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine
<220> FEATURE:
<221> NAME/KEY: MISC_FEATURE
<222> LOCATION: (5)..(6)
<223> OTHER INFORMATION: D-amino acid
<220> FEATURE:
<221> NAME/KEY: MISC_FEATURE
<222> LOCATION: (6)..(6)
<223> OTHER INFORMATION: Xaa is selected from glutamine or threonine

<400> SEQUENCE: 59

Xaa Arg Phe Gly Arg Xaa
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 60

Xaa Lys Phe Gln Phe Arg
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 61

Xaa Leu Phe Gln Phe Arg
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 62

Xaa Lys Phe Thr Phe Arg
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 63

Xaa Leu Phe Thr Phe Arg
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 64

Xaa Arg Asp Arg Phe Arg
1               5

<210> SEQ ID NO 65
```

```
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: D-amino acid
<220> FEATURE:
<221> NAME/KEY: MISC_FEATURE
<222> LOCATION: (1)..(1)
<223> OTHER INFORMATION: propargylglycine

<400> SEQUENCE: 65

Xaa Arg Asn Arg Phe Arg
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 66

Xaa His Asp Gly Ser Gln
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 67

Xaa His Asp Gly Trp Trp
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 68

Xaa His Asp Gly Ile Val
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 69

Xaa His Asp Gly Asp Trp
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid

<400> SEQUENCE: 70

Xaa His Asp Gly Gly
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
```

<223> OTHER INFORMATION: D-amino acid

<400> SEQUENCE: 71

Xaa His Asp Gly Asp Arg
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid

<400> SEQUENCE: 72

Xaa His Asp Gly Gly Phe
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid

<400> SEQUENCE: 73

Xaa His Asp Gly Gly Glu
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 74

Xaa His Asp Gly Ser Phe
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 75

Xaa His Asp Gly Gln Lys
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 76

Xaa His Asp Gly Ser Ala
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 77

Xaa His Asp Gly Lys Phe
1               5

```
<210> SEQ ID NO 78
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: azidolysine
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(6)
<223> OTHER INFORMATION: D-amino acid

<400> SEQUENCE: 78

Xaa His Asp Gly Ala Val
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid

<400> SEQUENCE: 79

His Asp Gly Gly Phe
1               5

<210> SEQ ID NO 80
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: H2N-Peg5-Lys(Dde)-Peg5-
<220> FEATURE:
<221> NAME/KEY: MOD_RES
<222> LOCATION: (14)..(14)
<223> OTHER INFORMATION: AMIDATION

<400> SEQUENCE: 80

Gly Arg Lys Lys Arg Arg Gln Arg Arg Arg Pro Pro Gln Gln
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 6-aminohexanoic acid

<400> SEQUENCE: 81
```

```
Ala Leu Ala Pro Tyr Ile Pro
1               5
```

<210> SEQ ID NO 82
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: H2N-HHHHHH-(PEG)2-
<220> FEATURE:
<221> NAME/KEY: MOD_RES
<222> LOCATION: (25)..(25)
<223> OTHER INFORMATION: PHOSPHORYLATION
<220> FEATURE:
<221> NAME/KEY: MOD_RES
<222> LOCATION: (32)..(32)
<223> OTHER INFORMATION: AMIDATION

<400> SEQUENCE: 82

```
Ile Thr Pro Pro Asp Arg Tyr Asp Ser Leu Gly Leu Leu Glu Leu Asp
1               5                   10                  15
Gln Arg Thr His Phe Pro Gln Phe Ser Tyr Ser Ala Ser Ile Arg Glu
            20                  25                  30
```

<210> SEQ ID NO 83
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: HHHHHH-(PEG)2-
<220> FEATURE:
<221> NAME/KEY: MOD_RES
<222> LOCATION: (24)..(24)
<223> OTHER INFORMATION: PHOSPHORYLATION

<400> SEQUENCE: 83

```
Ile Thr Pro Pro Asp Gln Asp Asp Ser Met Glu Cys Val Asp Ser Glu
1               5                   10                  15
Arg Arg His Phe Pro Gln Phe Ser Tyr Ser Ala Ser Gly Thr Ala
            20                  25                  30
```

<210> SEQ ID NO 84
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: HHHHHH-(PEG)2-
<220> FEATURE:
<221> NAME/KEY: MOD_RES
<222> LOCATION: (24)..(24)
<223> OTHER INFORMATION: PHOSPHORYLATION

<400> SEQUENCE: 84

```
Pro Glu Lys Tyr Asp Glu Asp Gly Met Asp Cys Met Asp Asn Glu Arg
1               5                   10                  15
Arg Pro His Phe Pro Gln Phe Ser Tyr Ser Ala Ser Gly Arg Glu
            20                  25                  30
```

-continued

```
<210> SEQ ID NO 85
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (25)..(25)
<223> OTHER INFORMATION: PHOSPHORYLATION

<400> SEQUENCE: 85

Ile Thr Pro Pro Asp Gln Asp Asp Ser Met Glu Cys Val Asp Ser Glu
1               5                   10                  15

Arg Arg Pro His Phe Pro Gln Phe Ser Tyr Ser Ala Ser Gly Thr Ala
                20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (24)..(24)
<223> OTHER INFORMATION: PHOSPHORYLATION

<400> SEQUENCE: 86

Pro Glu Lys Tyr Asp Glu Asp Gly Met Asp Cys Met Asp Asn Glu Arg
1               5                   10                  15

Arg Pro His Phe Pro Gln Phe Ser Tyr Ser Ala Ser Gly Arg Glu
                20                  25                  30

<210> SEQ ID NO 87
<211> LENGTH: 480
<212> TYPE: PRT
<213> ORGANISM: Homo sapiens

<400> SEQUENCE: 87

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
            35                  40                  45

Glu Ala Pro Leu Asn Asn Phe Ser Val Ala Gln Cys Gln Leu Met Lys
        50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
                100                 105                 110

Gln Glu Glu Glu Glu Met Asp Phe Arg Ser Gly Ser Pro Ser Asp Asn
            115                 120                 125

Ser Gly Ala Glu Glu Met Glu Val Ser Leu Ala Lys Pro Lys His Arg
        130                 135                 140

Val Thr Met Asn Glu Phe Glu Tyr Leu Lys Leu Leu Gly Lys Gly Thr
145                 150                 155                 160
```

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480

<210> SEQ ID NO 88
<211> LENGTH: 481
<212> TYPE: PRT
<213> ORGANISM: Homo sapiens

<400> SEQUENCE: 88

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

```
Thr Glu Arg Pro Arg Pro Asn Thr Phe Val Ile Arg Cys Leu Gln Trp
 65                  70                  75                  80

Thr Thr Val Ile Glu Arg Thr Phe His Val Asp Ser Pro Asp Glu Arg
                 85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Met Glu Val Ala Val Ser Lys Ala Arg
130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
            195                 200                 205

His Pro Phe Leu Thr Ala Leu Lys Tyr Ala Phe Gln Thr His Asp Arg
210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
450                 455                 460

Asp Gln Arg Thr His Phe Pro Gln Phe Ser Tyr Ser Ala Ser Ile Arg
465                 470                 475                 480
```

-continued

Glu

<210> SEQ ID NO 89
<211> LENGTH: 479
<212> TYPE: PRT
<213> ORGANISM: Homo sapiens

<400> SEQUENCE: 89

```
Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
                20                  25                  30

Gly Ser Phe Ile Gly Tyr Lys Glu Lys Pro Gln Asp Val Asp Leu Pro
            35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
290                 295                 300
```

```
Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
            325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
            355                 360                 365

Leu Ser Ser Asp Ala Lys Ser Leu Leu Ser Gly Leu Leu Ile Lys Asp
    370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
            405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
            435                 440                 445

Pro Glu Lys Tyr Asp Glu Asp Gly Met Asp Cys Met Asp Asn Glu Arg
    450                 455                 460

Arg Pro His Phe Pro Gln Phe Ser Tyr Ser Ala Ser Gly Arg Glu
465                 470                 475
```

PHOSPHORYLATED AKT-SPECIFIC CAPTURE AGENTS, COMPOSITIONS, AND METHODS OF USING AND MAKING

RELATED APPLICATIONS

This application claims priority from U.S. Provisional Patent Application No. 61/877,685, filed on Sep. 13, 2013 and incorporated herein by reference in its entirety.

GOVERNMENT SUPPORT

This invention was made with government support Grant No. CA119347 awarded by the National Institutes of Health and Grant No. W911 NF-09-D-001 awarded by the U.S. Amy. The government has certain rights in the invention.

BACKGROUND

Overexpression and/or hyperactivation of Akt is associated with many cancers, making Akt an important target for the development of drugs and diagnostics. Overexpression and/or activation of Akt can increase resistance of tumors to chemo or radio therapies. The importance of Akt2 as a therapeutic target has prompted development of both ATP competitive and allosteric inhibitors. The allosteric inhibitors bind to the interface between the membrane docking pleckstrin homology domain (PHD) and the kinase domain.

In cancer cell lines and tissue samples, constitutively active Akt2 is phosphorylated at Ser474. Ser474 in the Akt2 protein (Ser473 in Akt1) is located in the hydrophobic motif (HM) of the C-terminal tail, and is phosphorylated by the Rictor-mTOR. The phosphorylated HM allosterically activates Akt2 by binding to a hydrophobic groove in the N-lobe of Akt2 and enhancing the kinase activity 10-fold. In the PKB crystal structure, the electron density for residues 442-481 is not resolved, suggesting a disordered C-terminus. Evidence suggests that this unstructured epitope lacks a binding pocket, and thus, may not be targetable by traditional small molecule inhibitors.

SUMMARY

The present disclosure relates to chemically synthesized capture agents (called protein-catalyzed capture agents, or PCC Agents) that are designed to bind Akt, methods for making said capture agents using iterative in situ click chemistry, methods for using said capture agents to detect Akt, and assays employing said methods. The performance of such an assay is compared to the gold standard anti-Akt immunoassay, plus controls.

In one aspect, provided herein is a stable, synthetic capture agent that specifically binds to phosphorylated Akt, wherein the capture agent comprises a designed anchor ligand, a designed secondary ligand, a designed tertiary ligand, and optionally a designed quarternary ligand, and wherein the ligands selectively bind Akt2. In one embodiment, the ligands specifically bind Akt2. In another embodiment, the capture agent binds to residues 450-481 of phosphorylated Akt2. In another embodiment, the binding of the capture agent to phosphorylated Akt2 indicates the presence of cancer. In one embodiment, the ligands specifically bind Akt1. In another embodiment, the capture agent binds to residues 449-480 of phosphorylated Akt1. In another embodiment, the binding of the capture agent to phosphorylated Akt1 indicates the presence of cancer.

In another aspect, provided herein is a composition comprising one or more synthetic capture agents of the invention that specifically binds Akt2.

In another aspect, provided herein is a method for detecting Akt2 in a biological sample, comprising the step of treating the biological sample with one or more capture agents of the invention.

In another aspect, provided herein is method of diagnosing cancer in a subject, the method comprising the steps of: a) administering to the subject one or more capture agents of the invention, wherein each capture agent is linked to a detectable moiety; and b) detecting the moiety linked to each capture agent; wherein detection of the moiety diagnoses cancer in the subject.

Anchor Ligand

The anchor ligand was selected via an in situ click screen from a large (e.g., $10^6$ element) one-bead-one-compound (OBOC) peptide library. In one embodiment, the peptide library is Library A (see Table 1). In one embodiment of the capture agent, the anchor ligand comprises the sequence wkvk (SEQ ID NO:1). In another embodiment of the capture agent, the anchor ligand comprises the sequence wkvkl (SEQ ID NO:2). In another embodiment, the anchor ligand comprises the sequence (D-Pra)-wkvk (SEQ ID NO:3). In another embodiment, the anchor ligand comprises the sequence (D-Pra)-wkvkl (SEQ ID NO:4). In some embodiments, the anchor ligand is chemically modified to comprise a detection label (e.g., biotin, biotin-PEG, DOTA, NOTA and the like).

Secondary Ligand

Secondary ligands were selected via an in situ click screen from a large (e.g., $10^6$ element) one-bead-one-compound (OBOC) peptide library. In one embodiment, the peptide library is Library B (see Table 1). In some embodiments, the secondary ligand consists of 5 amino acids. In one embodiment, the peptide library is comprehensive for 5-mers, with a 6th amino acid at the N-terminus presenting azide functionality. In one embodiment, the library comprises non-natural (D) stereoisomers of the 20 natural amino acids, excluding cysteine and methionine. In one embodiment, the secondary ligand comprises the sequence hnGxx (SEQ ID NO:5), wherein each x is independently selected from non-natural (D) stereoisomers of the 20 natural amino acids, excluding cysteine and methionine. In some embodiments, the secondary ligand comprises a sequence selected from the sequences of Tables 2 and 3. In a particular embodiment, the secondary ligand comprises a sequence selected from the group consisting of hnGyG (SEQ ID NO:6), hnGyf (SEQ ID NO:7), hnGre (SEQ ID NO:8) and hnGai (SEQ ID NO:9). In a particular embodiment, the secondary ligand comprises the sequence hnGyf (SEQ ID NO:7).

Tertiary Ligand

Tertiary ligands were selected via an in situ click screen from a large (e.g., $10^6$ element) one-bead-one-compound (OBOC) peptide library. In one embodiment, the tertiary ligand clicks to the N-terminus of a biligand. In another embodiment, the tertiary ligand clicks to the C-terminus of a biligand. In certain embodiments, the peptide library is Library A or Library C (see Table 1). In one embodiment, the tertiary ligand comprises a sequence selected from the sequences of Table 4 and Table 6.

In one embodiment, the tertiary ligand clicks to the C-terminus of a biligand and comprises the sequence hdGxx (SEQ ID NO:10), wherein each x is independently selected from non-natural (D) stereoisomers of the 20 natural amino acids, excluding cysteine and methionine.

In another embodiment, the tertiary ligand clicks to the N-terminus of a biligand and comprises a sequence selected from yyrfG (SEQ ID NO:11) and ssGry (SEQ ID NO:12). In another embodiment, the tertiary ligand clicks to the N-terminus of a biligand and comprises a sequence selected from (D-Pra)-yyrfG (SEQ ID NO:13) and (D-Pra)-ssGry (SEQ ID NO:14).

Quaternary Ligand

The quaternary ligands, if present, are selected via an in situ click screen from a large (e.g., $10^6$ element) one-bead-one-compound (OBOC) peptide library.

Triazole Linkage

In one embodiment of the capture agent, the anchor ligand and secondary ligand are linked together via a 1,4-substituted-1,2,3-triazole residue (Tz4). In another embodiment, the secondary ligand and the tertiary ligand are linked together via a 1,4-substituted-1,2,3-triazole residue (Tz4). In yet another embodiment, the tertiary ligand and the quarternary ligand are linked together via a 1,4-substituted-1,2,3-triazole residue (Tz4). In yet another embodiment, the anchor ligand and secondary ligand are linked together via a 1,4-substituted-1,2,3-triazole residue, and the secondary ligand and the tertiary ligand are linked together via a 1,4-substituted-1,2,3-triazole residue. In yet another embodiment, the anchor ligand and secondary ligand are linked together via a 1,4-substituted-1,2,3-triazole residue, the secondary ligand and the tertiary ligand are linked together via a 1,4-substituted-1,2,3-triazole residue and the tertiary ligand and the quarternary ligand are linked together via a 1,4-substituted-1,2,3-triazole residue.

Protein Target (Phospho-Akt2-Peptide)

The anchor ligand and higher-order ligand candidates were screened against a chemically-modified peptide comprising of the sequence of the target epitope, i.e., the 32 amino acid long C-terminal fragment of Akt2 (amino acids 450-481) that contains a phosphorylated serine 474 residue (pS474). In certain embodiments, the protein target comprises an amino acid sequence that is 80 to 100% identical to residues ITPPDRYDSLGLLELDQRTHFPQF(pS)YSASIRE (SEQ ID NO:15).

In one embodiment, the protein target comprises a dinuclear Zn (II) dipicolylamine (DPA) complex ("complex"). In one embodiment, the complex comprises an azide group as an in situ click anchor site and a biotin group as an assay handle.

Bilagands, Triligands and Tetraligands

In one embodiment, a capture agent of the invention is a biligand, comprising an anchor ligand and a secondary ligand. Non-limiting examples of biligand capture agents of the invention are disclosed in FIG. 18C-E.

In another embodiment, a capture agent of the invention is a triligand, comprising an anchor ligand, a secondary ligand and a tertiary ligand. Non-limiting examples of triligand capture agents of the invention are disclosed in FIGS. 22 and 28-33.

In still another embodiment, a capture agent of the invention is a tetraligand, comprising an anchor ligand, a secondary ligand, a tertiary ligand and a quaternary ligand.

In one embodiment, the capture agent binds to Akt2. In another embodiment, the capture agent binds to phosphorylated Akt2.

Properties

In certain embodiments, the Akt2 capture agents provided herein are stable across a wide range of temperatures, pH's, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Detectable Labels

In some embodiments, the capture agent is labeled with a label selected from the group consisting of biotin, copper-DOTA, biotin-PEG3, aminooxyacetate, $^{19}$FB, $^{18}$FB, FITC-PEG3, fluorescein and fluorescein derivatives (e.g., 5-carboxy fluorescein). In other embodiments, the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the label is a fluorescent label. In a particular embodiment, the detectable label is $^{18}$F.

Cell Penetrating Peptides

In some embodiments, the capture agent comprises a cell penetrating peptide. These cell penetrating peptides allow the capture agents to enter eukaryotic cells. In certain embodiments, these eukaryotic cells are mammalian cells. In specific embodiments, these mammalian cells are human cells. In certain embodiments, the cell penetrating peptide is an HIV-TAT sequence. In certain embodiments, the HIV-TAT sequence is a sequence at least 90% identical to $H_2N$-GRKKRRQRRRPPQQ-$CONH_2$ (SEQ ID NO:16) or a fragment thereof. Other cell penetrating peptides that can be used include penetratin, SynB1, SynB2, PTD-4, PTD-5, FHV Coar (35-49), BMV Gag (7-25), HTLV-II Rex (4-16), D-Tat, R9-Tat, transportan, MAP, SBP, FBP, MPG, Pep-1, Pep-2, polyarginines, or polylysines. Any sequence at least 90% identical to any of the cell penetrating peptides or fragments thereof may be used.

Methods and Uses

Provided herein is a method of inhibiting Akt2 signaling in a subject comprising administering to the subject a capture agent of the invention. In certain embodiments, methods are provided for inhibiting Akt2 activity in vivo or in vitro using a Akt2 capture agent as provided herein. In certain embodiments, inhibition of Akt2 activity results in an effective decrease in Akt2 levels and/or a change in Akt2 conformation.

Also provided herein is a method of treating a condition associated with increased Akt2 expression and/or activity in a subject in need thereof, comprising administering a therapeutically effective amount of a capture agent as described herein. In one embodiment, the condition associated with increased Akt2 expression and/or activity is cancer. In one embodiment, the cancer is ovarian cancer.

Provided is a method of diagnosing cancer in a subject, the method comprising the steps of:
a) administering one or more capture agents of the invention to the subject, wherein each capture agent is linked to a detectable moiety; and
b) detecting the moiety linked to each capture agent; wherein detection of the moiety diagnoses cancer in the subject.

Also provided is a method of detecting cancer in a subject, comprising the step of contacting a biological sample from the subject with one or more capture agents of the invention.

Also provided is a method of detecting cancer in a biological sample using an immunoassay, wherein the immunoassay utilizes a capture agent as described herein, and wherein said capture agent replaces an antibody or its equivalent in the immunoassay. In certain embodiments, methods are provided for identifying, detecting, quantifying, or separating Akt2 in a biological sample using the capture agents as described herein. In one embodiment of the method, the immunoassay is selected from the group of Western blot, pull-down assay, dot blot, and ELISA.

Also provided is a method of monitoring treatment of a subject receiving cancer-directed therapy comprising the steps of:
a) contacting a first biological sample from the subject with one or more capture agents of the invention, wherein each capture agent is linked to a detectable moiety;
b) detecting the moiety linked to the capture agent, wherein the capture agent is bound to Akt2;
c) administering a treatment for the cancer associated with increased Akt2 expression to the subject;
d) contacting a second biological sample from the subject one or more capture agents of the invention, wherein each capture agent is linked to a detectable moiety; and
e) detecting the moiety linked to the capture agent, wherein the capture agent is bound to Akt2; and
(f) comparing the level of moiety detected in step (b) with the level of moiety detected in step (d).

In one embodiment, if less of the moiety is detected in step (e) than in step (b), the treatment is improving cancer in the subject.

Also provided herein is a method of monitoring treatment of a subject receiving Akt2-directed therapy comprising administering to the patient a small-molecule positron-emission-tomography ligand (PET ligand) that is bound to the Akt2 capture agent, as described herein, on or near a Akt2-expressing cancer in the subject.

Also provided herein is the use of one or more Akt2 capture agents of the invention for use in preparing a medicament for treating a condition associated with increased Akt2 expression and/or activity in a subject in need thereof.

Kits

Provided herein in certain embodiments are kits comprising one or more capture agents of the invention. In certain embodiments, these kits may be used for identifying, detecting, quantifying, and/or separating Akt2, and in certain embodiments the kits may be used in the diagnosis and/or staging of a conditions associated with the presence of Akt2. In certain embodiments, a kit as provided herein comprises: (a) a substrate comprising an adsorbent thereon, wherein the adsorbent is suitable for binding Akt2, and (b) a washing solution or instructions for making a washing solution, wherein the combination of the adsorbent and the washing solution allows detection of Akt2. In other embodiments, the kits provided herein may be used in the treatment of a condition associated with the presence of Akt2.

In certain embodiments, a kit may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit as comprises: (a) one or more capture agents that specifically bind Akt2; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of Akt2 detected in a sample is an amount consistent with a diagnosis of a particular condition.

Synthesis of Capture Agents

Provided herein are methods for making (i.e., synthesizing) the Akt2 capture agents of the invention. In one embodiment, the method comprises the steps of:
(a) providing an anchor ligand;
(b) identifying a secondary ligand by the following steps:
  (i) preparing an anchor ligand selection block comprising the anchor ligand and an azido group or an alkynyl group;
  (ii) preparing a plurality of candidate peptides to select a secondary ligand for the target protein, the plurality of peptides comprising an azido group, or an alkynyl group, if the anchor ligand selection block comprises an alkynyl group, or an azido group, respectively;
  (iii) contacting the anchor ligand selection block and the plurality of peptides with the target protein (e.g., an epitope of Akt2);
  (iv) providing a capture agent biligand by forming a disubstituted 1,2,3-triazole linkage between the anchor ligand selection block and the secondary ligand wherein the azido group and alkynyl group of the anchor ligand selection block and the secondary ligand are brought in close proximity by binding to the target protein;
  (v) selecting the capture agent biligand that has an affinity with the target protein; and
  (vi) sequencing the secondary ligand; and optionally
(c) identifying a tertiary ligand by the following steps:
  (i) preparing a biligand selection block comprising an azido group or an alkynyl group; and
  (ii) repeating steps (b)(ii) to (b)(vi) using a third plurality, fourth plurality, etc., of candidate peptides until a capture agent having desired binding affinity to the target protein is obtained; and optionally
(d) identifying a quarternary ligand and, optionally, additional ligands by the following steps:
  (i) preparing a triligand selection block comprising an azido group or an alkynyl group; and
  (ii) repeating steps (c)(ii) to (c)(vi) using a fourth plurality, fifth plurality, etc., of candidate peptides until a capture agent having desired binding affinity to the target protein is obtained.

In one embodiment, step (a) comprises identifying an anchor ligand by the following steps:
(i) preparing a synthetic target polypeptide corresponding to an epitope of the target protein (e.g., Akt2);
(ii) preparing a first plurality of candidate peptides to screen against the target polypeptide;
(iii) contacting the target polypeptide with the first plurality of candidate peptides;
(iv) selecting a candidate peptide with affinity for the target polypeptide as the anchor ligand, wherein the candidate peptide binds to the target polypeptide; and
(v) sequencing the anchor ligand;

In one embodiment, step (a) comprises identifying an anchor ligand using an in situ click screen against a large one-bead-one-compound library (see, e.g., Library A of Table 1).

Also provided is a multiplex capture agent comprising two or more capture agents that bind specifically to two or more Akt2. In one embodiment, the multiplex capture agent comprises a designed anchor ligand, a designed secondary ligand, optionally, a designed tertiary ligand and optionally, a designed quarternary ligand.

The disclosure also provides a method of diagnosing a disease comprising a) administering to the subject the multiplex capture agent of described above linked to a detectable moiety; and b) detecting the moiety linked to the multiplex capture agent in the subject; wherein detection of the moiety diagnoses a disease in the subject.

In either of these methods, the disease can be a disease associated with increased expression or activation of Akt2. In certain embodiments, the disease is cancer.

Also provided is a method of diagnosing a disease associated with increased expression or activation of Akt2, comprising the steps of:
a) administering to the subject a multiplex capture agent of described herein, wherein the multiplex capture agent is linked to a detectable moiety; and
b) detecting the moiety linked to the multiplex capture agent in the subject; wherein detection of the moiety diagnoses the disease associated with increased expression or activation of Akt2 in the subject.

BRIEF DESCRIPTION OF DRAWINGS

FIG. 1A. Mass spectrum and structure of $Zn_2$ (EtL1). $2H_2BO_3$. $CH_3CN$ (calculated mass 881.15; observed mass=881.9) FIG. 1B. Mass spectrum and structure of $Zn_2$(EtL1)-phosphoserine (calculated mass=901.5; observed mass=898.9). FIG. 1C. Mass spectrum and structure of $Zn_2$ EtL1 complexed to 13 amino acid long C terminal phosphorylated Akt peptide, phospho-Akt2-13mer (calculated mass=2364.1; observed mass=2361.9). This 13-mer contains the hydrophobic motif of the C-terminus, as well as pSer474, and so is the targeted epitope. FIG. 1D. Mass spectrum and structure of $Zn_2L1$-Az4-PEG2-Biotin (calculated mass $M·2H_2O$=1370.2, (M–N2)·$2H_2O$=1342.2; observed mass $M·2H_2O$=1369, (M–N2)·$2H_2O$=1343.8) (PEG=polyethylene glycol). FIG. 1E. Mass spectrum and structure of $Zn_2L1$-Az4-PEG2-Biotin-phosphoserine (calculated mass=1457.22; observed mass=1454.4). FIG. 1F. Mass spectrum and structure of $Zn_2L1$-Az4-PEG2-Biotin-phosphotyrosine (calculated mass=1532.31; observed mass=1532.39). FIG. 1G. Mass spectrum and structure of $Zn_2L1$-Az4-PEG2-Biotin complexed to the peptide substrate for the pSrc protein Ac-I-pY-GEF (calculated mass=2019.86; observed mass=2019.57).

FIG. 11A. Synthesis of molecule S1. FIG. 11B. Mass spectrometric analysis of mono-L.

FIG. 12A. Synthesis of S2. FIG. 12B. Mass spectrometric analysis of S2.

FIGS. 13A-B: The synthesis and characterization of bi-L. FIG. 13A. Synthesis of molecule S3. FIG. 13B. Mass spectrometric analysis of bi-L.

FIG. 14A. Synthesis of molecule S4. FIG. 14B. Mass spectrometric analysis of Anchor-3N.

FIG. 18A. Structure of the monoligand peptide mono-L developed against the target epitope. FIG. 18B. 1° ligand is linked to the Zn chelator using the Cu(I) catalyzed click reaction. The synthesized molecule 2 binds to the Akt2 fragment containing pS474 to form Complex-2, which is used as the target in the biligand screen. FIG. 18C. Molecular structure of the biligand bi-L isolated in the screen against the target peptide. 1° ligand (in red) is linked, through Cu catalyzed Alkyne Azide Cycloaddition (CuAAC) reaction, to the 2° ligand (in blue). FIG. 18D. An azide is appended at the N terminal of the 2° peptide to synthesize peptide anchor-3N, which is used in screening for 3° ligands that click to the N-terminus of the biligand. FIG. 18E. An alkyne is appended to the C terminal of the 1° peptide to synthesize peptide anchor-3C, which is used in screening for 3° ligands that click to the C-terminus of the biligand.

FIG. 37: UniProt ID and amino acid sequence for human Akt1. The highlighted portion of the sequence corresponds to the 32-mer C-terminal fragments shown in FIG. 23D. The underlined serine residue is phosphorylated in the active protein.

FIG. 38: UniProt ID and amino acid sequence for human Akt2. The highlighted portion of the sequence corresponds to the 32-mer C-terminal fragments shown in FIG. 23D. The underlined serine residue is phosphorylated in the active protein.

FIG. 39: UniProt ID and amino acid sequence for human Akt3. The highlighted portion of the sequence corresponds to the 32-mer C-terminal fragments shown in FIG. 23D. The underlined serine residue is phosphorylated in the active protein.

DETAILED DESCRIPTION

Figure 1A:
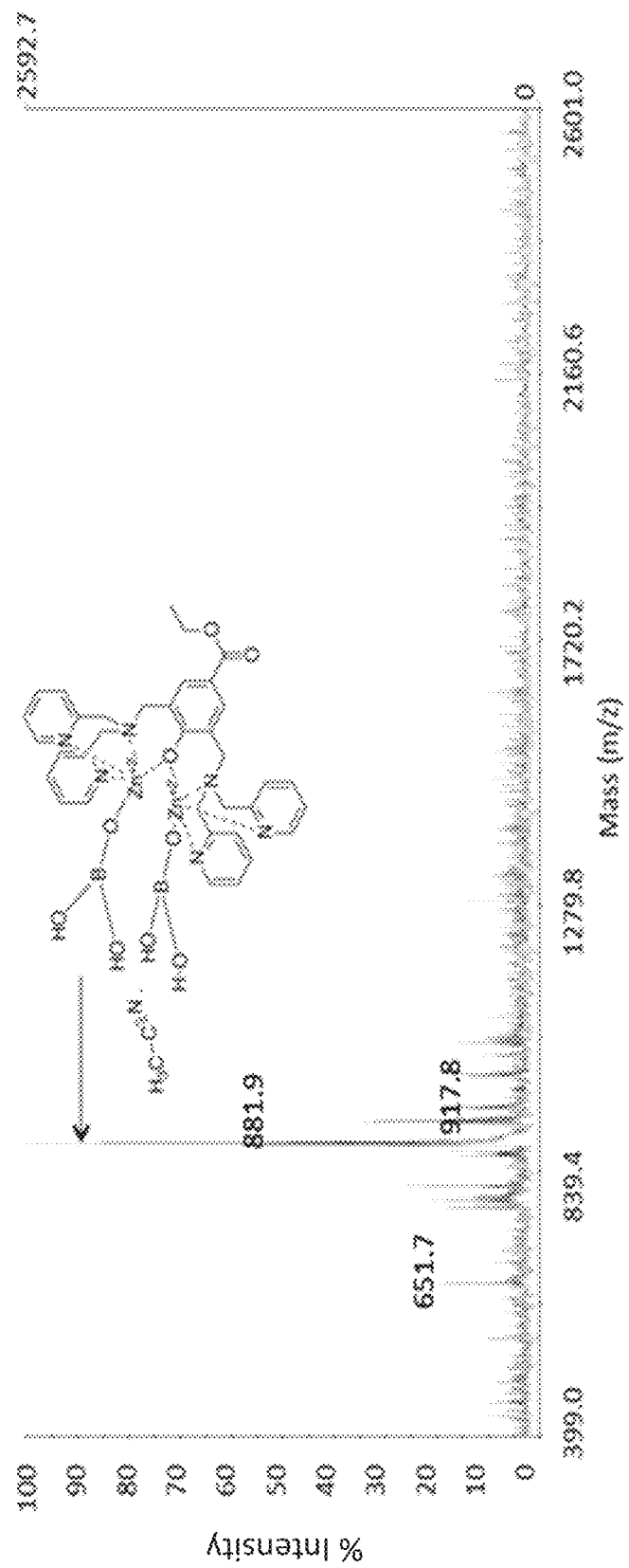
FIGS. 1A-G: The structure and Maldi TOF spectra of dinuclear zinc complexes with phosphorylated amino acids and phosphorylated peptides. Structure and Maldi TOF spectra of dinuclear zinc complexes with phosphorylated amino acids and phosphorylated peptides.
Figure 1B:
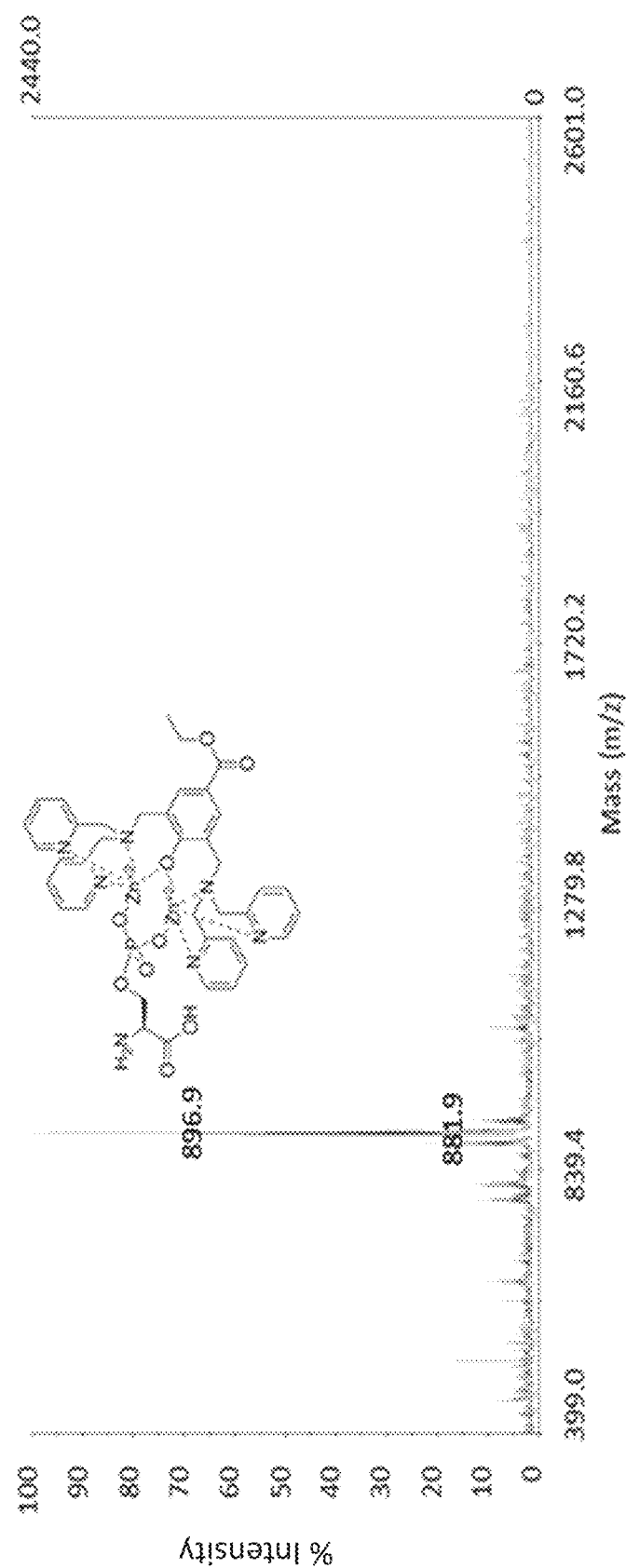
Figure 1C:
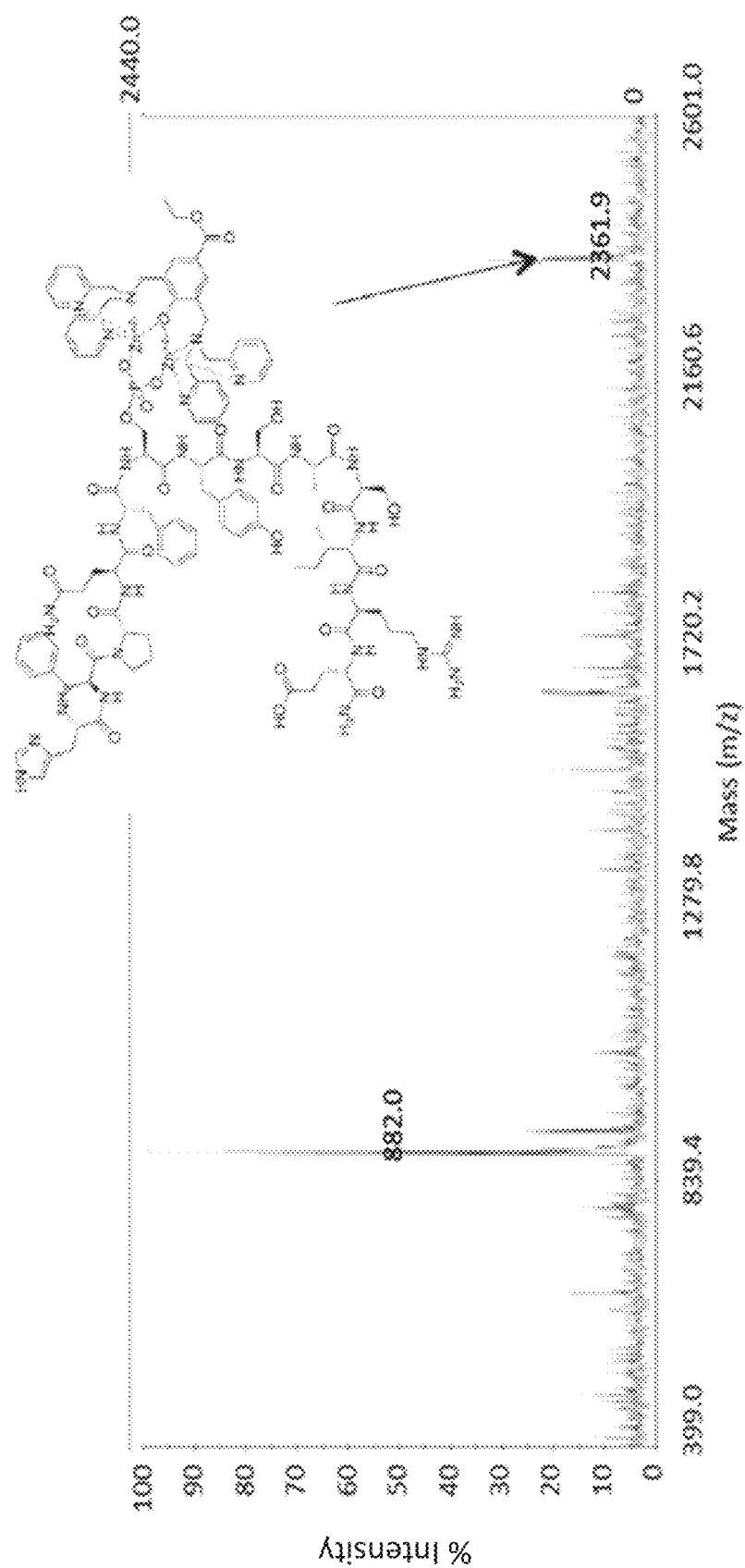

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, the terms "capture agent of the invention", and "capture agents of the invention" refer to synthetic protein-catalyzed capture agents which bind Akt (e.g., Akt2), as described herein.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Aminocarbonyl" refers to a radical of the formula —C(=O)$NR_aR_a$, where each $R_a$ is independently H, alkyl or a linker moiety.

"α-amino carbonyl" refers to a radical of the formula —C(=O)$CR_b$($NR_aR_a$)—, where each $R_a$ is independently H, alkyl or a linker moiety and $R_b$ is H or alkyl. In some embodiments, an alpha amino carbonyl is part of a cyclic moiety (e.g., peptide) where the carbonyl is within the ring and the amino ($NR_aR_a$) is exocyclic. For example, in certain embodiments and alpha aminocarbonyl is useful for Edman degradation of cyclic peptides.

"α-amido carbonyl" refers to a radical of the formula —C(=O)$CR_b$(N(C=O)$R_aR_a$)—, where each $R_a$ is independently H, alkyl or a linker moiety and $R_b$ is H or alkyl. In some embodiments, an alpha amido carbonyl is part of a cyclic moiety (e.g., peptide) where the carbonyl is within the ring and the amido (N(C=O)$R^aR^a$) is exocyclic.

"Alkylamino" refers to a radical of the formula —$NHR^a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —R$_b$R$_f$ where R$_b$ is an alkylene chain as defined above and R$_f$ is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $C(=O)R_g$, $C(=O)OR_g$, $C(=O)NR_gR_h$, $CH_2SO_2R_g$, $CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable peptides of structure (I) or (I') being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled peptides of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled peptides can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed peptides. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds (peptides) of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The term "capture agent" as used herein refers to a composition that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., the Akt2 protein). Typically, the epitope is a polypeptide and it can act on its own as a finite sequence of 10-40 amino acids. In the present disclosure, the epitope is prepared from the 32 amino acid long C-terminal polypeptide fragment of Akt2 (amino acids 450-481) that contains the phosphorylated serine 474 residue (pS474). As described herein, the anchor ligand of the capture agents of the invention are chemically modified variants of a C-terminal polypeptide fragment of Akt2 protein.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-5}$M, such as approximately less than $10^{-6}$ M, $10^{-7}$M, $10^{-8}$ M, $10^{-9}$M or $10^{-10}$ M or even lower.

The term "$K_D$" as used herein refers to the dissociation equilibrium constant of a particular capture agent-antigen interaction. Typically, the capture agents of the invention bind to an Akt protein with a dissociation equilibrium constant ($K_D$) of less than approximately $10^{-6}$M, $10^{-7}$M, $10^{-8}$M, $10^{-9}$M or $10^{-10}$ M or even lower, for example, as determined using surface plasmon resonance (SPR) technology in a Biacore instrument using the capture agent as the ligand and the Akt protein as the analyte, and bind to an Akt protein with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the capture agent, so that when the $K_D$ of the capture agent is very low (that is, the capture agent is highly specific), then the amount with which the affinity for the antigen is lower than the affinity for a non-specific antigen may be at least 10,000 fold.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "KD" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a capture agent may vary according to factors such as the disease state, age, sex, and weight of the individual, and the ability of the capture agent to elicit a desired response in the individual.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab, Fv, Fab', F(ab')$_2$ and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

The term "Akt" collectively refers to the three Akt isoforms (Akt1, Akt2, and Akt3). Akt is a member of the serine/threonine protein kinase family and is involved in processes such as glucose metabolism, apoptosis, and cell proliferation. Akt plays a central regulatory role in growth factor signaling, and serves as a key node in phosphatidylinositol 3-kinase (PI3K) signaling.

Overexpression and/or hyperactivation of Akt is associated with diabetes and many cancers, making Akt an important target for the development of drugs and diagnostics. Overexpression and/or activation of Akt can increase resistance of tumors to chemo or radio therapies. The importance of Akt2 as a therapeutic target has prompted development of both ATP competitive and allosteric inhibitors. The allosteric inhibitors bind to the interface between the membrane docking pleckstrin homology domain (PHD) and the kinase domain.

In cancer cell lines and tissue samples, constitutively active Akt2 is phosphorylated at Ser474. Ser474 in the Akt2 protein (Ser473 in Akt1) is located in the hydrophobic motif (HM) of the C-terminal tail, and is phosphorylated by the Rictor-mTOR. The phosphorylated HM allosterically activates Akt2 by binding to a hydrophobic groove in the N-lobe of Akt2 and enhancing the kinase activity 10-fold. In the PKB crystal structure, the electron density for residues 442-481 is not resolved, suggesting a disordered C-terminus. Evidence suggests that this unstructured epitope lacks a binding pocket, and thus, may not be targetable by traditional small molecule inhibitors. Accordingly, this epitope provides a challenging target, but is also a potentially attractive site for drugging.

Development of Akt Capture Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large ($>10^6$ element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

As described herein, an iterative in situ click chemistry approach was utilized to synthesize a biligand capture agent that specifically binds Akt. This in situ click chemistry approach comprised two steps. First, a synthetic polypeptide derived from Akt was selected as the initial screening target. Second, the secondary ligand selection process took advantage of the fact that an in situ click screen, in which an anchor ligand and full-length protein target are screened against a large OBOC library, will selectively generate multiligand products on the hit beads. This concept was expanded in the form of "product screens," in which the presence of on-bead clicked product is taken to be the signature of a hit bead. Such a product screen can be utilized to increase both the affinity and/or selectivity of the final multiligand capture agent.

The capture agents generated by the methods disclosed herein were found to display binding affinity for Akt. The capture agents were shown to function as both capture and detection agents in ELISA assays and efficiently immunoprecipitate Akt. The capture agents were shown to allosterically modulate the activity of Akt in live cells. The capture agents were turned into proteolysis targeting chimeric molecule (protac) based drug candidates by incorporation of a degradation tag to promote ubiquitination and proteasomal degradation of Akt.

Akt Capture Agents

In one aspect, provided herein is a stable, synthetic capture agent that specifically binds Akt, wherein the capture agent comprises a designed anchor ligand, a designed secondary ligand, optionally a designed tertiary ligand, and optionally a designed quarternary ligand, and wherein the ligands selectively bind Akt. In one embodiment, the capture agent specifically binds Akt2. In another embodiment, the ligands selectively bind Akt2. In another embodiment, the capture agent binds to residues 450-481 of phosphorylated Akt2. In another embodiment, the binding of the capture agent to phosphorylated Akt2 indicates the presence of cancer.

In certain embodiments, provided herein are biligand Akt capture agents comprising two target-binding moieties. The first target-binding moiety is referred to as an anchor ligand, and the second is referred to as a secondary ligand. Also provided are triligand and tetraligand capture agents, wherein the third target-binding moiety is referred to as a tertiary ligand, and the fourth target-binding moiety is referred to as a quarternary ligand.

In certain embodiments, a target-binding moiety comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2,3-triazole.

In certain embodiments, the anchor ligand and secondary ligand are linked to one another via a covalent linkage to form a capture agent biligand. In certain of these embodiments, the anchor ligand and secondary ligand are linked to one another via an amide bond or a 1,4-disubstituted-1,2,3-triazole linkage as shown below:

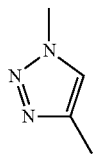

1,4-disubstituted-1,2,3-triazole linkage.

In those embodiments where the anchor and secondary ligands are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the anchor and secondary ligands are linked to one another by a Tz4 linkage having the following structure:

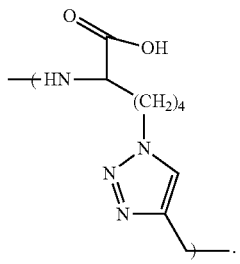

In certain embodiments, the anchor and secondary ligands are linked to one another by a Tz5 linkage having the following structure:

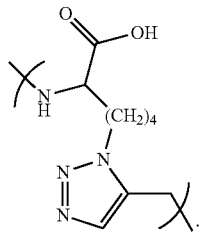

In certain embodiments, the tertiary and/or quarternary ligand is linked to the capture agent biligand by a covalent linkage, preferably via the secondary ligand in the biligand. In certain of these embodiments, the tertiary ligand and the biligand and/or the quarternary ligand and the tertiary ligand are linked to one another by a Tz4 linkage.

In those embodiments wherein one or more of the anchor, secondary, tertiary, and/or quarternary ligands are linked to one another via amide bonds, the amide bond may be formed by coupling a carboxylic acid group and an amine group in the presence of a coupling agent (e.g., O-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein.

In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In $^{11}$C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Methods of Making/Screening Capture Agents

Provided herein in certain embodiments are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorpoarated by reference, herein, in their entireties.

The capture agent production methods disclosed herein begin with identification of a short-chain anchor peptide, then proceed by adding additional covalently coupled peptide ligands via a process that is promoted by the target protein. The specificity and inhibitory potency of the final multiligand capture agent are augmented by the peripheral peptide ligands.

In certain embodiments, the methods provided herein comprise the following steps:
(a) identifying an anchor ligand by the following steps:
    (i) preparing a synthetic target polypeptide corresponding to an epitope of the target protein;
    (ii) preparing a first plurality of candidate peptides to screen against the target polypeptide;
    (iii) contacting the target polypeptide with the first plurality of candidate peptides;
    (iv) selecting a candidate peptide with affinity for the target polypeptide as the anchor ligand, wherein the candidate peptide binds to the target polypeptide; and
    (v) sequencing the anchor ligand;
(b) identifying a secondary ligand by the following steps:
    (i) preparing an anchor ligand selection block comprising the anchor ligand and an azido group or an alkynyl group;
    (ii) preparing a second plurality of candidate peptides to select a secondary ligand for the target protein, the second plurality of peptides comprising an azido group or an alkynyl group if the anchor ligand selection block comprises an alkynyl group and azido group respectively;
    (iii) contacting the anchor ligand selection block and the second plurality of peptides with the target protein;
    (iv) providing a capture agent biligand by forming a disubstituted 1,2,3-triazole linkage between the anchor ligand selection block and the secondary ligand wherein the azido and alkynyl group of the anchor ligand selection block and the secondary ligand are brought in close proximity by binding to the target protein;
    (v) selecting the capture agent biligand that has an affinity with the target protein; and
    (vi) sequencing the secondary ligand;
(c) identifying a tertiary ligand by the following steps:
    (i) preparing a biligand selection block comprising an azido group or an alkynyl group; and
    (ii) repeating steps (b)(ii) to (b)(vi) using a third plurality of candidate peptides until a capture agent having desired binding affinity to the target protein is obtained;
(d) identifying a quarternary ligand and, optionally, additional ligands by the following steps:
    (i) preparing a triligand selection block comprising an azido group or an alkynyl group; and
    (ii) repeating steps (c)(ii) to (c)(vi) using a fourth plurality, fifth plurality, etc., of candidate peptides until a capture agent having desired binding affinity to the target protein is obtained.

In certain embodiments, one or more of the above steps may be omitted. For example, in certain embodiments a known anchor ligand is used. In these embodiments, step (a) is omitted, and the known anchor ligand is used to identify the secondary ligand in step (b). In those embodiments where the target protein is Akt, the anchor ligand may comprise the peptide sequence corresponding to the 32 amino acid long C-terminal polypeptide fragment of Akt2 (amino acids 450-481) that contains a phosphorylated serine 474 residue (pS474). In certain embodiments, this anchor ligand may be modified with an N- or C-terminal biotin prior to step (b).

In certain embodiments, steps (b)(ii) to (b)(vi) are repeated one time, resulting in production of a capture agent triligand.

In certain embodiments, the first, second, and any additional pluralities of candidate peptides comprise a "one bead one compound" (OBOC) peptide library, wherein the peptides comprise 5 to 7 D-amino acid residues and coupled with a D-propargylglycine at the N-terminus. In certain embodiments, the pluralities of candidate peptides may be different. In other embodiments, one or more of the pluralities may contain the same peptide pool.

In certain embodiments, the secondary ligand is covalently bound to the anchor ligand, and the tertiary ligand is covalently bound to the secondary ligand. In another embodiment, the secondary and tertiary ligands are covalently bound to the anchor ligand.

In certain embodiments, the methods provided herein utilize a known peptide target. In a particular embodiment, the peptide target comprises the sequence ITPPDRYDSLGLLELDQRTHFPQF(pS)YSASIRE (SEQ ID NO:15). In a particular embodiment, the peptide target comprises the sequence HFPQF(pS)YSASIRE (SEQ ID NO:26).

In certain embodiments, the anchor ligand used for the screening process may be modified with a biotin. For example, the anchor ligand used for the screening process may be Biotin-PEG$_5$-LIGAND-Pra.

In one embodiment, the screening/preparation process comprises the following steps:
a) contacting the Akt with the Biotin-PEG$_5$-LIGAND-Pra anchor ligand to provide an Akt-anchor complex;
b) contacting the Akt-anchor complex with a first plurality of candidate peptides to select a secondary ligand, the peptides coupled with an Az4-CONH$_2$ moiety at its N-terminus;
c) providing a capture agent biligand by forming a disubstituted-1,2,3-triazole linkage between the anchor ligand selection block and the secondary ligand, wherein the azido and alkynyl group of the anchor ligand selection block and the secondary ligand are brought in close proximity by binding to the target protein to provide a bead modified with the capture agent biligand;
d) selecting the beads modified with the capture agent biligand;
e) removing the capture agent biligands from the beads;
f) sequencing the secondary ligand of the capture agent biligand;

g) preparing the capture agent biligand with an N-terminal Biotin-(PEG)₅ label and a C-terminal Az4; and h) repeating the above steps until an Akt capture agent having the desired properties is identified.

In certain embodiments, methods are provided for synthesizing a capture agent as provided herein. In certain embodiments, these methods comprise:

a) preparing a synthesis block of a target-binding moiety, the synthesis block comprising the target-binding moiety and at least one reactive group that can form a desired linkage with another synthesis block, wherein:
   i) the linkage is selected from the group consisting of amide linkage, 1,4-disubstituted 1,2,3-triazole linkage, and 1,5-disubstituted 1,2,3-triazole linkage; and
   ii) all other active functional groups of the target-binding moiety are protected to avoid undesired reactions; and b) coupling the synthesis blocks of the target-binding moieties to provide the capture agent.

Methods for Targeting Akt

An approach for synthesizing molecules that bind Akt is described and demonstrated. The invention includes first preparing a peptide or polypeptide fragment corresponding to the the 32 amino acid long C-terminal polypeptide fragment of Akt2 (amino acids 450-481) that contains a phosphorylated serine 474 residue (pS474). That polypeptide can be site-specifically modified by either substituting one of the naturally occurring amino acids with an artificial amino acid, or the polypeptide fragment is modified after synthesis by chemically altering a specific amino acid. In both cases, the polypeptide can be modified to incorporate either an alkyne or an azide chemical group near the site-specific modification. That azide (or alkyne) containing fragment is then incubated with a very large molecular library. This library, while typically chemically diverse, is also characterized by the fact that each element contains an alkyne (or, instead, each element contains an azide) group. The incubation can be done under conditions that the modified polypeptide fragment can provide a catalytic scaffold for promoting the covalent coupling between select library elements and the polypeptide fragment. In this embodiment, it promotes this coupling by catalyzing the formation of a triazole linkage that is the reaction product of the acetylene and azide groups. According to several embodiments, the selectivity of this catalyzed process is very high. This means that only a very small fraction of the elements in the molecular library will be coupled. Those elements are identified through analytical techniques, and then tested for binding to the polypeptide fragment, or to the entire protein biomolecule from which the polypeptide fragment was extracted. This approach provides a route towards identifying molecules that selectively bind to the intended epitope of the protein target. Approaches known in the art may then be utilized to increase the selectivity and the affinity of the identified binders, without sacrificing their epitope selective binding characteristics.

The following steps are performed in one embodiment of the process. A protein target (1) is selected for developing capture agent molecules that will bind to that protein target. The protein target contains an epitope with a known sequence of amino acids (2). A polypeptide fragment (3) corresponding to the epitope of the protein is synthesized, but with two modifications. First, (3) is either substituted or chemically modified so as to provide an azide or alkyne group. Second, a site on the polypeptide is modified (4) with a label (a fluorophore or biotin group, for example) for use during the screening steps. There are many ways through which this label can be introduced.

If a molecular library of 1 million molecules, designed to span a broad chemical space, is incubated with a ~50-100 nM concentration solution of the modified polypeptide fragment (3), under standard blocking conditions to prevent non-selective binding, then that screen will generate about 20-100 hit molecules. Of those hit molecules, a small number (1-10) will be molecules that specifically bind to the protein target of interest. Approaches described herein can then be utilized to increase the affinity and specificity of those protein target-specific binders.

In Vitro

For detection of Akt in solution, a capture agent of the invention can be detectably labeled, then contacted with the solution, and thereafter formation of a complex between the capture agent and the Akt target can be detected. As an example, a fluorescently labeled capture agent can be used for in vitro Akt detection assays, wherein the capture agent is added to a solution to be tested for Akt under conditions allowing binding to occur. The complex between the fluorescently labeled capture agent and the Akt target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing Akt is contacted with the immobilized binding moiety, non-binding materials are washed away, and complexed polypeptide is detected using a suitable detection reagent for recognizing Akt.

For detection or purification of soluble Akt from a solution, capture agents of the invention can be immobilized on a solid substrate such as a chromatographic support or other matrix material, then the immobilized binder can be loaded or contacted with the solution under conditions suitable for formation of a capture agent/Akt complex. The non-binding portion of the solution can be removed and the complex can be detected, for example, using an anti-Akt antibody, or an anti-binding polypeptide antibody, or the the Akt can be released from the binding moiety at appropriate elution conditions.

In Vivo

Diagnostic Imaging

A particularly preferred use for the capture agents of the invention is for creating visually readable images of Akt or Akt-expressing cells in a biological fluid, such as, for example, in human serum. The Akt capture agents disclosed herein can be converted to imaging reagents by conjugating the capture agents with a label appropriate for diagnostic detection. Preferably, a capture agent exhibiting much greater specificity for Akt than for other serum proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling a capture agent with a detectable label or radiotherapeutic construct, one or more peptides or constructs of the invention can be conjugated with for example, avidin, biotin, or an antibody or antibody fragment that will bind the detectable label or radiotherapeutic.

A. Magnetic Resonance Imaging

The Akt capture agents described herein can advantageously be conjugated with a paramagnetic metal chelate in order to form a contrast agent for use in MRI. Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, $Gd^{3+}$, is particularly preferred for MRI contrast agents, due to its high relaxivity and low toxicity, with the further advantage that it exists in only one biologically accessible oxidation state, which minimizes undesired metabolysis of the metal by a patient. Another useful metal is $Cr^{3+}$, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4, 7,-tricarboxymethyl-1,4,7,10-teraazacyclododecane (DO3A), ethylenediaminetetraacetic acid (EDTA), and 1,4, 8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTHA); derivatives of 1,5,10?N,N',N"-tris(2,3-dihydroxybenzoyl)-tricatecholate (LICAM); and 1,3,5-N,N',N"-tris(2,3-dihydroxybenzoyl)aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143, 274, all of which are hereby incorporated by reference.

In accordance with the present invention, the chelator of the MRI contrast agent is coupled to the Akt capture agent. The positioning of the chelate should be selected so as not to interfere with the binding affinity or specificity of the Akt capture agent. The chelate also can be attached anywhere on the capture agent.

In general, the Akt capture agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the Akt binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly (vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the Akt capture agent using such linkers (WO 95/28967, WO 98/18496, WO 98/18497 and discussion therein). The Akt binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between Akt-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging Akt-expressing tissues, such as tumors, intravenous or intraarterial administration is preferred. For MRI, it is contemplated that the subject will receive a dosage of contrast agent sufficient to enhance the MR signal at the site Akt expression by at least 10%. After injection with the Akt capture agent containing MRI reagent, the patient is scanned in the MRI machine to determine the location of any sites of Akt expression. In therapeutic settings, upon identification of a site of Akt expression (e.g., fluid or tissue), an anti-cancer agent (e.g., inhibitors of Akt) can be immediately administered, if necessary, and the patient can be subsequently scanned to visualize viral load.

B. Nuclear Imaging (Radionuclide Imaging) and Radiotherapy

The Akt capture agents of the invention can be conjugated with a radionuclide reporter appropriate for scintigraphy, SPECT, or PET imaging and/or with a radionuclide appropriate for radiotherapy. Constructs in which the Akt capture agents are conjugated with both a chelator for a radionuclide useful for diagnostic imaging and a chelator useful for radiotherapy are within the scope of the invention.

For use as a PET agent a peptide or multimeric polypeptide construct is complexed with one of the various positron emitting metal ions, such as $^{51}$Mn, $^{52}$Fe, $^{60}$Cu, $^{68}$Ga, $^{72}$As, $^{94m}$Tc, or $^{110}$In. The binding moieties of the invention can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{117m}$Sn, $^{149}$Pm, $^{153}$Sm, $^{161}$Tb, $^{166}$Tb, $^{166}$Dy, $^{166}$Ho, $^{175}$Yb, $^{177}$Ln, $^{186/188}$Re, and $^{199}$Au. $^{99m}$Tc is useful for diagnostic applications because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo-$^{99m}$Tc generator. $^{18}$F, 4-[$^{18}$F]fluorobenzaldehyde ($^{18}$FB), Al[$^{18}$F]-NOTA, $^{68}$Ga-DOTA, and $^{68}$Ga-NOTA are typical radionuclides for conjugation to Akt capture agents for diagnostic imaging.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656,254; and 5,688,487. Certain $N_3S$ chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

The chelators can be covalently linked directly to the Akt capture agent via a linker, as described previously, and then directly labeled with the radioactive metal of choice (see, WO 98/52618, U.S. Pat. Nos. 5,879,658, and 5,849,261).

Akt capture agents comprising $^{18}$F, 4-[$^{18}$F]fluorobenzaldehyde ($^{18}$FB), Al[$^{18}$F]-NOTA, $^{68}$Ga-DOTA, and $^{68}$Ga-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the reagents of this invention, the technetium complex, preferably a salt of $^{99m}$Tc pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with $^{99m}$Tc. Alternatively, the complex can be formed by reacting a peptide of this invention conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}$Tc pertechnetate salts useful with the present invention are included the alkali metal salts such as the sodium salt, or ammonium salts or lower alkyl ammonium salts.

Preparation of the complexes of the present invention where the metal is radioactive rhenium can be accomplished using rhenium starting materials in the +5 or +7 oxidation state. Examples of compounds in which rhenium is in the Re(VII) state are $NH_4ReO_4$ or $KReO_4$. Re(V) is available as, for example, [$ReOCl_4$](NBu$_4$), [$ReOCl_4$](AsPh$_4$), $ReOCl_3$(PPh$_3$)$_2$ and as $ReO_2$(pyridine)$^{4+}$, where Ph is phenyl and Bu is n-butyl. Other rhenium reagents capable of forming a rhenium complex also can be used.

Radioactively labeled PET, SPECT, or scintigraphic imaging agents provided by the present invention are encompassed having a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled Akt capture agent according to the invention provide 10-20 mCi. After injection of the radionuclide-labeled Akt capture agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods including, but not limited to, a single or multiple IV or IP injections, using a quantity of radioactivity that is sufficient to cause damage or ablation of the targeted Akt-expressing tissue, but not so much that substantive damage is caused to non-target (normal tissue). The quantity and dose required is different for different constructs, depending on the energy and half-life of the isotope used, the degree of uptake and clearance of the agent from the body and the mass of the Akt-expressing tissue. In general, doses can range from a single dose of about 30-50 mCi to a cumulative dose of up to about 3 Ci.

The radiotherapeutic compositions of the invention can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, δ, or γ cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an $^{18}$F radiolabeled prosthetic group onto an Akt capture agent. In one embodiment, 4-[$^{18}$F]fluorobenzaldehyde ($^{18}$FB) is conjugated onto a capture agent bearing an aminooxy moiety, resulting in oxime formation. In another embodiment, [$^{18}$F] fluorobenzaldehyde is conjugated onto a capture agent bearing an acyl hydrazide moiety, resulting in a hydrazone adduct. 4-Fluorobenzaldehyde, can be prepared in $^{18}$F form by displacement of a leaving group, using $^{18}$F ion, by known methods.

$^{18}$F-labeled capture agents can also be prepared from capture agents possessing thiosemicarbazide moieties under conditions that promote formation of a thiosemicarbozone, or by use of a $^{18}$F-labeled aldehyde bisulfite addition complex.

The above methods are particularly amenable to the labeling of capture agents, e.g., the capture agents described herein, which can be modified during synthesis to contain a nucleophilic hydroxylamine, thiosemicarbazide or hydrazine (or acyl hydrazide) moiety that can be used to react with the labeled aldehyde. The methods can be used for any capture agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding F-18 radiolabeled peptide sequence.

In the instances when the oxime, thiosemicarbazone or hydrazone linkages present in vivo instability, an additional reduction step may be employed to reduce the double bond connecting the peptide to the F-18 bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiff's base involving a peptide and 4-[$^{18}$F]fluorobenzaldehyde and directly reducing the Schiff's base using reducing agents such as sodium cyanoborohydride.

The 4-[$^{18}$F]fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-

902, 2004; and Schottelius et al., Clinical Cancer Research, 10, 3593-3606, 2004. The Na.sup.18F in water may be added to a mixture of kryptofix and $K_2CO_3$. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters® Oasis HLB LP extraction cartridge. The cartridge may be washed with 9:1 water:acetonitrile and water to remove unbound F-18 and unreacted 4-trimethylammoniumbenzaldehyde triflate. The 4-[$^{18}$F] fluorobenzaldehyde may then be eluted from the cartridge with methanol in fractions.

Therapeutic Applications

Provided herein in certain embodiments are methods of using the Akt capture agents disclosed herein to identify, detect, quantify, and/or separate Akt in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in certain embodiments are methods of using the Akt capture agents disclosed herein to diagnose and/or classify (e.g., stage) a condition associated with Akt expression, including for example various cancers. In certain of these embodiments, the methods comprise (a) obtaining a biological sample from a subject; (b) measuring the presence or absence of Akt in the sample with the Akt capture agent; (c) comparing the levels of Akt to a predetermined control range for Akt; and (d) diagnosing a condition associated with Akt expression based on the difference between Akt levels in the biological sample and the predetermined control.

The Akt capture agents of the invention also can be used to target genetic material to Akt expressing cells. Thus, they can be useful in gene therapy, particularly for treatment of cancer. In this embodiment, genetic material or one or more delivery vehicles containing genetic material useful in treating cancer can be conjugated to one or more Akt capture agents of the disclosure and administered to a patient. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In an embodiment the capture agents of the invention are utilized in gene therapy for treatment of cancer. In this embodiment, genetic material, or one or more delivery vehicles containing genetic material, e.g., useful in treating cancer, can be conjugated to one or more Akt capture agents of this disclosure and administered to a patient.

Constructs including genetic material and Akt capture agents of this disclosure can be used, in particular, to selectively introduce genes into proliferating cancer cells (e.g., epithelial cells), which can be useful to treat cancer.

Therapeutic agents and the Akt capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and Akt binding polypeptide can be coexpressed from the same synthetic gene, created using recombinant DNA techniques, as described above. The coding sequence for the Akt binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the Akt binding polypeptide. A particular advantage of this general approach is that concatamerization of multiple, tandemly arranged Akt capture agents is possible, thereby increasing the number and concentration of Akt binding sites associated with each therapeutic protein. In this manner, Akt binding avidity is increased, which would be expected to improve the efficacy of the recombinant therapeutic fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

As described herein, the capture agents of the invention are useful for treating an Akt-expressing cancer or allosterically modulating Akt activity. Also provided herein is a method to turn the capture agents into proteolysis targeting chimeric molecule (protac) based drug candidates by incorporation of a degradation tag. Binding of the protac capture agent to Akt results in selective targeting of degradation signals to Akt that could result in ubiquitination and proteasomal degradation of Akt. In one embodiment the Akt protein is Akt2. In another embodiment, the tag is the Hif-1α degradation peptide ALAPYIP (SEQ ID NO:27) (see, e.g., Example 16 and FIG. 36).

Other tags that can be used to provide degradation signals include nutlin-3 (Schneekloth, et al. Bioorg. Med. Chem. Lett. 18, 5904-5908 (2008)); Boc3Arginine (Long, et al. Chem. Biol. 19, 629-637 (2012)); methyl bestatin (Itoh, et al. J. Am. Chem. Soc. 132, 5820-5826 (2010)); HyT13 or HyT36 (Tae, et al. ChemBioChem 13, 538-541 (2012)); HIF-1α VHL binding peptides (Hines, et al. Proc. Natl. Acad. Sci. 110, 8942-8947 (2013) and Sakamoto, et al. Mol. Cell. Proteomics 2, 1350-1358 (2003)); lysosomal-targeting peptide derived from Rnase A, hsc 70 and hemoglobin (Fan, et al. Nat. Neurosci. 17, 471-480 (2014)); amd SCFTrCP-targeting IκBα phosphopeptide (Sakamoto, et al. Proc. Natl. Acad. Sci. 98, 8554-8559 (2001)) Each of the references cited in the paragraph are incorporated by reference herein in their entireties.

EXAMPLES

Example 1: Akt Epitope-Targeted PCC Development

For the present work, the two reacting species are peptides—one peptide (the anchor) is a chemically modified variant of the 32 amino acid long C-terminal polypeptide fragment of Akt2 (amino acids 450-481) that contains a phosphorylated serine 474 residue (pS474), and the second peptide is selected via an in situ click screen from a large ($10^6$ element) one-bead-one-compound (OBOC) peptide library.

The PCC Agents developed here were designed to capture Akt binders that are selective for amino acids 450-481 of Akt2. The epitope targeting strategy, when combined with sequential in situ click chemistry, permitted the development of a series of peptide multi-ligands (PCC Agents) that are targeted near a key phosphorylation site of Akt2. The strategy relies on the use of dinuclear Zn(II)-DPA complex that binds to the phosphorylated residue of interest, and presents a biotin label and an azide functionality near that site. The strategy is initiated using only a fragment representing the phosphorylated epitope of the target. This all-synthetic approach permits stringent chemical characterization of the chemical species employed. The strategy is used to develop an initial PCC Agent monoligand, a PCC Agent biligand and two PCC Agent triligands. The strongest binding triligand (the N-tL) exhibits a ~20 nM affinity. Epitope and protein isoform specificity is shown for both triligands.

For the in situ click screens, the target Akt2 is incubated with an excess of the selected monoligand and a large OBOC library at 4° C. overnight. The OBOC library is synthesized on TentaGel resin (Rapp Polymere, Tuebingen, Germany), and is a comprehensive library of 5-mers with a 6th amino acid at the C-terminus presenting an alkyne functionality. To help ensure chemical and biochemical stability, the OBOC library is comprised of non-natural (D) stereoisomers of the 20 natural amino acids, excluding cysteine and methionine. The in situ screen is designed to identify a secondary (2°) peptide that, when coupled to the monoligand, forms a biligand with increased selectivity and/or affinity for the target Akt2. The screen proceeds stepwise. In Step 1, the OBOC library is cleared of beads that exhibit non-specific binding to alkaline phosphatase-conjugated mouse anti-biotin antibody, which is used as a detection reagent in a later step. Step 2 is a target screen, and so is designed to detect the presence of the bound Akt2 target to specific beads, and defines possible hits. The Step 3 screen is designed to remove those beads from the pool of potential hits that also exhibit off-target binding to anti-Akt antibody. Step 4 is called a product screen, and is unique to sequential in situ click screens. This screen is designed to detect for the presence of in situ clicked reaction products, which are those hit beads containing the triazole-linked monoligand. Typically, Step 2 yields a few hundred hits (~0.05% of the OBOC library). Step 3 reduces that pool by a factor of 2 or 3 to about 100 hits, and Step 4 further reduces the number of hits to around 10. This is a manageable number, meaning that each hit can be separately synthesized as a biligand using Cu(I) catalyzed click chemistry to couple the monoligand and 2° peptides.

Example 1.2: Materials

Fmoc amino acids were purchased from Anaspec and AAPPTec and used as received. TentaGel S—$NH_2$ resin (diameter 90 μm, capacity 0.28 mmol/g) was obtained from Anaspec and utilized for OBOC library construction. Biotin NovaTag™ resin, Biotin-PEG NovaTag™ resin, Fmoc-NH-(PEG)2-OH (13 atoms) were obtained from EMD Chemicals, Inc. and used for synthesis of biotinylated peptides. Amide Sieber resin (capacity 0.3-0.6 mmol/g) purchased from Anaspec was used for synthesis of protected peptides. NMP (1-methyl-2-pyrrolidinone), HATU ((2-(7-$Az_4$-1H-benzotriazole-1-yl)-1,1,3,3-tetramethylammonium hexafluorophosphate) and DIEA (N,N'-diisopropylethylamine) used in peptide synthesis were bought from EMD Chemicals, Inc., ChemPep and Sigma-Aldrich respectively. DMF (N,N'-dimethylformamide), piperidine, TFA (trifluoroacetic acid, 98% min. titration), and TES (triethylsilane) were purchased from Sigma-Aldrich. 5-Azido-pentanoic acid was purchased from Bachem Americas, Inc. BCIP (5-Bromo-4-chloro-3-indolyl phosphate) was purchased from Promega.

Active Akt2 (with N terminal $His_6$ (SEQ ID NO:28) tag) was purchased from Abcam. Inactive Akt2 (with N terminal $His_6$ (SEQ ID NO:28) tag) was purchased from BPS Bioscience. Active Akt1 and Akt3 (with N terminal $His_6$ (SEQ ID NO:28) tag) used in ELISA assays were purchased from Sigma Aldrich. Mouse anti biotin antibody-Alkaline Phosphatase conjugate used in screens was purchased from Sigma Aldrich. Anti $His_6$ (SEQ ID NO:28) mouse antibody, goat anti mouse IgG-Alkaline Phosphatase conjugate used in screens were purchased from Abcam. Mouse anti biotin monoclonal antibody-Horse Radish Peroxide conjugate was purchased from Cell Signaling. Anti $His_6$ (SEQ ID NO:28) mouse monoclonal antibody and goat anti mouse IgG-Horse Radish Peroxide conjugate were bought from Abcam. Anti Akt (pan) rabbit antibody (11E7), and mouse anti-rabbit antibody-Horse Radish Peroxide conjugate, used in Western blot and dot blot, were purchased from Cell Signalling. Biotinylated mouse PhosphoS473 (pS473) Akt antibody used in immunoprecipitation and PhosphoS473 Akt antibody used in western blot was purchased from Cell Signaling. Non-radioactive Akt kinase assay kit was purchased from Cell Signaling.

Example 1.3: Synthesis of ethyl 3,5-bis((bis(pyridin-2-ylmethyl)amino)methyl)-4-hydroxybenzoate [H(EtL$_1$)]

Figure 3:
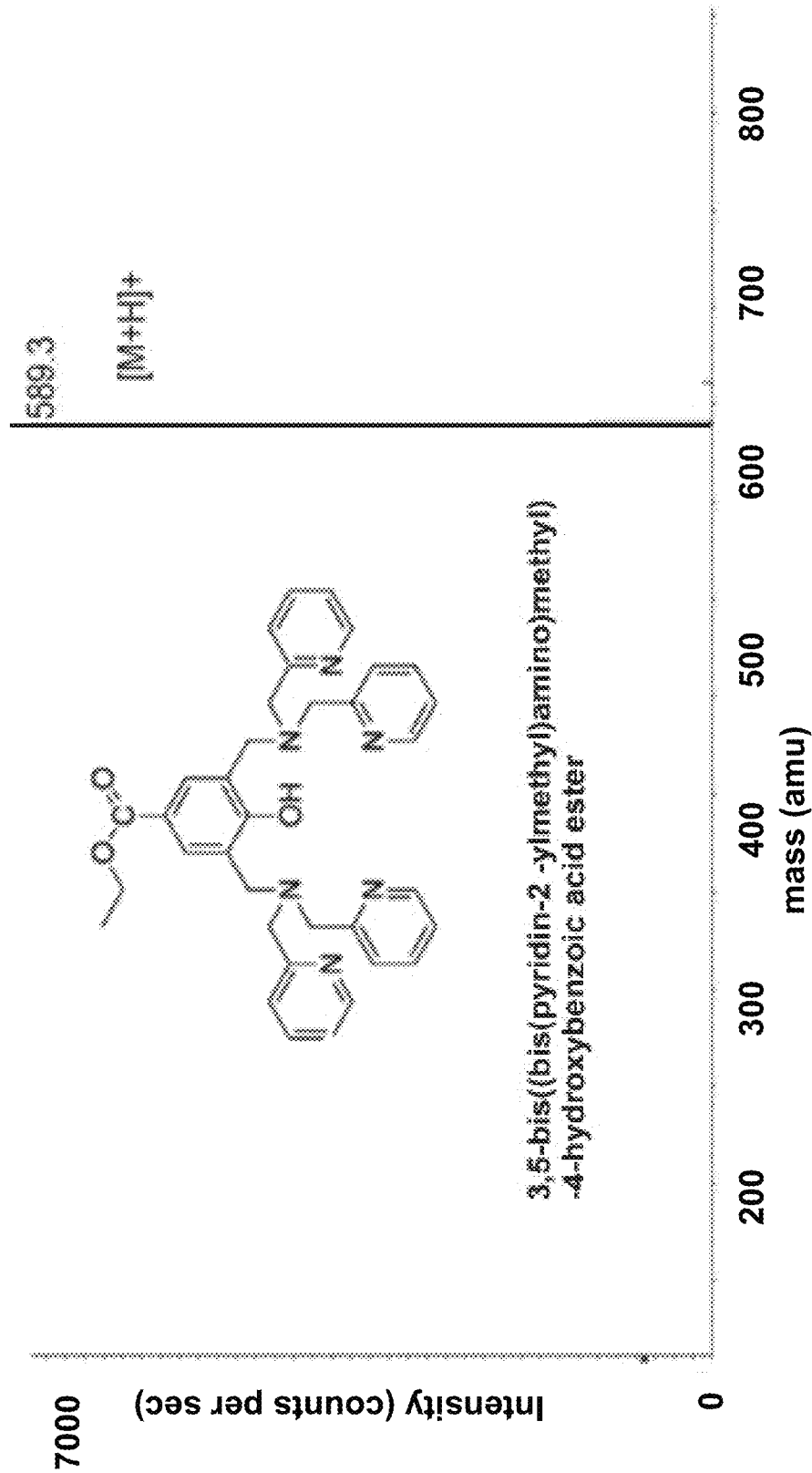
FIG. 3: The synthesis of ethyl 3,5-bis((bis(pyridin-2-ylmethyl)amino)methyl)-4-hydroxybenzoate [H(EtL$_1$)].

N, N-di(2-picolyl) amine (2.50 g, 12.5 mmol) in ethanol/water/HCl (30 mL/90 mL/0.6 mL of 2M) was added to paraben (830 mg, 5 mmol) and paraformaldehyde (475 mg, 15.67 mmol). The mixture was heated under reflux for 3 days and then allowed to cool to room temperature. Then dichloromethane (300 mL) and water (100 mL) was added to the reaction mixture and a liquid phase extraction was done. The organic phase, containing the compound, was washed once with 300 mL of water and dried over anhydrous sodium sulphate. A yellowish gummy semisolid was obtained after evaporation of solvent. Column chromatography on silica gel with eluents dichloromethane/methanol/ammonium hydroxide afforded light yellow semi solid. The calculated mass was 588.6 [M+H] and the observed mass was 589.29 [M+H] (FIG. 3).

Example 1.4: Synthesis of 3,5-bis((bis(pyridin-2-ylmethyl)amino)methyl)-4-hydroxybenzoic acid [H(L$_1$)]

Figure 4:
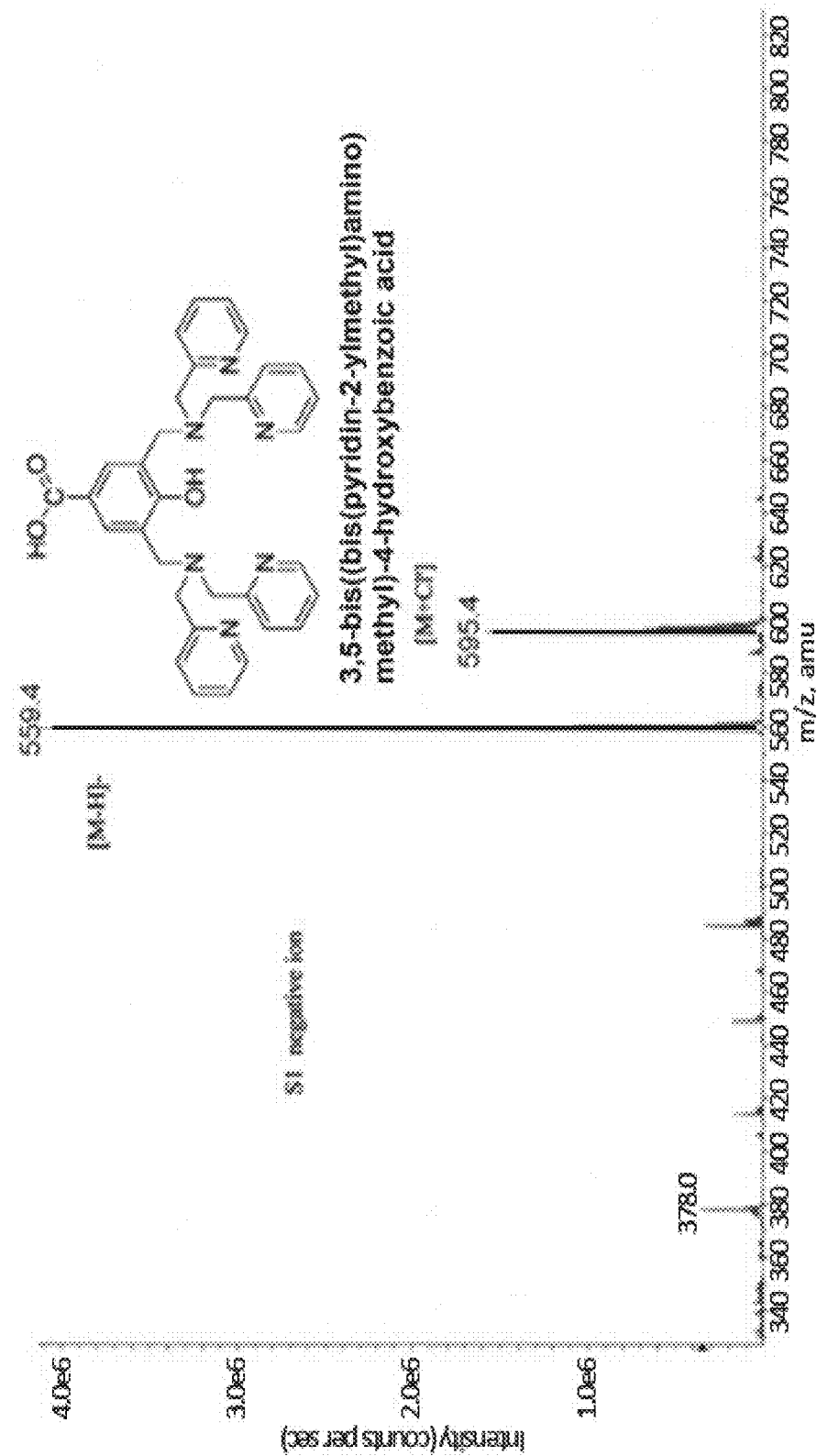
FIG. 4: The synthesis of 3,5-bis((bis(pyridin-2-ylmethyl)amino)methyl)-4-hydroxybenzoic acid [H(L$_1$)].

The purified semisolid was dissolved in 2 M NaOH in 1:1 ethanol/water solution and stirred at 60° C. for 2 days. Then the solution was neutralized by concentrated hydrochloric acid. The compound was extracted with methanol and used in further synthesis. The calculated mass was 559.25 [M−H] and the observed mass was 559.4 [M−H] (FIG. 4).

Example 1.5: Synthesis of 3,5-bis((bis(pyridin-2-ylmethyl)amino)methyl)-4-hydroxybenzoxo dizinc complex [Zn$_2$(EtL$_1$)]

Figure 5:
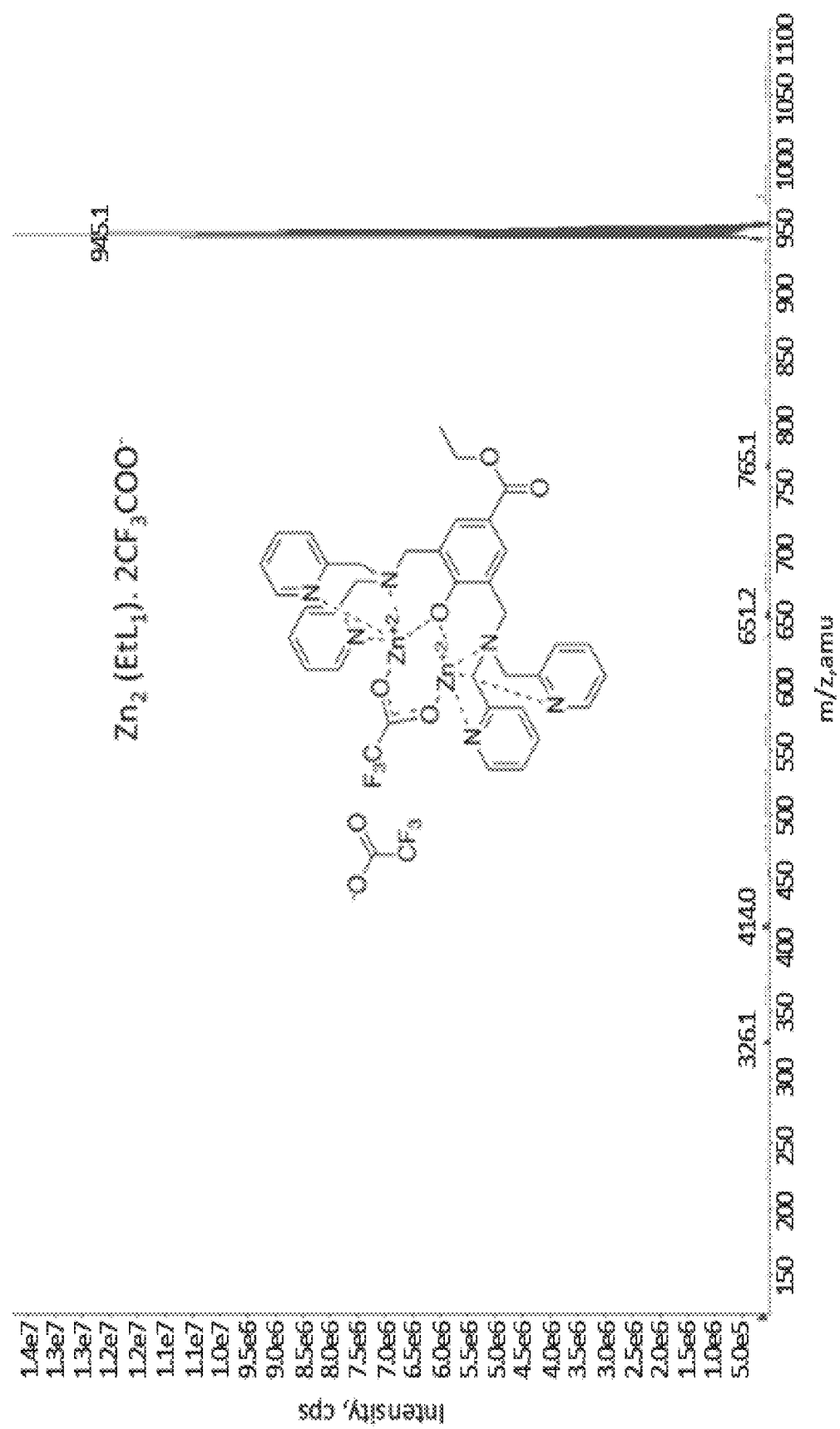
FIG. 5: The synthesis of 3,5-bis((bis(pyridin-2-ylmethyl)amino)methyl)-4-hydroxybenzoxo dizinc complex [$Zn_2$(EtL$_1$)].

Two equivalents of zinc acetate was dissolved in methanol and added to one equivalent of ethyl 3,5-bis((bis(pyridin-2-ylmethyl)amino)methyl)-4-hydroxybenzoate and stirred overnight at room temperature. The solvent was removed under reduced pressure and the solid was purified using a gradient of water and acetonitrile and 0.1% TFA on the RP-HPLC (Beckman Coulter System Gold 126 Solvent Module and 168 Detector) using a C18 reversed phase semi-preparative column (Phenomenex Luna 10 µm, 250× 10 mm). The calculated mass was 944.48 [M−H] and the observed mass was 945.10 [M−H] (FIG. 5).

Example 1.6: Synthesis of 3,5-bis((bis(pyridin-2-ylmethyl)amino)methyl)-4-hydroxybenzoxo dizinc complex [Zn$_2$(L$_1$)-Az4-PEG$_2$-biotin]

Figure 1D:
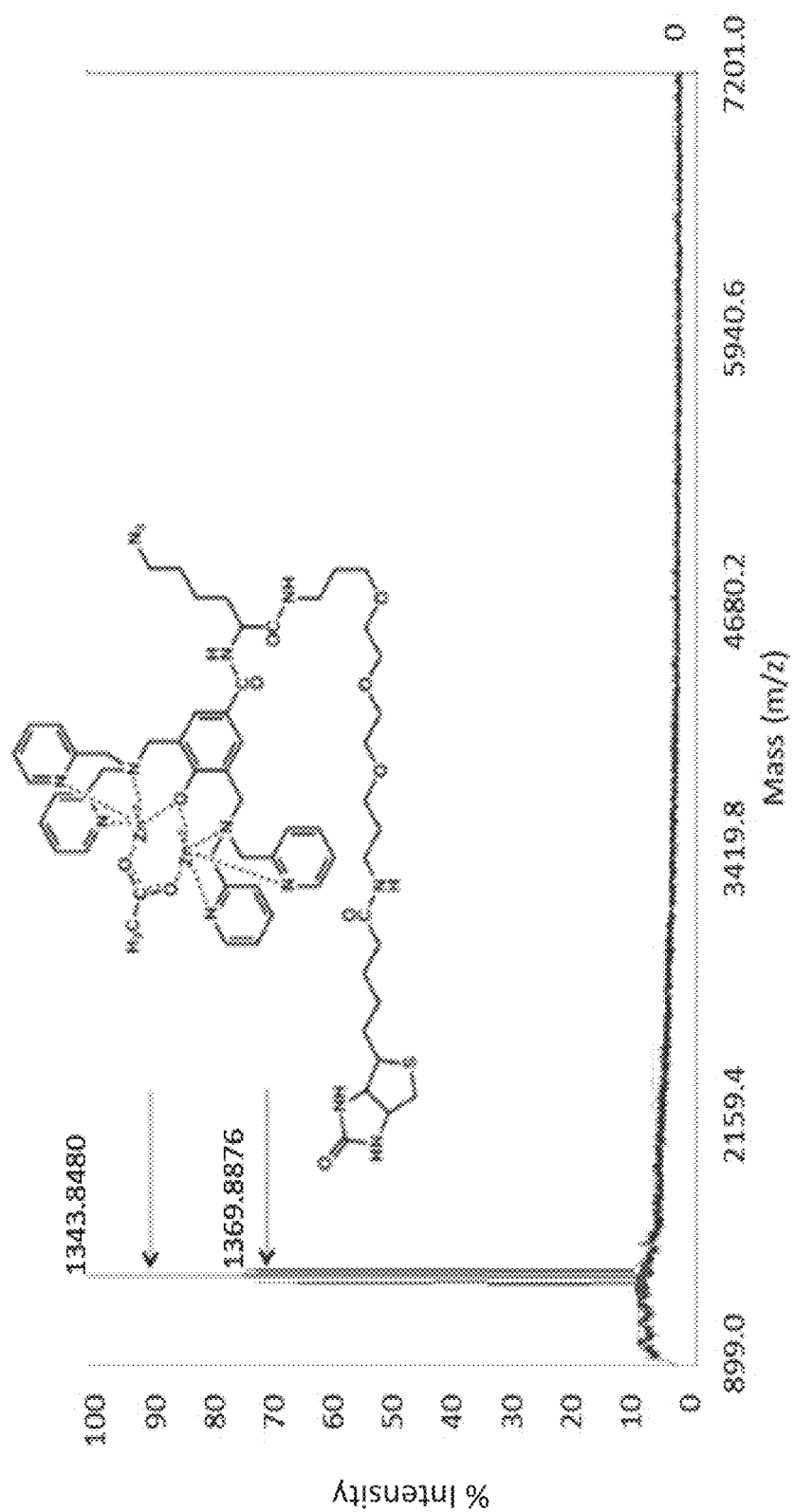
Figure 1E:
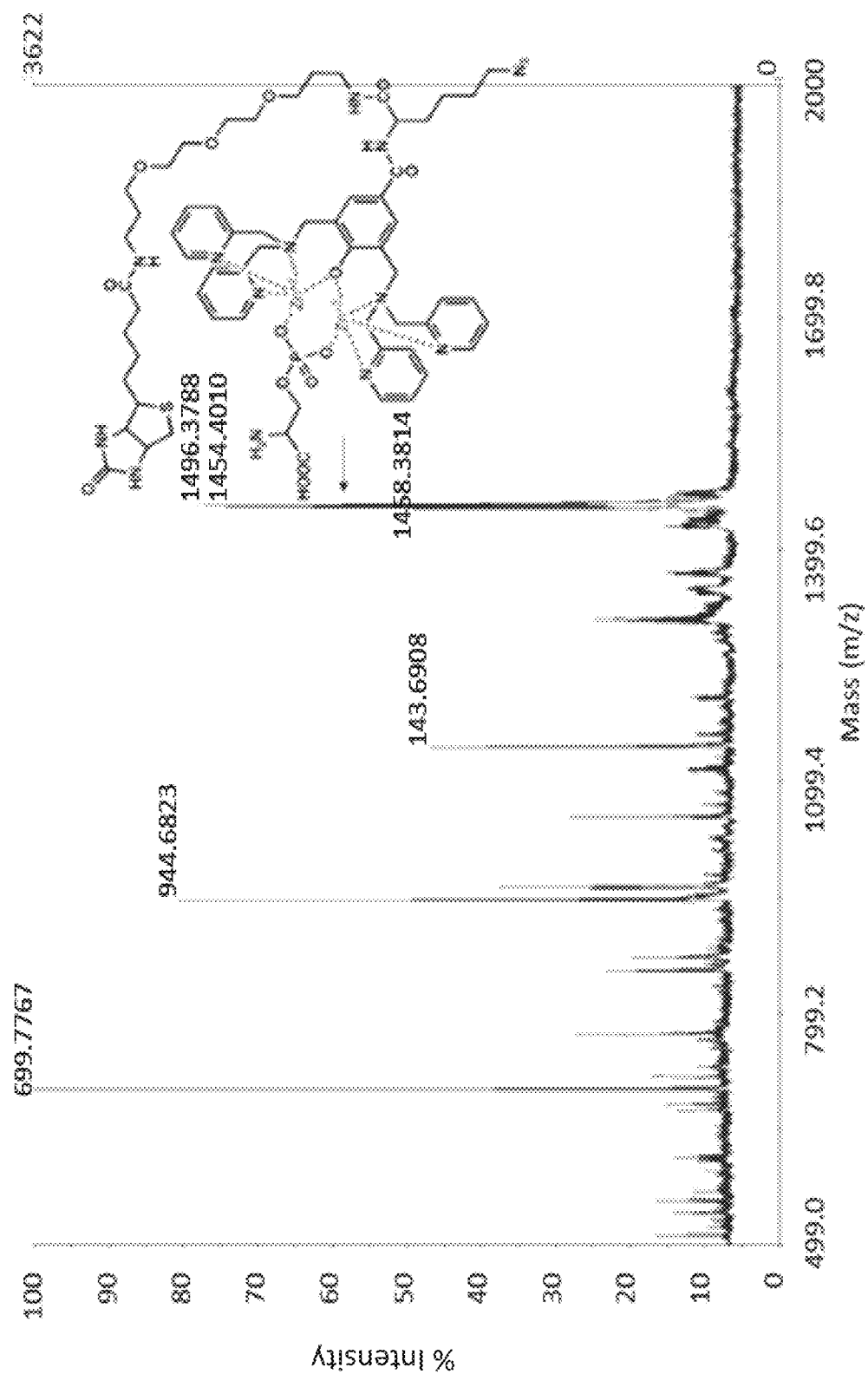
Figure 1F:
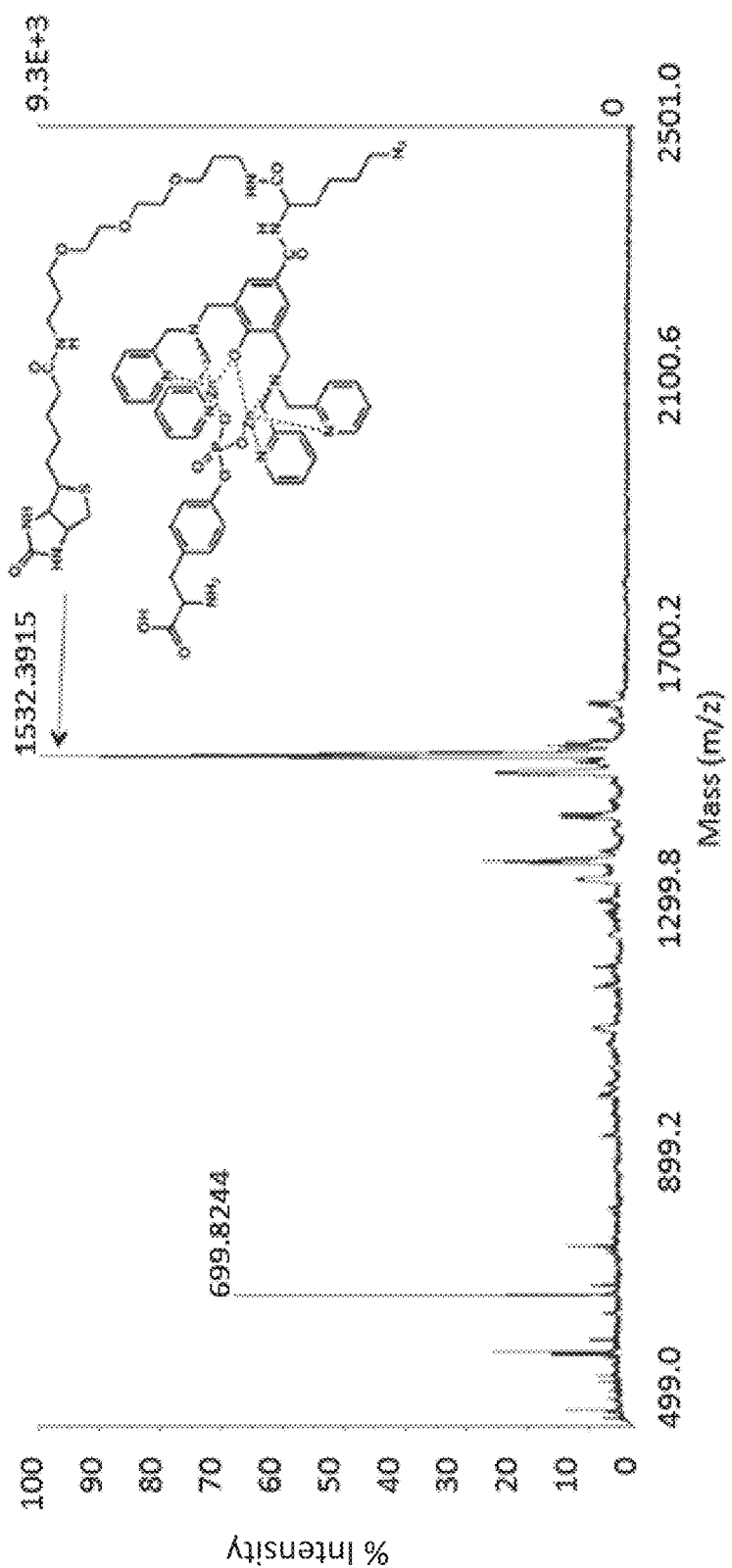
Figure 1G:
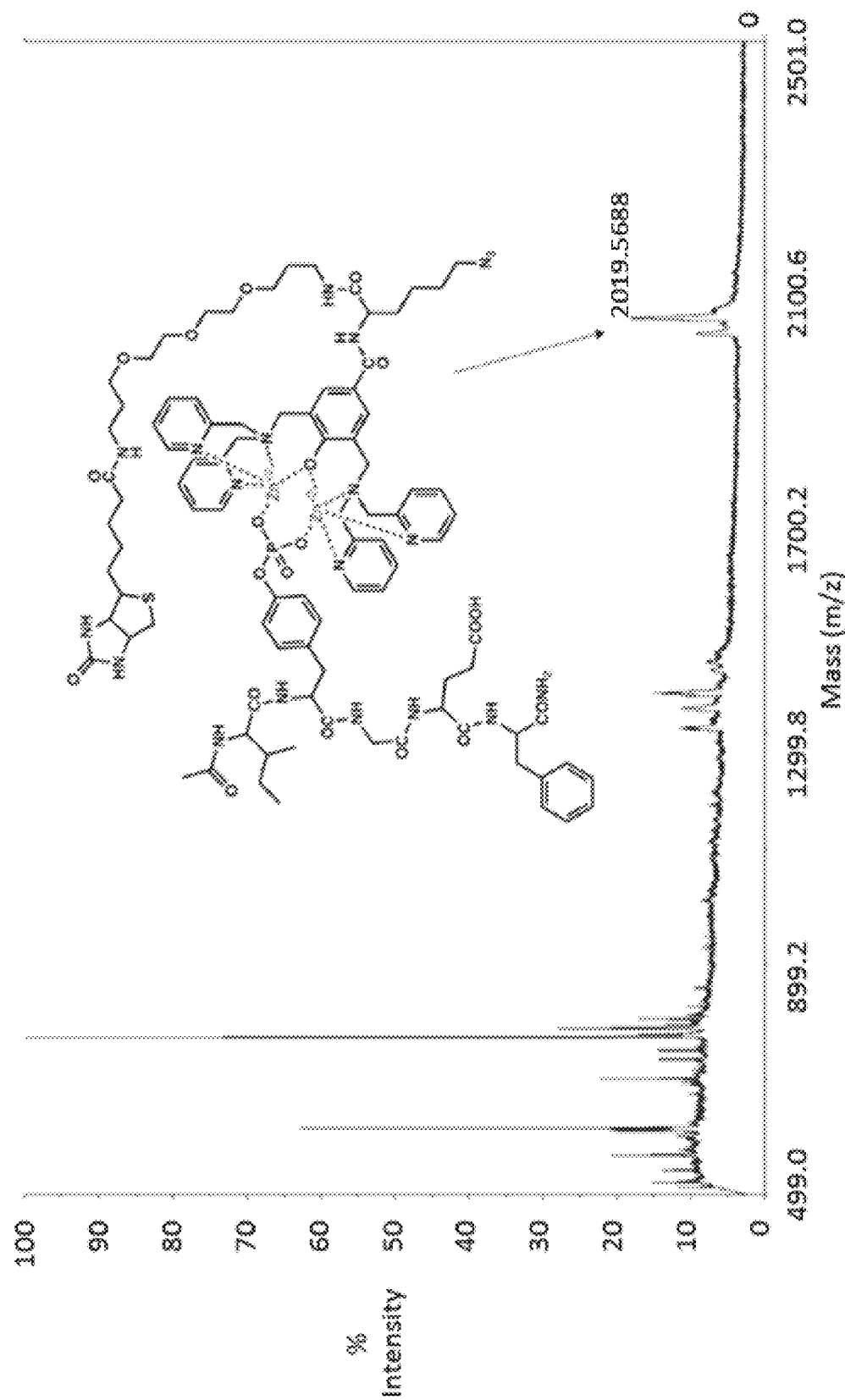
Figure 2:
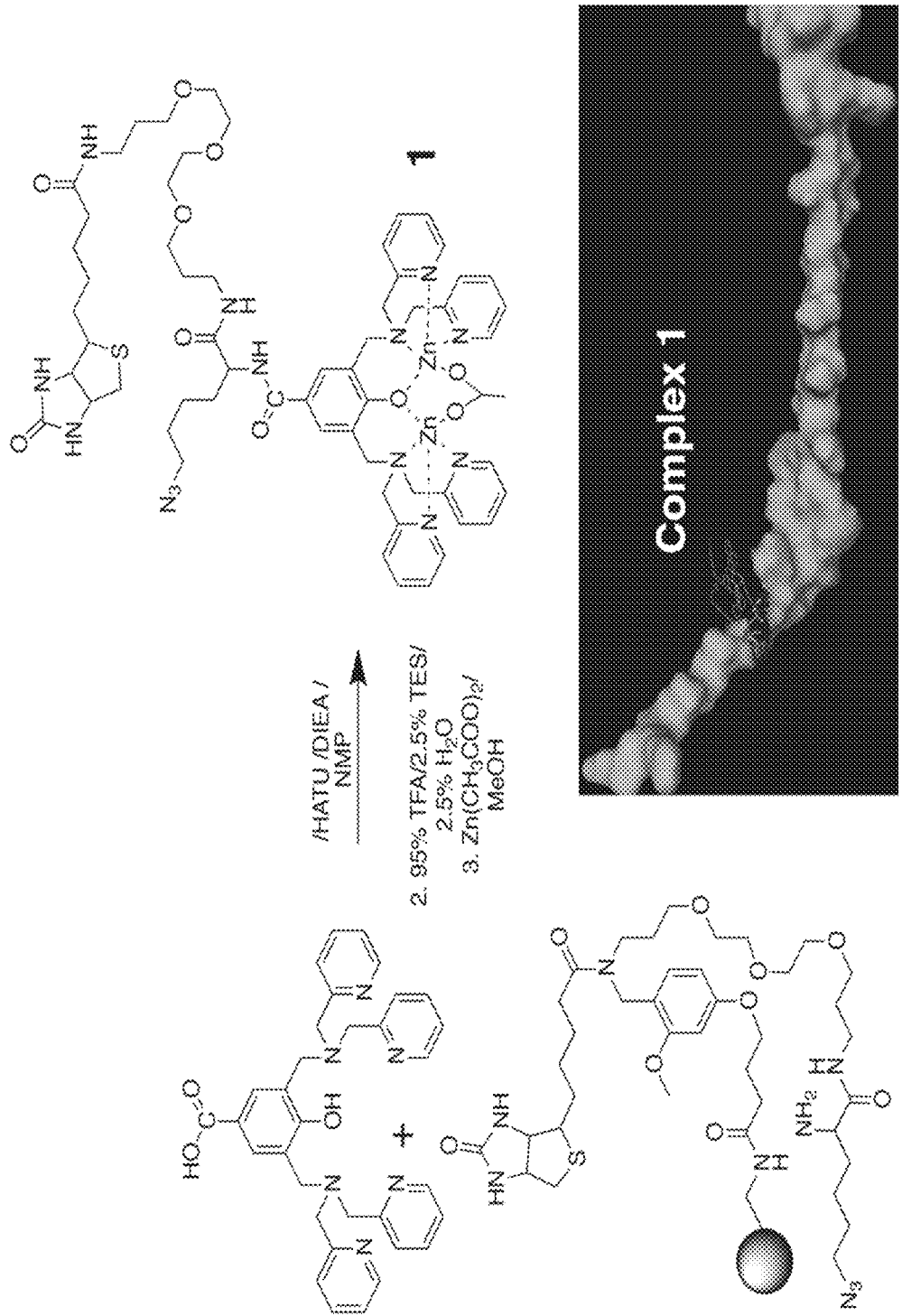
FIG. 2: The preparation of Complex-1, which is comprised of the biotin and azide-presenting divalent Zn chelator 1 bonded to the phospho-Ser474 of the 32 amino acid long peptide fragment of Akt2. The graphic of Complex-1 (bottom right; constructed using PYMOL and ChemBio3D Ultra) illustrates the scale of 1 (purple) bonded to pS474 on the polypeptide.

D,L-Fmoc-azidolysine was coupled to Biotin-PEG-NovaTag resin (coupling efficiency 0.48 mmole/g) following standard Fmoc solid phase synthesis protocol. The N$_\alpha$-Fmoc protecting group was removed by treating with 20% piperidine in NMP. Then 1.5 equivalents of 3,5-bis((bis(pyridin-2-ylmethyl)amino)methyl)-4-hydroxybenzoic acid were coupled overnight to the resin. The molecule was cleaved off the resin using a cocktail of TFA, TES and double distilled water (95:2.5:2.5), precipitated in ice cold ether and lyophilized. The crude solid was used in further synthesis. Two equivalents of zinc acetate was dissolved in methanol and added to one equivalent of 3,5-bis((bis(pyridin-2-ylmethyl)amino)methyl)-4-hydroxybenzoic acid and stirred overnight at room temperature. The solvent was removed under reduced pressure and the solid was purified using a gradient of water and acetonitrile and 0.1% TFA on the RP-HPLC (Beckman Coulter System Gold 126 Solvent Module and 168 Detector) using a C18 reversed phase semi-preparative column (Phenomenex Luna 10 µm, 250×10 mm). The calculated mass was [M]0.2H$_2$O 1369.45 and the observed mass was [M]0.2H$_2$O 1369.4 (FIG. 1D).

Example 1.7: Verification of Binding of Dizinc Complex to Phosphoamino Acids and Phosphopeptide 500 µM solution of Zn$_2$(EtL$_1$) or Zn$_2$L$_1$-Az$_4$-PEG$_2$-Biotin was made dissolving the HPLC purified solid in 10 mM tris borate buffer (TBS) (pH 8). Saturated solutions of pure phosphoserine, phosphotyrosine, Akt peptide C-terminal motif with 13 amino acids (phospho-Akt2-13mer) and pSrc substrate Ac-I-pY-GEF was made in the buffer. The Zn$_2$(EtL$_1$) or Zn$_2$L$_1$-Az$_4$-PEG$_2$-Biotin solution was added to either of the saturated solutions in a 1:1 ratio. A fresh matrix was prepared by dissolving 2,4,6-trihydroxyacetophenone (THAP) in 10 mM tris borate buffer (pH 8) with 50% acetonitrile (20 mg/ml). Each solution was mixed in a 1:1 ratio with the matrix, and subjected to Maldi TOF in a positive mode. Two controls containing only the Zn$_2$ EtL$_1$ or Zn$_2$L$_1$-Az$_4$-PEG$_2$-Biotin solution were also subjected to the Maldi TOF. In the mixed solutions, the peaks corresponding to the adduct of the dinuclear Zinc complex to the phosphoamino acid or phosphopeptides were observed (FIG. 1).

Example 2: Solid Phase Peptide Synthesis

Example 2.1: General Protocol

Peptides were synthesized on Rink Amide MBHA, Biotin Novatag, Biotin PEG Novatag and Sieber Amide resin either manually or on the Titan 357 Automatic Peptide Synthesizer (AAPPTec, Louisville, Ky.). Amino acid solutions in NMP (two equivalents), with two equivalents of HATU and 6 equivalents of DIEA were used for the amino acid coupling reaction. For removal of Na-Fmoc protecting groups, a solution of 20% piperidine in NMP was used.

Example 2.2: Acylation

The resin was treated with a solution of anhydrous acetic anhydride and 2,6-lutidine (Sigma) in NMP (acetic anhydride:2,6-lutidine:NMP; 5:6:100), twice for ten minutes at room temperature. The excess reagents were removed by five washes with NMP.

Example 2.3: Cleavage of Side Chain Protected Peptides

The peptides were synthesized on Sieber Amide resin. The resin was treated three times for one minute with 1% TFA/DCM and then washed with DCM. The peptide solution was neutralized by adding two equivalent DIEA and rotavaped. The semisolid was dissolved in filtered DMSO, HPLC grade acetonitrile and double distilled water and purified on the HPLC.

Example 2.4: Cleavage of Side Chain Deprotected Peptide

The peptides were synthesized on the Rink Amide MBHA, Biotin Novatag or Biotin PEG Novatag resin. The resin was treated with a TFA cleavage solution (TFA:TES:ddH$_2$O; 95:2.5:2.5) for two hours at room temperature. The cleavage solution was filtered through a Gooch filter crucible and added dropwise to an ice cooled solution of diethyl ether.

Example 2.5: HPLC Purification of Peptides

All the peptides were purified using a gradient of double distilled water and HPLC grade acetonitrile and 0.1% TFA on the RP-HPLC (Beckman Coulter System Gold 126 Solvent Module and 168 Detector) using a C18 reversed phase semi-preparative column (Phenomenex Luna 10 µm, 250×10 mm).

Example 2.6: Protocol for on Bead Copper (Cu) Catalyzed Azide Alkyne Cycloaddition (CuAAC) Click Reaction On bead Cu catalyzed click reactions were performed with the azide on bead and the alkyne in solution. The resin was treated with two equivalents of the relevant alkyne, 1.5 equivalents of CuI (Sigma) and 2.5 equivalents of ascorbic acid (Sigma), in a solution of 20% piperidine in NMP. The reaction was performed overnight at room temperature. The excess copper was removed from the resin by washing extensively with a Cu chelating solution (5% (w/v) sodium diethyl dithiocarbamate, 5% (v/v) DIEA in NMP).

Example 3: Peptide Library Synthesis

Randomized OBOC libraries of hexapeptides were synthesized using the Titan 357 Automated Peptide Synthesizer (AAPPTec) on 90 μm polyethylene glycol-grafted polystyrene beads (TentaGel S—NH$_2$, 0.28 mmol/g, 2.86×10$^6$ beads/g). All the libraries used unnatural D amino acids including Fmoc-D-propargylglycine. In library C, for azide incorporation, Fmoc-L-azido lysine (Anaspec) was coupled to the N termini of the on bead peptides. All the libraries contained 10% D-Methionine at the C terminal, for compatibility with Maldi-TOF/TOF sequencing. The 10% Methionine was incorporated following literature protocol.

Example 4: Synthesis and Characterization of Peptide Ligands and Intermediates Synthesis and characterization of target peptide sequence (phospho-Akt2 peptide) and C terminal 13 amino acid long phospho-peptide (phospho-Akt2-13mer): The 32mer target peptide sequence containing amino acids 450-481 of Akt2, ITPPDRYDSLGLLELDQRTHFPQF(pS)YSASIRE (SEQ ID NO:15) (phospho-Akt2 peptide), and the 13mer peptide sequence containing amino acids 469-481 of Akt2, HFPQF(pS)YSASIRE (SEQ ID NO:26) (phospho-Akt2-13mer), was synthesized on Rink Amide MBHA resin, using the Titan 357 peptide synthesizer. Fmoc-Ser(OPO$_3$Bzl)-OH (AaPPTec) was used for the incorporation of phosphoserine in the peptide. It was cleaved by TFA/TES/ddH$_2$O, precipitated in cold ether and purified using a gradient of water and acetonitrile and 0.1% TFA on the RP-HPLC. The calculated mass was 1645.67 and the observed mass was 1646.55.

Example 4.1: Mass Spectrometric Analysis of Phospho-Akt2-13Mer

Figure 6:
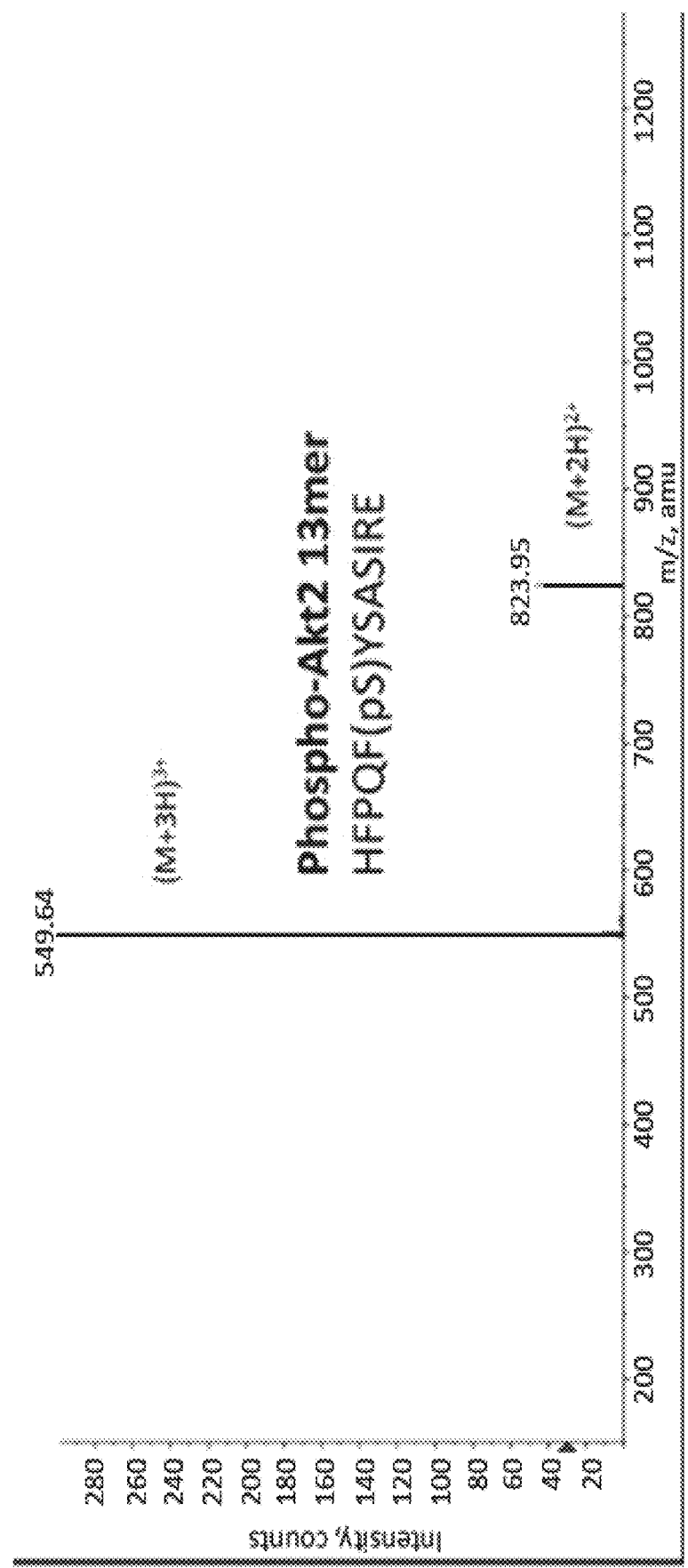
FIG. 6: Mass spectrometric analysis of phospho-Akt2-13mer.

ESI-TOF MS: m/z; 823.95 (M+2H)$^{2+}$; 549.6 (M+3H)$^{3+}$ (FIG. 6).

Example 4.2: Mass Spectrometric Analysis of Phospho-Akt2 Peptide

Figure 7:
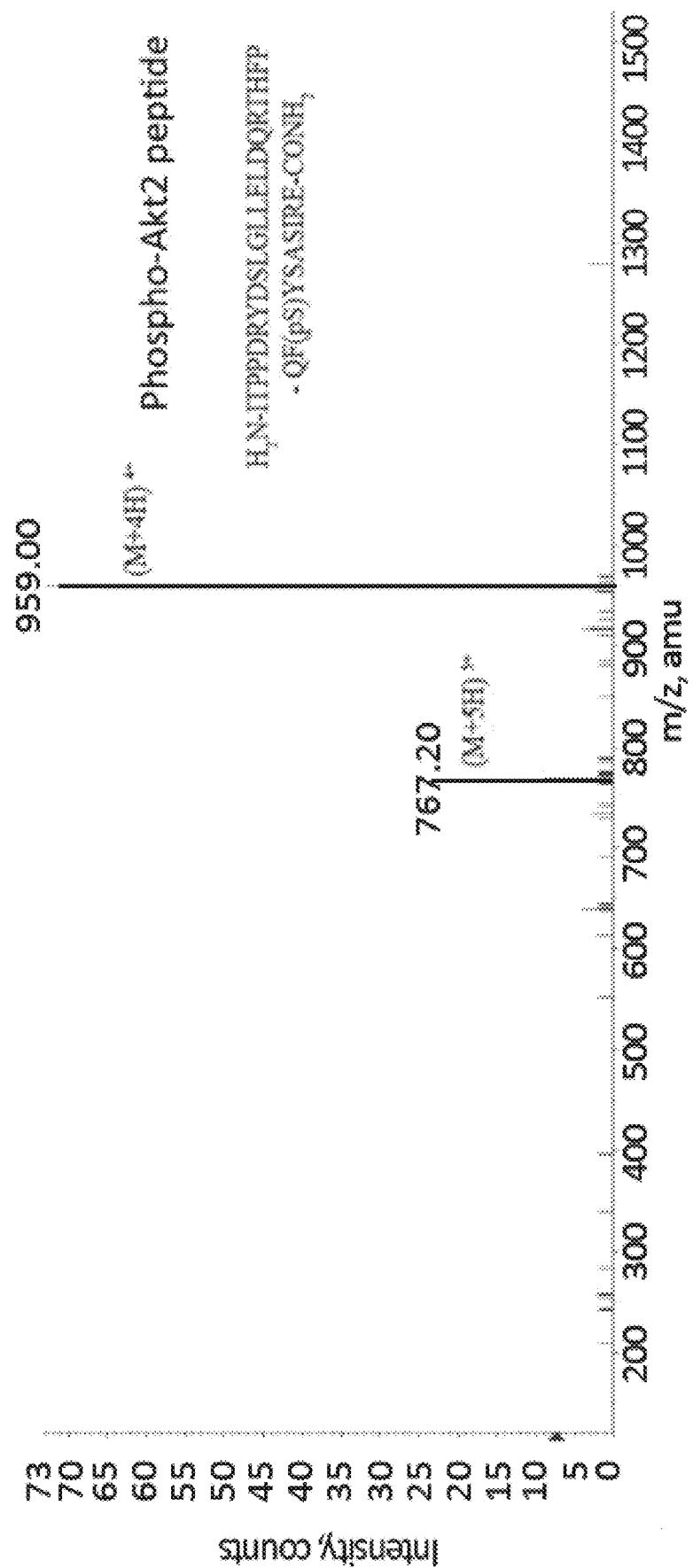
FIG. 7: Mass spectrometric analysis of phospho-Akt2 peptide.

Calculated mass: 3832.0; Observed mass: 3831.98; ESI-TOF MS: m/z; 767.2 (M+5H)$^{5+}$, 959.0 (M+4H)$^{4+}$ (FIG. 7).

Example 4.3: Synthesis and Characterization of His$_6$ Tagged Target Phospho-Akt2 Peptide (His$_6$-PEG$_2$-Phospho-Akt2) and Corresponding C Terminal Peptides from Akt1 (His$_6$-PEG$_2$-Phospho-Akt1) and Akt3 (His$_6$-PEG$_2$-Phospho-Akt3)

The target sequence, amino acids 450-481 of Akt2, with pS474, and corresponding C terminal sequences of Akt1 (449-480) and Akt3 (448-479) were synthesized on Rink Amide MBHA resin, using above mentioned procedure. Fmoc-NH-(PEG)$_2$-OH was then coupled with each peptide. Then six successive couplings were done with Fmoc-L-His(Trt)-OH. The peptides were cleaved by TFA/TES/ddH$_2$O, precipitated in cold ether and purified using a gradient of water and acetonitrile and 0.1% TFA on the RP-HPLC.

Example 4.4: His$_6$-PEG$_2$-Phospho-Akt2

Figure 8:
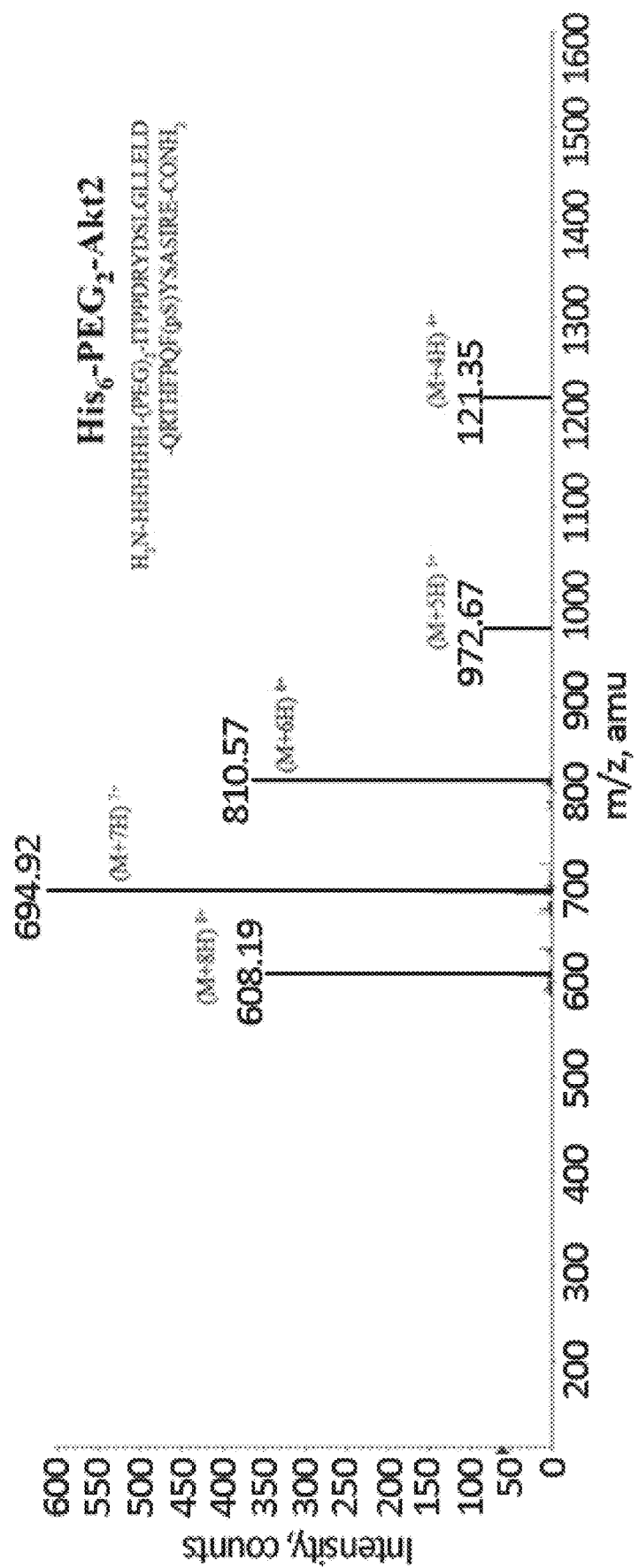
FIG. 8: Mass spectrometric analysis of $His_6$-$PEG_2$-phospho-Akt2 (SEQ ID NO:17).

Calculated mass: 4858.1; Observed mass: 4858.1; ESI-TOF MS: m/z; 608.18 (M+8H)$^{8+}$, 694.92 (M+7H)$^{7+}$, 810.57 (M+6H)$^{6+}$, 972.67 (M+5H)$^{8+}$, 1215.35 (M+4H)$^{4+}$ (FIG. 8).

Example 4.5: His$_6$-PEG$_2$-Phospho-Akt1

Figure 9:
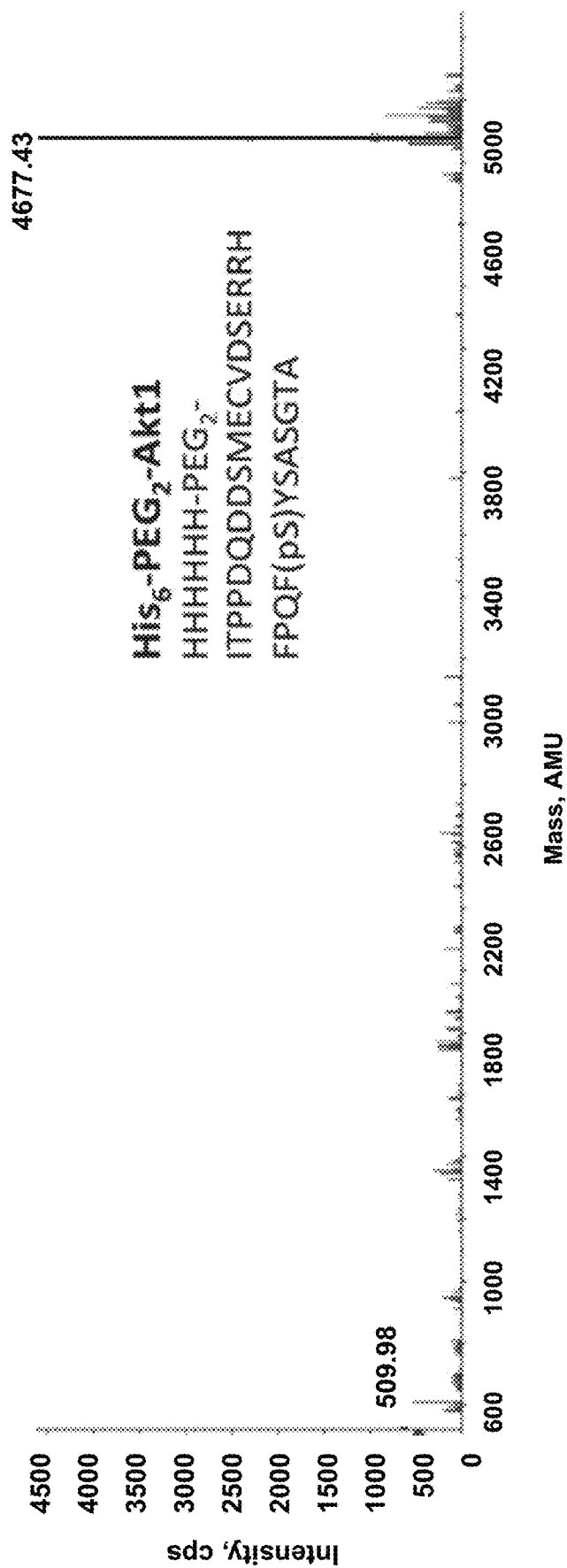
FIG. 9: Mass spectrometric analysis of $His_6$-PEG2-phospho-Akt1 (SEQ ID NO:18).

Calculated mass: Q-TOF: (M+H) 4676.8, (M+H$_2$O) 4748.8; Observed mass: (M+H) 4677.43, (M+H$_2$O) 4749.59 (FIG. 9).

Example 4.6: His$_6$-PEG$_2$-Phospho-Akt3 Peptide

Figure 10:
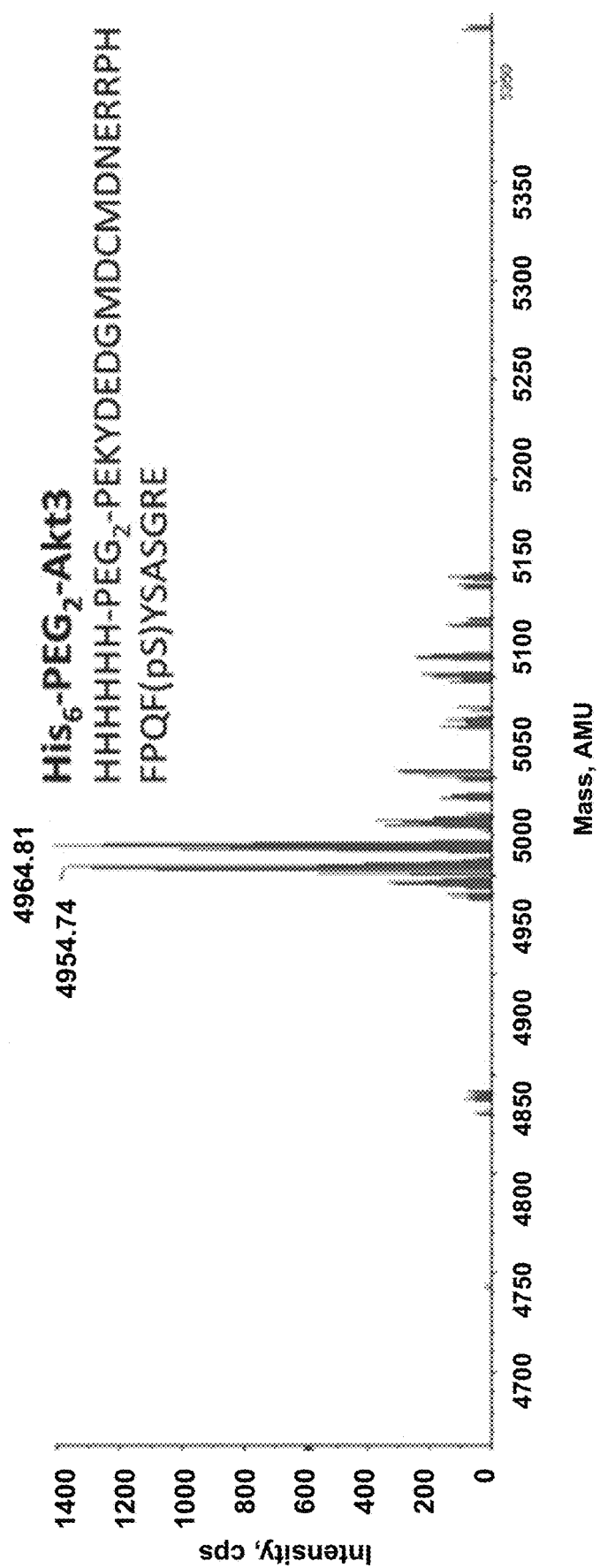
FIG. 10: Mass spectrometric analysis of $His_6$-PEG2-phospho-Akt3 peptide (SEQ ID NO:19).

Q-TOF: Calculated mass (M+K+H$_2$O) 4953.1, (M+3K) 4965.10; Observed mass: (M+K+H$_2$O) 4954.74, (M+3K) 4964.81 (FIG. 10).

Example 4.7: Synthesis and Characterization of Mono-L

Figure 11A:
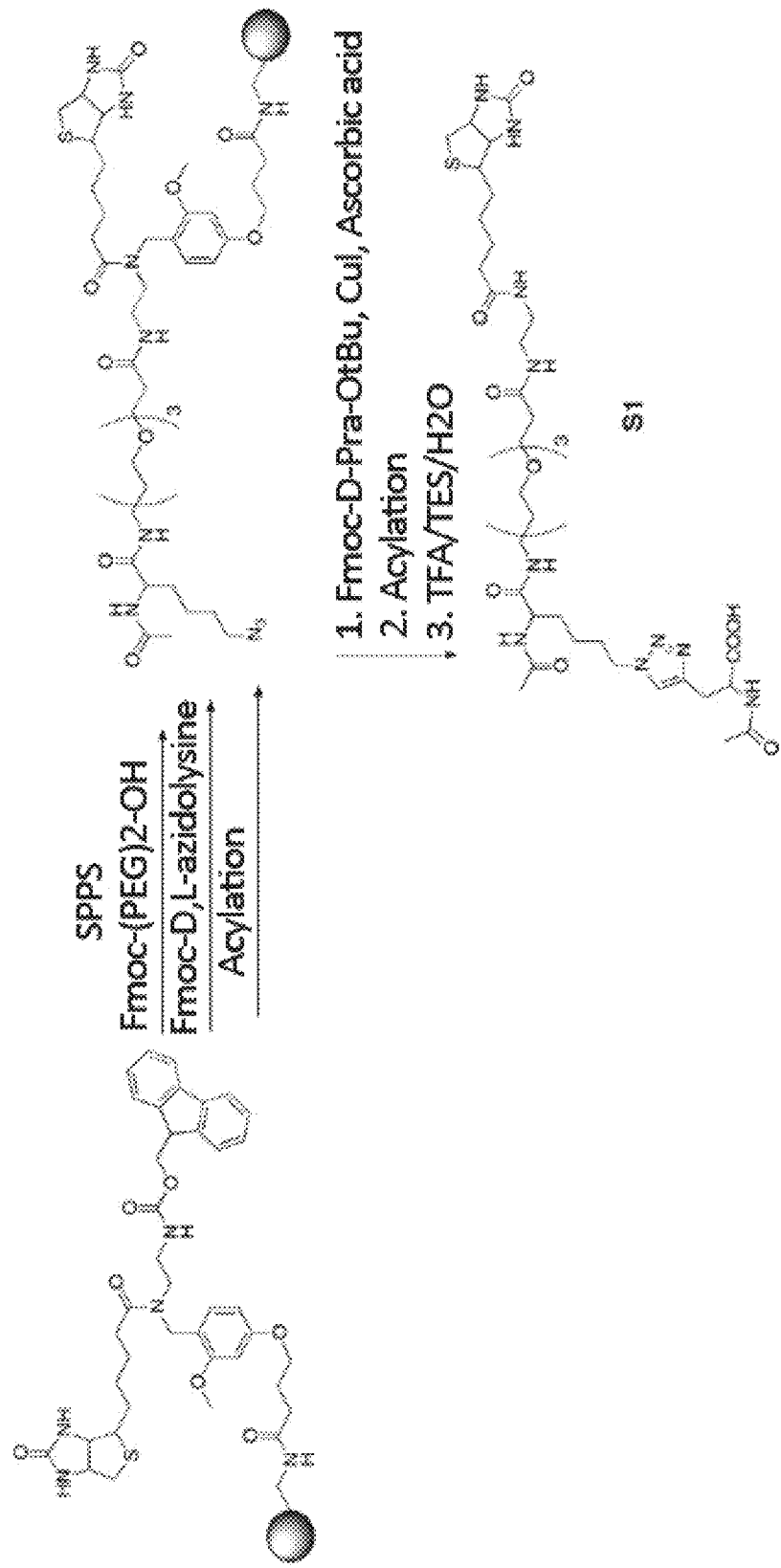
FIGS. 11A-B: The synthesis and characterization of mono-L.

Fmoc-NH-PEG$_2$-OH was coupled using standard Fmoc protocol on Biotin Novatag resin. 1.5 equivalents of D, L-Fmoc-azidolysine were coupled on the resin followed by acylation. On bead Cu catalyzed click reaction was carried out following described protocol using two equivalents of Fmoc-D-Pra-O$^t$Bu. After washes with the copper chelating solution the peptide was acylated. The resultant molecule S1 (FIG. 11A) was cleaved off the resin using TFA cleavage solution. The crude solid was used in further synthesis.

The peptide wkvkl (SEQ ID NO:2) was made on Rink Amide MBHA resin (Anaspec) following standard Fmoc SPPS synthesis protocol. 1.5 equivalents of S1 were then coupled to the peptide. After TFA cleavage the ligand mono-L was purified using a gradient of water and acetonitrile and 0.1% TFA on the RP-HPLC. The calculated mass was 1494.8 and the observed mass was 1494.6.

Example 4.7.1: Mass Spectrometric Analysis of Mono-L

Figure 11B:
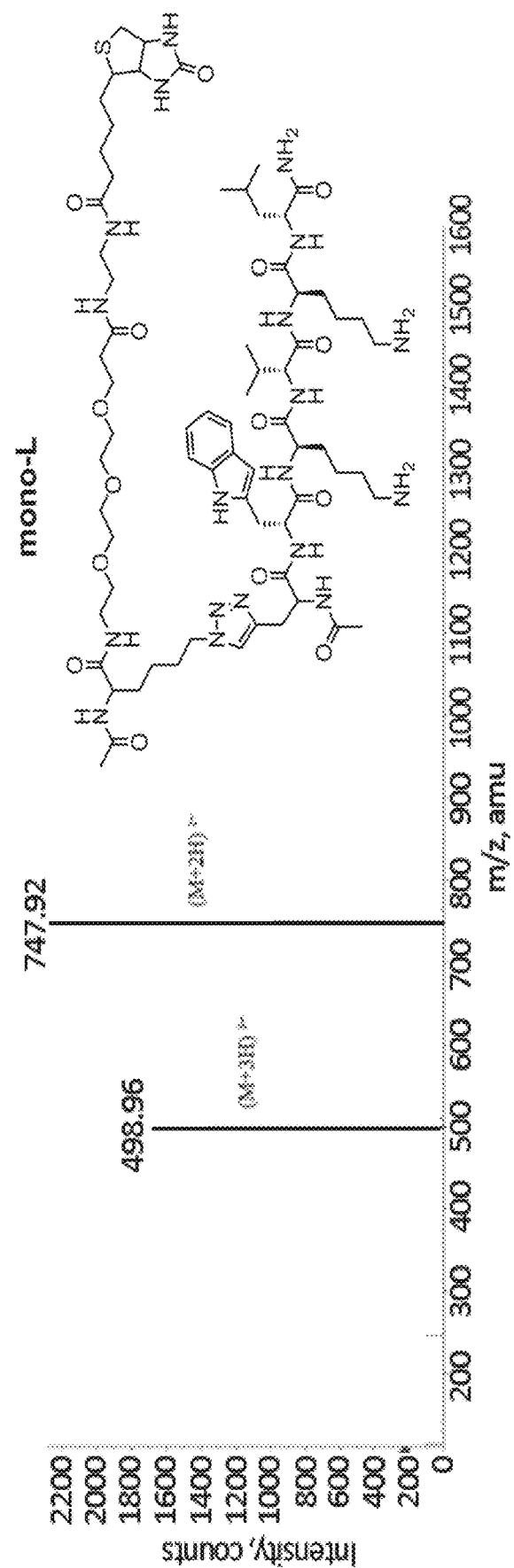

ESI-TOF MS: m/z; 498.95 (M+3H)$^{3+}$, 747.92 (M+2H)$^{2+}$ (FIG. 11B).

Example 4.8: Synthesis and Characterization of S2

Figure 12A:
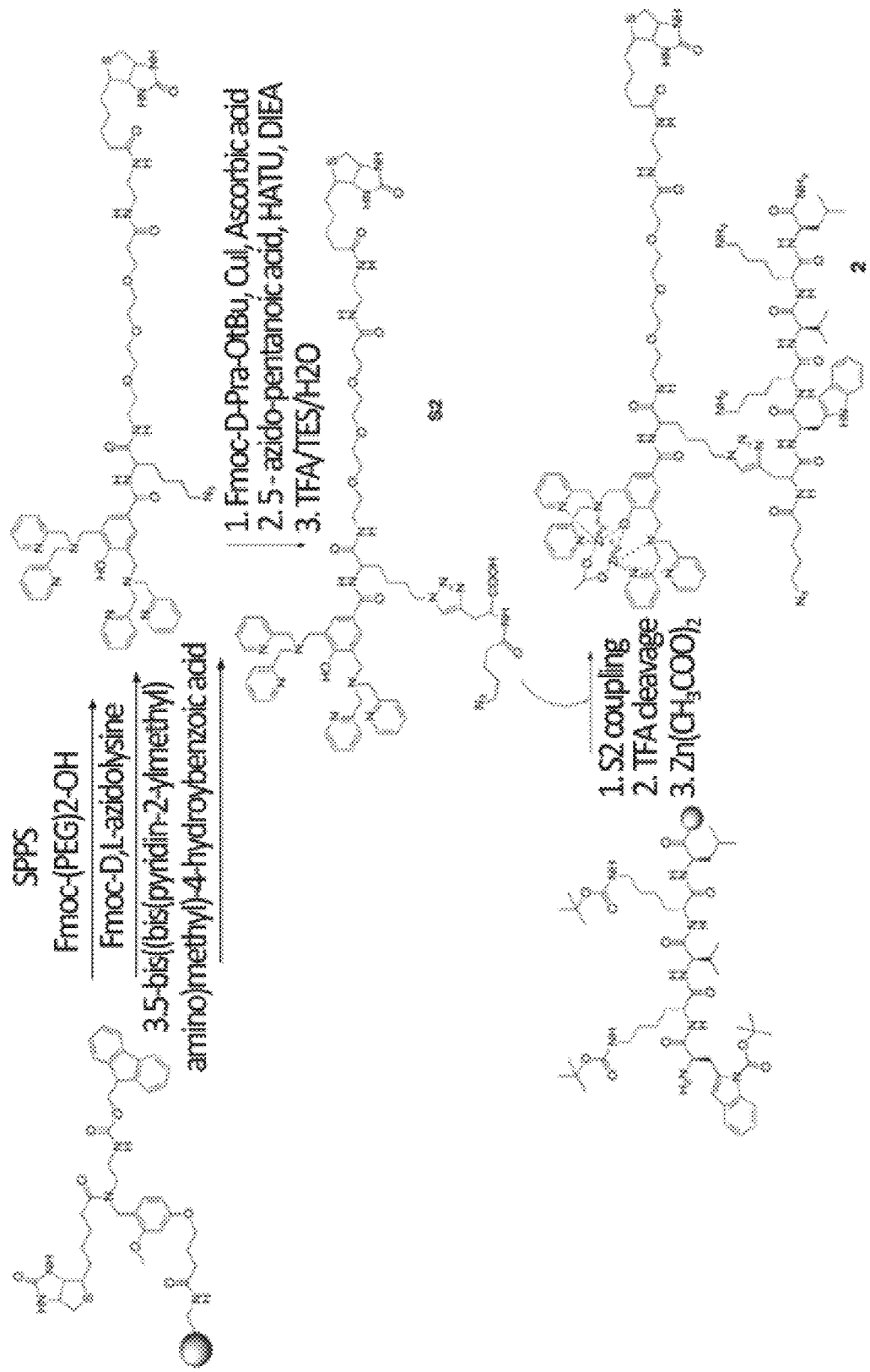
FIGS. 12A-B: The synthesis and characterization of S2.

Fmoc-NH-PEG$_2$-OH was coupled using standard Fmoc protocol on Biotin Novatag resin. 1.5 equivalent of D, L-Fmoc-azidolysine was coupled on the resin followed by coupling of 1.5 equivalent of 3,5-bis((bis(pyridin-2-ylmethyl)amino)methyl)-4-hydroxybenzoic acid. The resin was then subjected to on bead Cu catalyzed click reaction with Fmoc-D-Pra-O$^t$Bu (Fmoc-D-propargylglycine tertiary butyl ester). The excess copper was removed by washing with the copper chelating solution. 5-Azido-pentanoic acid was then coupled. The resulting peptide S2 (FIG. 12A) was TFA cleaved and lyophilized. The crude was used in further synthesis. The peptide wkvkl (SEQ ID NO:2) was made on Rink Amide MBHA resin following standard Fmoc SPPS synthesis protocol. One equivalent of peptide S2 was then coupled to the peptide. The peptide was cleaved off using TFA cleavage solution. Two equivalents of zinc acetate were dissolved in methanol and added to one equivalent of crude peptide and stirred overnight at room temperature. The solvent was removed under reduced pressure and the solid was purified using a gradient of water and acetonitrile and 0.1% TFA on the RP-HPLC. Mass calculated: [M+Na] 2291, [M+Na.TFA] 2404 Mass observed: [M+Na] 2289.98, [M+Na.TFA] 2403.95

Example 4.8.1: Mass Spectrometric Analysis of S2

Figure 12B:
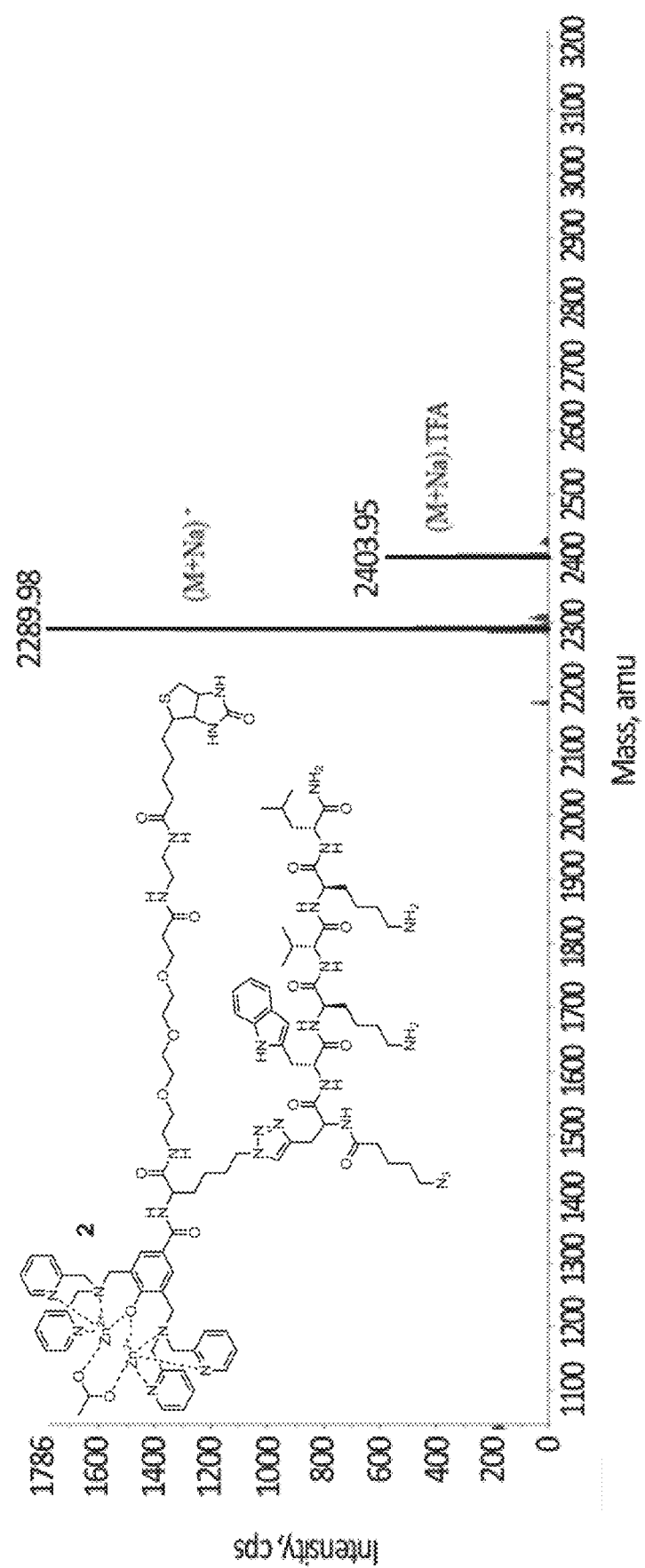

Mass calculated: [M+Na]+2291, [M+Na.TFA]$^{+1}$ 2404 Mass observed: [M+Na]$^+$ 2289.98, [M+Na.TFA]$^{+1}$ 2403.95 (FIG. 12B).

Example 4.9: Synthesis and Characterization of Bi-L

Figure 13A:
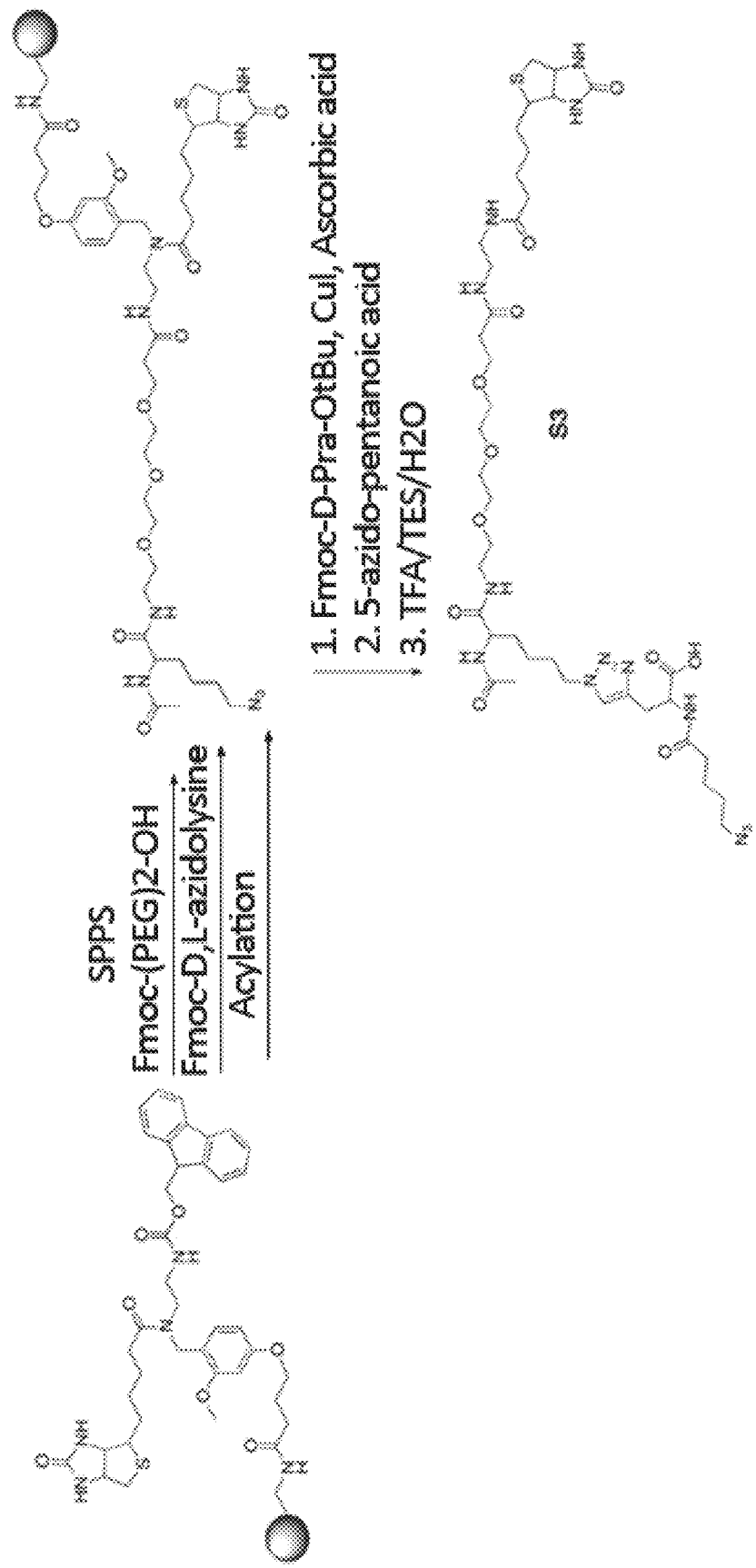

Fmoc-NH-PEG$_2$-OH was coupled using standard Fmoc protocol on Biotin Novatag resin. 1.5 equivalent of D,L-Fmoc-azidolysine was coupled on the resin followed by acylation of the amine terminal. On bead click reaction was carried out with two equivalents of Fmoc-D-Pra-O$^t$Bu. After washes with copper removing solution, 5-azido-pentanoic acid was coupled. After TFA cleavage the resultant molecule S3 (FIG. 13A) was lyophilized and the crude solid was used in further synthesis. The peptide wkvkl (SEQ ID NO:2) was made on Rink Amide MBHA resin (Anaspec) following standard Fmoc SPPS synthesis protocol. One equivalent of S3 was then coupled to the peptide on bead. Fmoc-D-Pra-O$^t$Bu was then clicked to the azido functionality on bead. After washes with the copper chelating solution, the peptide was further extended to hnGyf (SEQ ID NO:7) on the N terminal using standard Fmoc SPPS synthesis. After TFA cleavage the biligand was purified using a gradient of water and acetonitrile and 0.1% TFA on the RP-HPLC. Mass calculated: 2309.7 Mass observed: 2309.4.

Example 4.9.1: Mass Spectrometric Analysis of Bi-L

ESI-TOF MS: m/z; 770.44 (M+3H)$^{3+}$, 578.33 (M+4H)$^{4+}$ (FIG. 13B).

Example 4.10: Synthesis and Characterization of Anchor-3N

Figure 14A:
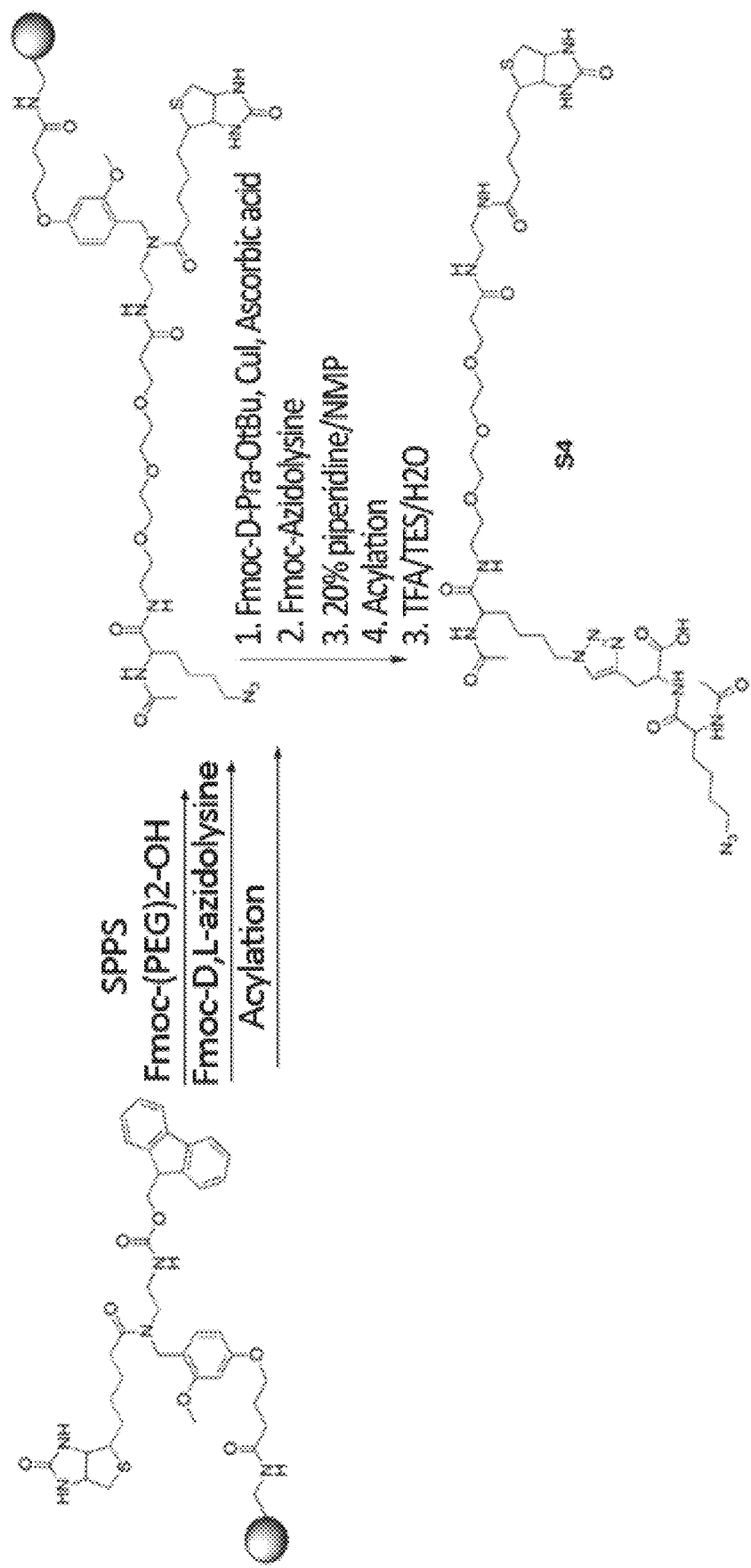
FIGS. 14A-B: The synthesis and characterization of Anchor-3N.

Fmoc-NH-PEG$_2$-OH was coupled using standard Fmoc proteocol on Biotin Novatag resin. 1.5 equivalent of D, L-Fmoc-azidolysine was coupled on the resin followed by acylation using acetic anhydride and 2,6-lutidine in DMF. On bead click reaction with Fmoc-D-Pra-O$^t$Bu was carried out. After washes with copper chelating solution Fmoc-L-azidolysine was coupled. Following removal of the Fmoc protecting group, the amine terminal was acylated. After TFA cleavage the resultant molecule S4 (FIG. 14A) was lyophilized and the crude solid was used in further synthesis. The peptide wkvkl (SEQ ID NO:2) was made on Rink Amide MBHA resin. 1.5 equivalents of S4 were then coupled to the peptide. On bead click reaction was carried out with two equivalents of Fmoc-D-Pra-O$^t$Bu. After washes with copper removing solution, the peptide was further extended to hnGyf (SEQ ID NO:7) on the N terminal using standard Fmoc SPPS synthesis. Fmoc-L-azidolysine was then coupled, followed by acylation of the amine terminal. After TFA cleavage Anchor-3N was purified using a gradient of water and acetonitrile and 0.1% TFA on the RP-HPLC. Mass calculated: 2534.9 Mass observed: 2534.6.

Example 4.10.1: Mass Spectrometric Analysis of Anchor-3N

Figure 14B:
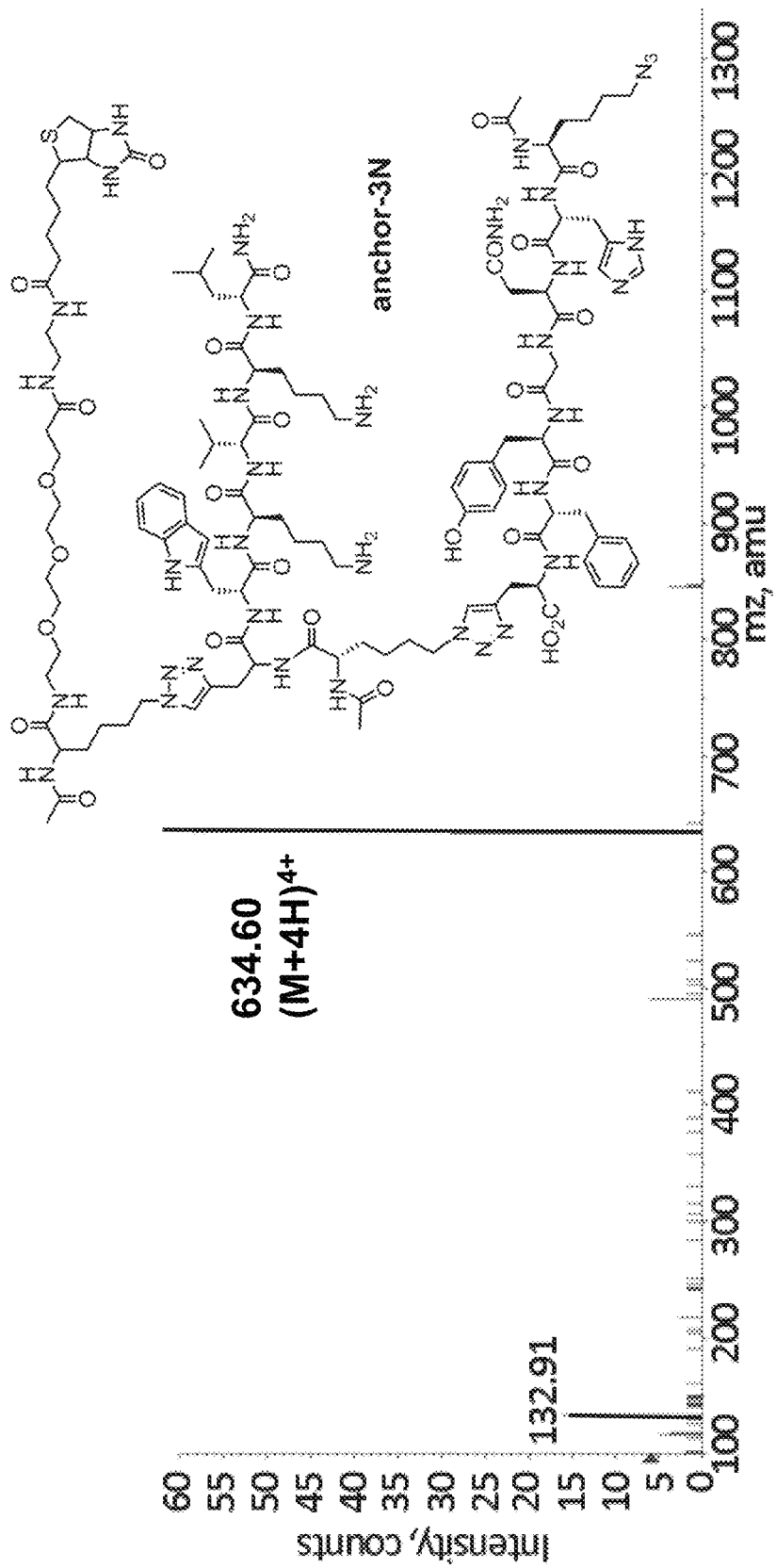

ESI-TOF MS: m/z; 634.60 (M+4H)$^{4+}$ (FIG. 14B).

Example 4.11: Synthesis and Characterization of Anchor-3C

The peptide NH$_2$-wkvkk (Alloc) (SEQ ID NO:29) was made on Rink Amide MBHA resin following standard Fmoc SPPS synthesis protocol. one equivalent of S3 (FIG. 13A) was then coupled to the resin. On bead click reaction was carried out overnight using 1.5 equivalents of Fmoc-D-Pra-O$^t$Bu. After washes with the copper chelating solution, the peptide was further extended to hnGyf on the N terminal using standard Fmoc SPPS synthesis. Then it was acylated again. The alloc side chain of Fmoc-D-lysine(Alloc)-OH was deprotected using standard alloc deprotection technique. Then 4-pentynoic acid was coupled. After TFA cleavage, Anchor-3C was purified using a gradient of water and acetonitrile and 0.1% TFA on the RP-HPLC.

Mass calculated: 2446.8; Mass observed: 2446.5

Example 4.11.1: Mass Spectrometric Analysis of Anchor-3C

Figure 15:
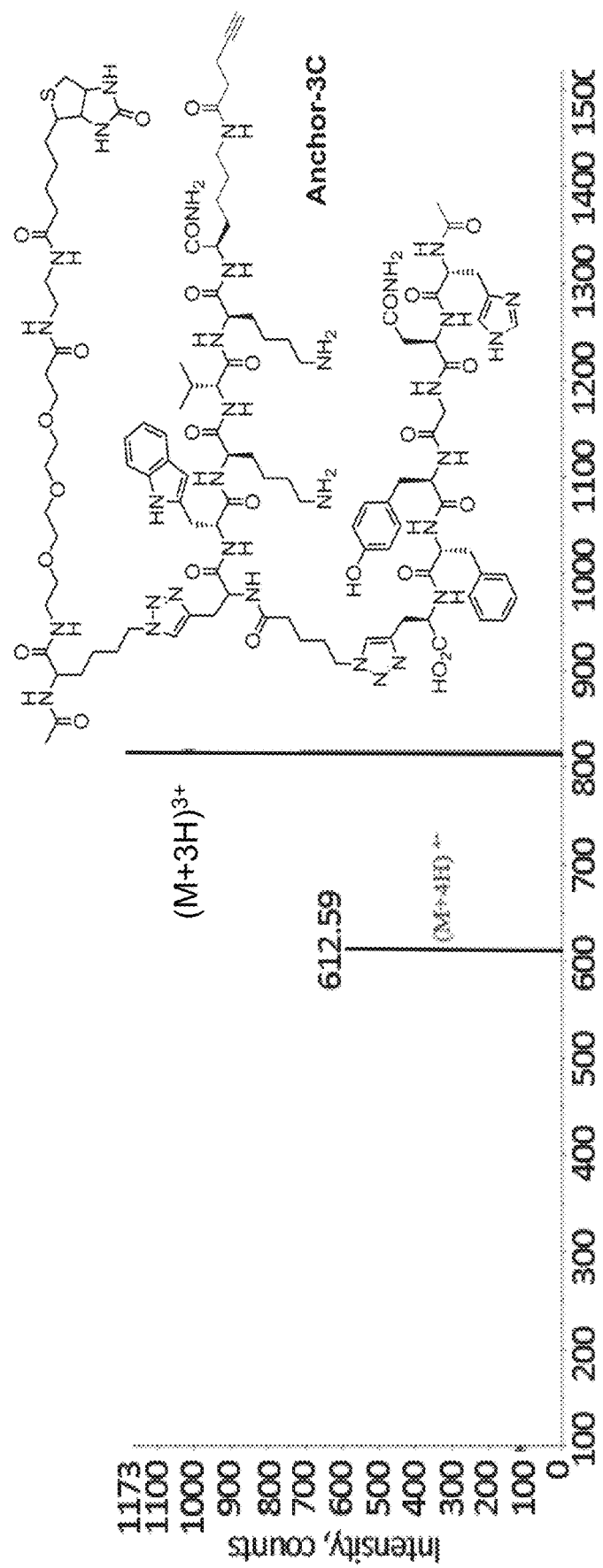
FIG. 15: Mass spectrometric analysis of Anchor-3C.

ESI-TOF MS: m/z; 816.11 (M+3H)$^{3+}$, 612.59 (M+4H)$^{4+}$ (FIG. 15).

Example 4.12: Synthesis and Characterization of N-tL

Side chain protected version of Ac-(D-Pra)-yyrfG-CONH$_2$ (SEQ ID NO:30) was made on Amide Sieber resin. The protected peptide was cleaved off using 1% TFA in DCM and purified using a gradient of water and acetonitrile and 0.1% TFA on the RP-HPLC. Anchor-3N was made on resin as described and then acylated using standard acylation method. On bead click reaction was carried out for the bead bound Anchor-3N with two equivalents of side chain protected purified peptide Ac-(D-Pra)-yyrfG-CONH$_2$ (SEQ ID NO:30). The resin was washed with copper chelating solution. The peptide was cleaved off the resin with the TFA cleavage solution and purified using a gradient of water and acetonitrile and 0.1% TFA on the RP-HPLC.

Mass calculated: 3417.9 Mass observed: 3417.5.

Example 4.12.1: Mass Spectrometric Analysis of N-tL

Figure 16:
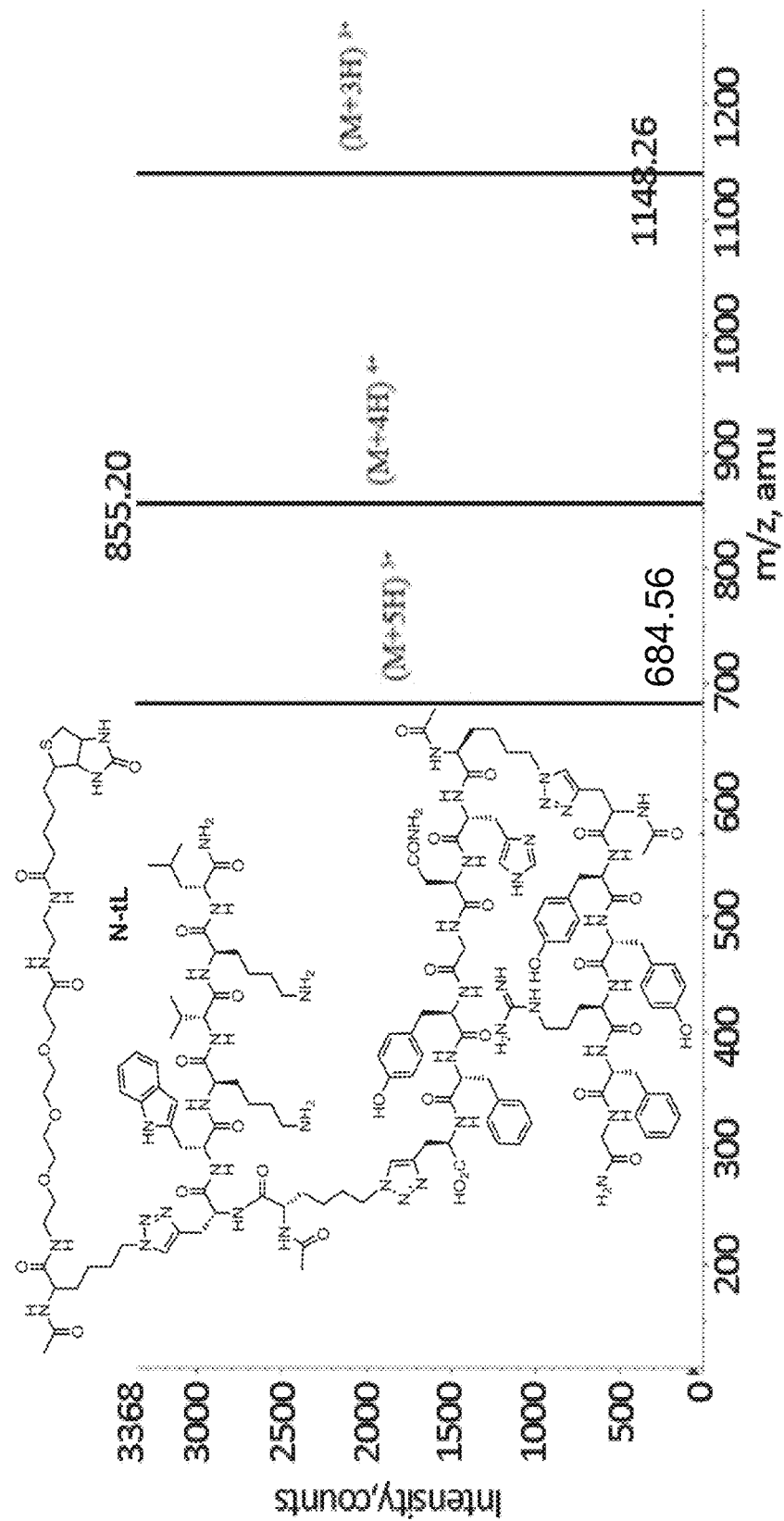
FIG. 16: Mass spectrometric analysis of N-tL.

ESI-TOF MS: m/z; 684.56 (M+5H)$^{5+}$, 855.20 (M+4H)$^{4+}$, 1140.26 (M+3H)$^{3+}$ (FIG. 16).

Example 4.13: Synthesis of D-Lys (Pentyne) Amide

Boc-D-Lys(Fmoc)-OH was coupled with rink amide resin. Then 4-pentynoic acid was coupled with it, after standard piperidine deprotection. The dried resin was cleaved with TFA cocktail and purified using a gradient of water and acetonitrile and 0.1% TFA on the prep-HPLC. Mass calculated: (M+H) 225 Mass observed: 226.

Example 4.14: Synthesis and Characterization of C-tL

Ac-(L-Az4)-hdGGf (SEQ ID NO:31) (Az4=azidolysine) was made on Rink Amide MBHA resin. On bead click reaction of the peptide on resin with D-Lys(pentyne) amide was carried out overnight at room temperature with two equivalents of D-Lys(pentyne) amide. The resin was washed with the copper chelating solution and further extended to wkvk (SEQ ID NO:1) on the N terminal using standard Fmoc SPPS synthesis. Then, 1.5 equivalent of S3 was coupled to the peptide. An on bead click reaction was carried out with Fmoc-D-Pra-O$^t$Bu. After washes with copper chelating solution, the peptide was further extended to hnGyf (SEQ ID NO:7) on the N terminal using standard Fmoc SPPS synthesis. The dried resin was cleaved with TFA cleavage solution and purified using a gradient of water and acetonitrile and 0.1% TFA on the RP-HPLC. Mass calculated: 3199.65; Mass observed: 3198.44.

Example 4.14.1: Mass Spectrometric Analysis of C-tL

Figure 17:
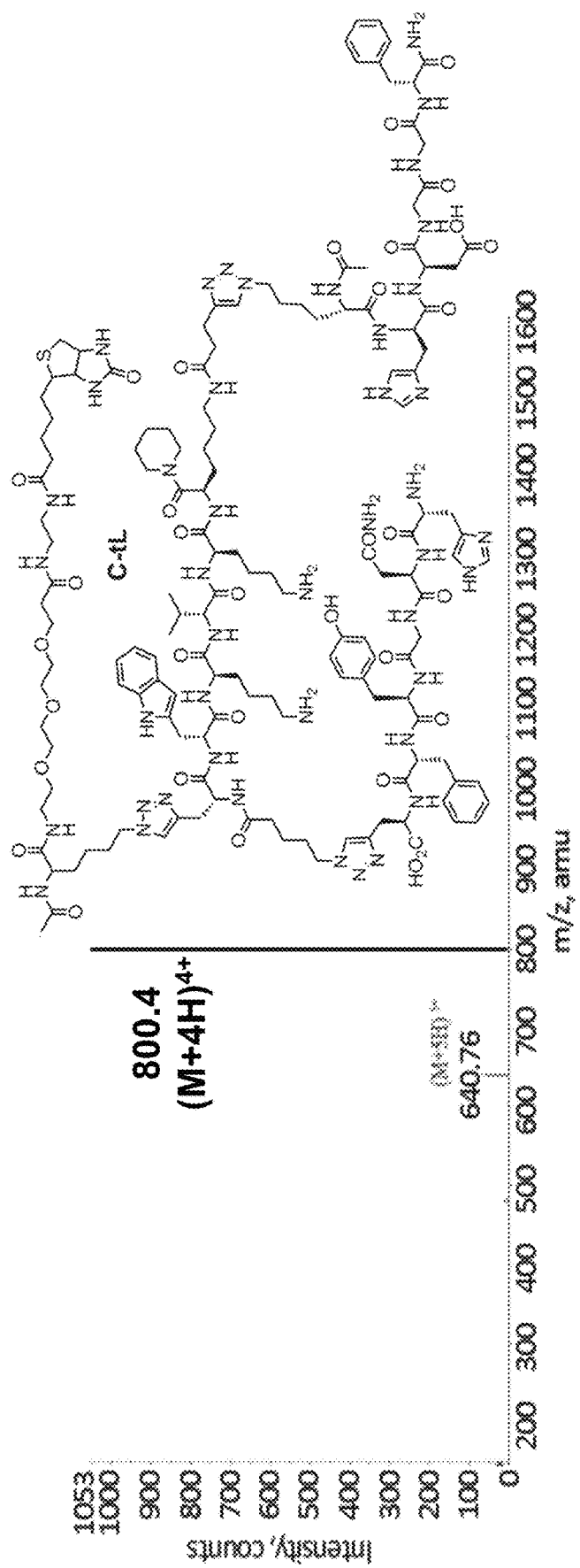
FIG. 17: Mass spectrometric analysis of C-tL.

ESI-TOF MS: m/z; 640.76 $(M+5H)^{5+}$, 800.45 $(M+4H)^{4+}$ (FIG. 17).

Example 5: Screening with One Bead One Compound (OBOC) Peptide Library

Example 5.1: Screen for Mono-L 50 nM solution of the Akt2 peptide was made by diluting 0.5 mg/mi DMSO stock in 25 mM tris chloride, 150 mM NaCl, 2 mM KCl, pH 8) (TBS). 100 µM solution of the Zn$_2$L-Az$_4$-PEG$_2$-Biotin was added to the 50 nM solution of the phospho-Akt2 peptide and shaken overnight at room temperature. Before the addition to the OBOC library, Bovine Serum Albumin (BSA) and Tween 20 was added to the solution to make the final concentrations 0.1% BSA and 0.05% tween 20 in the buffer. 250 mgs of library A (D-Pra-XXXXX-10% M-TG, Table 1) (SEQ ID NO:32) were used in the screen. The beads were equilibrated in 0.1% BSA, 0.05% Tween 20/TBS (binding buffer) by shaking for 8 hours. The Zn$_2$L-Az$_4$-PEG$_2$-Biotin-Akt2 peptide solution was added to the swelled beads and shaken overnight at room temperature. The beads were washed three times with the binding buffer. A 1:10,000 dilution of mouse anti biotin monoclonal antibody-Alkaline Phosphatase conjugate (Sigma) in binding buffer was added to the beads. The beads were then washed thrice with binding buffer, thrice with TBST (0.05% tween 20/TBS) and thrice with TBS.

A BCIP solution was freshly prepared by adding 33 µl of BCIP (50 mg/ml) stock solution in 10 ml of Alkaline Phosphatase buffer (100 mM Tris-HCl, pH 9.0, 150 mM NaCl, 1 mM MgCl$_2$) (Promega). The beads were washed once with the Alkaline Phosphatase buffer, and then treated with the fresh BCIP solution. The hit beads turned turquoise blue due to a colorimetric reaction of Alkaline Phosphatase with BCIP. The reaction was quenched after one hour with 0.1 N HCl. The hit beads were picked with a pipette tip and transferred to an eppendorf tube. The turquoise color of the hit beads was removed by washing with DMF. The proteins on the beads were stripped by washes with 7.5 M guanidium hydrochloride pH 2.0 solution. Then beads were then equilibrated in buffer. The screen was repeated on this small set of beads, this time using a preincubated mixture of 2.5 mM biotin and 1:10,000 dilution of a mouse anti biotin monoclonal-Alkaline Phosphatase conjugate (Sigma) as the secondary antibody. On addition of the BCIP, the true hits, due to competition with biotin, remain clear. The clear beads were manually picked, washed with guanidium hydrochloride and water, and sequenced using the Edman Peptide Sequencer.

Example 5.2: Screen for Bi-L

Example 5.2.1: Prescreen 2 batches of 135 mg of library B (XXXXX-D-Pra-10% M-TG, Table 1) (SEQ ID NO:33) were washed in water, and swelled overnight in binding buffer (25 mM Tris-Cl (pH=7.7), 150 mM NaCl, 2 mM KCl, 0.1% (v/v) Tween-20, and 0.1% BSA). 20 µM and 50 µM solutions of 2 (FIG. 18B) was added to the beads and shaken for 10 hours at room temperature. The beads were washed thrice, for fifteen minutes each, with the binding buffer. A 1:10,000 dilution of mouse anti biotin antibody-Alkaline Phosphatase conjugate (Sigma) in binding buffer was added to the beads. The beads were washed three times, for fifteen minutes each, with wash buffer 1 (25 mM Tris-Cl (pH=7.7), 150 mM NaCl, 2 mM KCl, 0.1% (v/v) Tween-20), followed by three fifteen minute washes with wash buffer 2 (25 mM Tris-Cl (pH=7.7), 150 mM NaCl, 2 mM KCl). The beads were then developed in BCIP solution for 35 minutes and quenched with 0.1 N HCl. The blue hit beads, which were background binders to the mono-L-Zn chelator or the detection antibody were picked up manually. The clear beads were stringently washed with DMF, 7.5 mM guanidium hydrochloride, pH 2.0, and double distilled water.

Example 5.2.2: Product Screen

The washed beads from each prescreen were dried and swelled overnight in binding in 8 ml fritted polypropylene

TABLE 1

OBOC peptide libraries used in screens.

| Formula | Components | Unique sequences | Fraction Screened |
|---|---|---|---|
| Library A: D-Pra-XXXXX-10% M-TG | SEQ ID NO:32 X = 18 D amino acids except D-Met and D-Cys | 1,889,568 | 40% for 1 ligand screen 80% for 3 ligand screen for N-tL |
| Library B: XXXXX-D-Pra-10% M-TG | SEQ ID NO:33 X = 18 D amino acids except D-Met and D-Cys | 1,889,568 | 40% for 2 ligands |
| Library C: L-Az4-XXXXX-10% M-TG | SEQ ID NO:34 X = 18 D amino acids except D-Met and D-Cys | 1,889,568 | 80% for 3 ligand screen for C-tL | solid-phase synthesis tubes. In two separate eppendorf tubes, 20 µM and 50 µM solution of 2 was incubated overnight at room temperature with 10 nM and 25 nM phospho-Akt2 peptide solution respectively, in binding buffer. 4 mL of each of the two solutions were added to a precleared swelled bead batch and the tubes were shaken at room temperature for ten hours. The beads were washed three times, for fifteen minutes each, with wash buffer 1 followed by three fifteen minute washes with wash buffer 2. The beads are then developed in BCIP solution for thirty-five minutes and quenched with 0.1 N HCl. The blue hit beads were picked up manually, stringently washed with DMF, guanidium hydrochloride and water, and sequenced on the Edman Sequencer. The sequences from the biligand screen are given in Tables 2 and 3.

Figure 19:
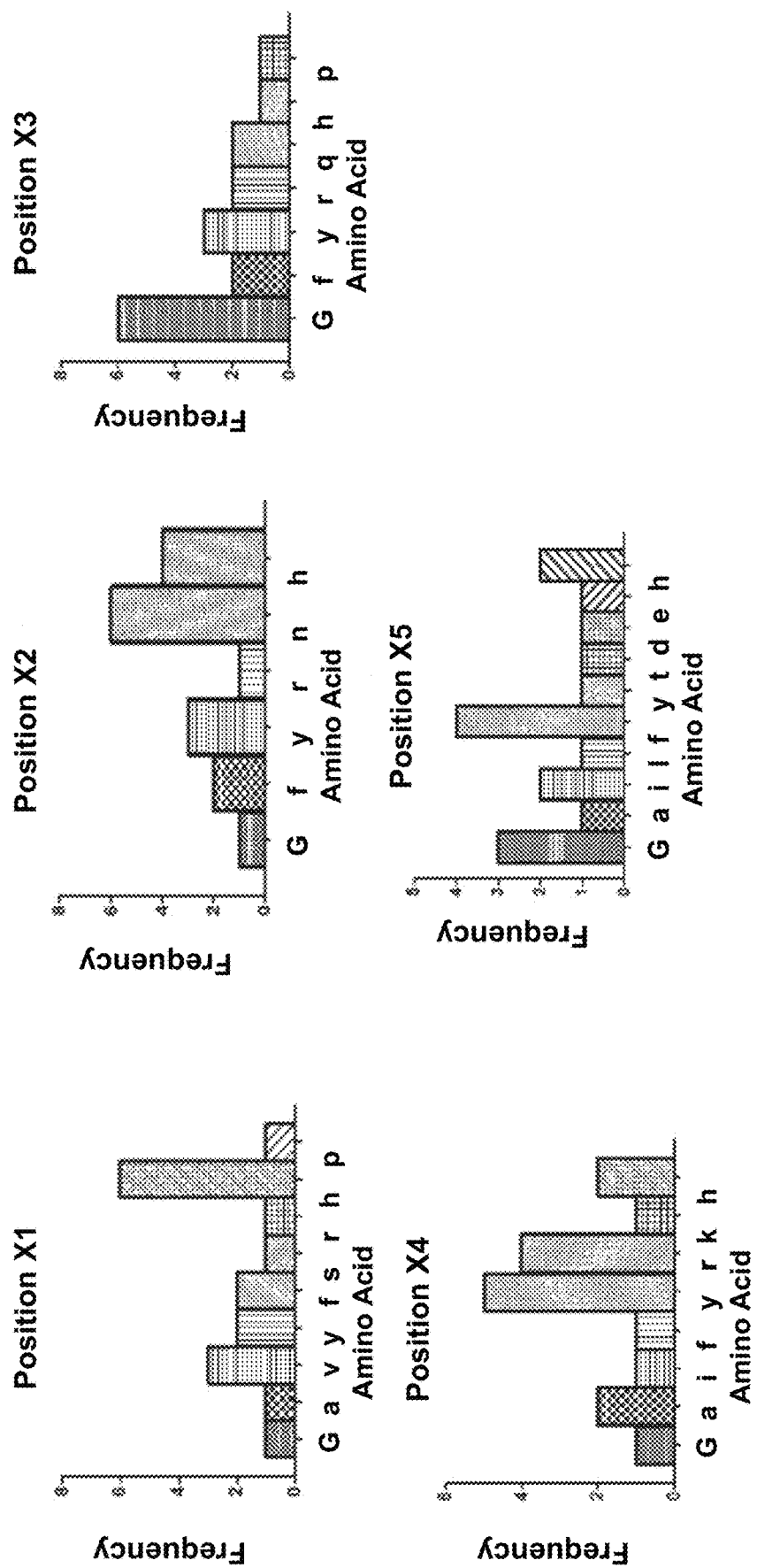
FIG. 19: Histogram of biligand hit sequences from the in situ click screen. Amino acid frequencies in the hit sequences X1X2X3X4X5-(D-Pra) (SEQ ID NO:20) from X1 to X5 are plotted as histograms. On the basis of the frequencies, hnGyf-(D-Pra) (SEQ ID NO:21) is the consensus sequence.

Selection of final biligand bi-L: Several biligand candidates were synthesized by Cu catalyzed click reaction which contained either a direct hit sequence (hnGyG-(D-Pra)) (SEQ ID NO:22), hnGre-(D-Pra) (SEQ ID NO:23), hnGai-(D-Pra) (SEQ ID NO:24), hnGii-(D-Pra) (SEQ ID NO:35), hnGGd-(D-Pra) (SEQ ID NO:36)) or the consensus sequence from the amino acid histograms (hnGyf-(D-Pra) (SEQ ID NO:21) from FIG. 19) as the 2° peptide. Biligands with the second peptide arm as hnGyG-(D-Pra) (SEQ ID NO:22) (Bi1), hnGyf-(D-Pra) (SEQ ID NO:21) (Bi2), hnGre-(D-Pra) (SEQ ID NO:23) (Bi3), hnGai-(D-Pra) (SEQ ID NO:24) (Bi4), hnGii-(D-Pra) (SEQ ID NO:35) (Bi5), hnGGd-(D-Pra) (SEQ ID NO:36) (Bi6) were tested for immunoprecipitation of Akt from OVCAR3 cells. Eluents from the immunoprecipitation from Bi1, Bi2, Bi3 and Bi4 were run on a western blot and eluents from the immunoprecipitation from Bi5 and Bi6 are blotted directly on nitrocellulose and treated with anti-Akt pan antibody. The western blot was given in FIG. 20A and the dot blot did not show any Akt pulldown. On the basis of the pulldown efficiency Bi1, which has hnGyf-(D-Pra) (SEQ ID NO:21) as the 2° peptide arm, was chosen as the final biligand candidate.

TABLE 2

Hit sequences from biligand (bi-L) screen with 25 nM target peptide. Consensus motifs are in bold fonts.

| X1 | X2 | X3 | X4 | X5 | D-Pra | |
|---|---|---|---|---|---|---|
| h | n | G | i | i | D-Pra | SEQ ID NO: 35 |
| h | n | G | r | e | D-Pra | SEQ ID NO: 37 |
| h | r | y | y | G | D-Pra | SEQ ID NO: 38 |
| v | n | r | r | f | D-Pra | SEQ ID NO: 39 |
| h | n | G | G | d | D-Pra | SEQ ID NO: 36 |
| a | y | p | h | f | D-Pra | SEQ ID NO: 40 |
| G | f | r | r | f | D-Pra | SEQ ID NO: 41 |
| r | G | f | f | l | D-Pra | SEQ ID NO: 42 |
| h | n | G | y | G | D-Pra | SEQ ID NO: 22 |

TABLE 3

Hit sequences from biligand screen with 10 nM target peptide. Consensus motifs are in bold fonts.

| X1 | X2 | X3 | X4 | X5 | D-Pra | |
|---|---|---|---|---|---|---|
| v | y | y | r | h | D-Pra | SEQ ID NO: 43 |
| h | n | G | a | i | D-Pra | SEQ ID NO: 24 |
| f | h | y | y | y | D-Pra | SEQ ID NO: 44 |
| f | y | h | k | h | D-Pra | SEQ ID NO: 45 |
| p | f | q | h | f | D-Pra | SEQ ID NO: 46 |
| s | h | f | y | t | D-Pra | SEQ ID NO: 47 |
| v | h | G | a | a | D-Pra | SEQ ID NO: 48 |
| y | h | q | y | G | D-Pra | SEQ ID NO: 49 |

Example 5.3: Screen for N-tL

Example 5.3.1: Prescreen 500 mg of library A (D-Pra-XXXXX-10% M-TG, Table 1) (SEQ ID NO:32) were swelled in binding buffer (25 mM Tris-Cl (pH=7.5), 150 mM NaCl, 10 mM $MgCl_2$, 0.1% BSA, 0.05% Tween-20) overnight. The beads were incubated with 25 µM solution of anchor-3N in binding buffer for two hours at 4° C. The beads were washed three times for five minutes each, with binding buffer. The beads were treated for two hours with 7.5 M Guanidium chloride (pH=2) and washed ten times with double distilled water. The beads were equilibrated in binding buffer. A 1:10,000 dilution of mouse anti biotin antibody-Alkaline phosphatase conjugate (Sigma) in binding buffer was added to the beads. The beads were washed three times, for five minutes each, with wash buffer 3 (25 mM Tris-Cl (pH=7.5), 150 mM NaCl, 10 mM $MgCl_2$, 0.05% (v/v) Tween-20), followed by three five minute washes with wash buffer 4 (25 mM Tris-Cl (pH=7.5), 150 mM NaCl, 10 mM $MgCl_2$). The beads were then developed in BCIP solution for thirty minutes and quenched with 0.1 N HCl. The blue hit beads, which were background binders to the anchor-3N or the antibody were separated from the rest of the beads. The clear beads were stringently washed with DMF, guanidium hydrochloride and water and used in the product screen.

Example 5.3.2: Product Screen

The clear beads from the prescreen were swelled overnight in binding buffer (25 mM Tris-Cl (pH=7.5, 150 mM NaCl, 10 mM $MgCl_2$, 0.05% (v/v) Tween-20, and 0.1% BSA). 25 µM solution of anchor-3N was incubated for thirty minutes at 4° C. with 50 nM Akt2 in binding buffer. The solution was added to the beads and shaken at 4° C. for two hours. The beads were washed three times, for five minutes each, with the binding buffer. The beads were treated for two hours with 7.5 mM guanidium chloride (pH=2) and washed ten times with double distilled water. The beads were re-equilibrated in binding buffer. A 1:10,000 dilution of mouse anti biotin antibody-alkaline phosphatase conjugate (Sigma) in binding buffer was added to the beads. The beads were washed three times, for five minutes each, with wash buffer 3 followed by three five minutes washes with wash buffer 4. The beads were then developed in BCIP solution for thirty minutes and quenched with 0.1 N HCl. The blue hit beads were picked up manually, stringently washed with DMF, guanidium hydrochloride and water, and used in the target screen.

Example 5.3.3: Target Screen

The washed hit beads from the product screen were swelled overnight in binding buffer (25 mM Tris-Cl (pH=7.5, 150 mM NaCl, 10 mM $MgCl_2$, 0.05% (v/v) Tween-20, and 0.1% BSA). 50 nM Akt2 protein, preincubated with 73.5 µM anchor-3N for thirty minutes at 4° C., was added to the swelled beads and the beads were shaken for ninety minutes at 4° C. The beads were washed three times, for five minutes each, with the binding buffer. A 1:1000 dilution of mouse anti $His_6$ (SEQ ID NO:28) antibody (Abcam) in binding buffer was added to the beads and incubated for an hour with shaking at 4° C. Following three five minute washes with the binding buffer, a 1:10,000 diluted solution of anti mouse-alkaline phosphatase (Sigma) was added and the shaken for one hour at 4° C. The beads were washed three times for five minutes each with wash buffer 3, followed by three five minute washes with wash buffer 4. The beads were then developed in BCIP solution for thirty minutes and quenched with 0.1 N HCl. The blue hit beads were picked up manually, stringently washed with DMF, guanidium hydrochloride and water, and sequenced on the Edman Sequencer. The sequences obtained are listed in Table 4. Because of poor resolution of amino acid standards in the Edman Peptide Sequencer during that time, some peptides were assigned to have either one of two amino acids in some positions.

TABLE 4

Hit sequences from N terminal triligand (N-tL) screen.

| D-Pra | X1 | X2 | X3 | X4 | X5 | |
|---|---|---|---|---|---|---|
| D-Pra | k/l* | f | q | f | r | SEQ ID NO: 50 |
| D-Pra | r | d/n* | r | f | r | SEQ ID NO: 51 |
| D-Pra | y | V | y | r | f | SEQ ID NO: 52 |
| D-Pra | s | S | G | r | y | SEQ ID NO: 14 |
| D-Pra | y | Y | r | f | g | SEQ ID NO: 13 |
| D-Pra | s | F | r | r | f | SEQ ID NO: 53 |
| D-Pra | s | v | r | f | r | SEQ ID NO: 54 |
| D-Pra | i | k/l* | r | r | a | SEQ ID NO: 55 |
| D-Pra | r | q/t* | k/l* | w | r | SEQ ID NO: 56 |
| D-Pra | r | q/t* | s | r | r | SEQ ID NO: 57 |
| D-Pra | r | r | i | y | y | SEQ ID NO: 58 |
| D-Pra | r | f | G | r | q/t* | SEQ ID NO: 59 |

*Alternative amino acid signals from poor resolution of the amino acid standards of the Edman sequencing machine.

Example 5.3.4: Elimination of Peptides Binding to Anti-Akt Antibody

Since a preclear screen was not performed against the mouse-Anti His$_6$ antibody and the anti-mouse-alkaline phosphatase antibody, to eliminate peptide binders to the antibodies, all the dark colored peptide hits obtained in the earlier target screen were synthesized on Tentagel-S—NH$_2$ resin. 10 beads of each sequence was taken in spinnex tubes, equilibrated in binding buffer, and then treated with a 1:1000 diluted solution of mouse anti His$_6$ antibody (Abcam) for an hour at 4° C. Following three five minute washes with the binding buffer, a 1:10,000 diluted solution of anti mouse-alkaline phosphatase was added and the shaken for one hour at 4° C. The beads were washed three times for five minutes each with wash buffer 3, followed by three five minute washes with wash buffer 4. The beads were then developed in BCIP solution for thirty minutes and quenched with 0.1 N HCl. The color intensity of the different sequences is recorded in Table 5, along with the probability that the sequence is a binder to the protein and not a background binder (clear beads). The probability arises from the poor resolution of certain amino acid standards in the Edman sequencer during sequencing the hits from the N terminal triligand target screen.

TABLE 5

Elimination of peptide binders to antibody from N terminal triligand (N-tL) screen.

| D-Pra | X1 | X2 | X3 | X4 | X5 | Color | Probability of being right sequence | |
|---|---|---|---|---|---|---|---|---|
| D-Pra | k | f | q | f | r | light | 0.25 | SEQ ID NO: 60 |
| D-Pra | l | f | q | f | r | light | 0.25 | SEQ ID NO: 61 |
| D-Pra | k | f | t | f | r | light | 0.25 | SEQ ID NO: 62 |

TABLE 5-continued

Elimination of peptide binders to antibody from N terminal triligand (N-tL) screen.

| D-Pra | X1 | X2 | X3 | X4 | X5 | Color | Probability of being right sequence | |
|---|---|---|---|---|---|---|---|---|
| D-Pra | l | f | t | f | r | light | 0.25 | SEQ ID NO: 63 |
| D-Pra | r | d | r | f | r | No color | 0.5 | SEQ ID NO: 64 |
| D-Pra | r | n | r | f | r | medium | 0.5 | SEQ ID NO: 65 |
| D-Pra | y | v | y | r | f | light | 1 | SEQ ID NO: 52 |
| D-Pra | s | s | G | r | y | No color | 1 | SEQ ID NO: 14 |
| D-Pra | r | r | i | y | y | dark | 1 | SEQ ID NO: 58 |
| D-Pra | y | y | r | f | G | No color | 1 | SEQ ID NO: 13 |
| D-Pra | s | f | r | r | f | light | 1 | SEQ ID NO: 53 |

Figure 20A:
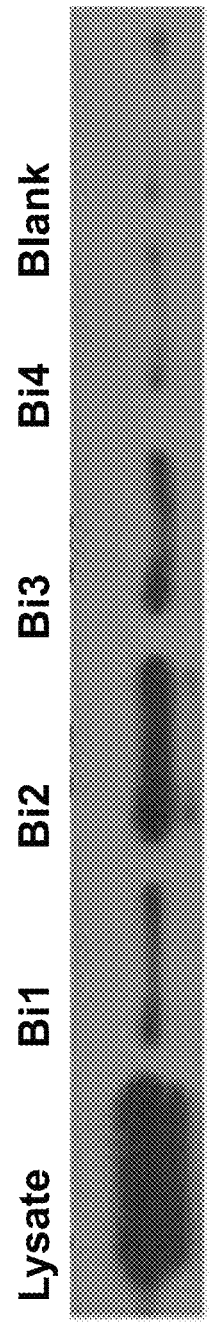
FIG. 20: The selection of bi- and triligands on the basis of the efficiency to immunoprecipitate Akt from OVCAR3 cells. A. Biligand selection on the basis of the efficiency to immunoprecipitate Akt from OVCAR3 cells. Biligands with hnGyG-(D-Pra) (SEQ ID NO:22) (Bi1), hnGyf-(D-Pra) (SEQ ID NO:21) (Bi2), hnGre-(D-Pra) (SEQ ID NO:23) (Bi3), hnGai-(D-Pra) (SEQ ID NO:24) (Bi4) as the 2° peptide arm are used to immunoprecipitate Akt2 from OVCAR3 cells following the described procedure. The best candidate Bi2 is chosen as the biligand bi-L and used in further stages of ligand development. That candidate contained the 2° peptide sequence (hnGyf) (SEQ ID NO:7) which, remarkably, is the sequence that best reflects the statistic illustrated in the positional histograms of FIG. 19. B: N-terminal triligand selection on the basis of the efficiency to immunoprecipitate Akt from OVCAR3 cells. N-terminal triligands synthesized with (D-Pra)-yyrfG (SEQ ID NO:13) (N-tri1) and (D-Pra)-ssGry (SEQ ID NO:14) (N-tri2) immunoprecipitate Akt2 from OVCAR3 cells. N-tri1 is chosen as the final N terminal triligand N-tL. C. N-terminal triligand selection on the basis of epitope binding characteristics. Triligand candidates from the C terminal screen are tested for binding to the target epitope. The ligand C-t1, with (L-Az4)-hdGGf (SEQ ID NO:25) as the third peptide arm, shows good binding and is chosen as the C-terminal triligand C-tL.
Figure 20B:
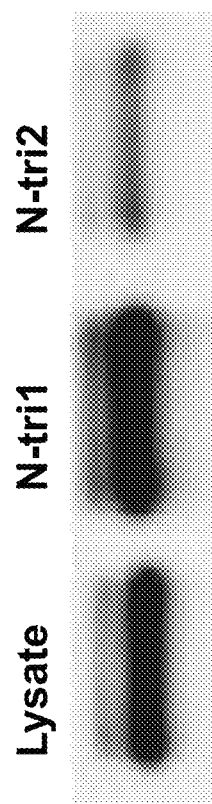

Selection of final N terminal triligand N-tL: Two sequences were observed (Table 5) which were not background binders (remain clear in the antibody binder elimination screen) and which had the full probability of being the right sequence. These two 3° peptides, (D-Pra)-yyrfG (SEQ ID NO:13) and (D-Pra)-ssGry (SEQ ID NO:14), were clicked to anchor-3N by CuAAC reaction and tested as triligand candidates (N-tri1 and N-tri2 respectively). These were used to immunoprecipitate Akt2 from OVCAR3 cells (FIG. 20B). The first triligand candidate N-tri1 being more efficient was chosen as the final N terminal triligand N-tL.

Example 5.4: Screen for C-tL

Example 5.4.1: Prescreen 500 mgs of library C (H$_2$N-Az$_4$-XXXXX-10% M-TG, Table 1) (SEQ ID NO:34) was swelled in binding buffer overnight. The beads were incubated with 100 µM solution of anchor-3C in binding buffer for two hours at 4° C. The protocol for the prescreen for N-tL screen was followed. The blue hit beads, which were background binders to the anchor-3C or the detection antibody were separated from the rest of the beads. The clear beads were stringently washed with DMF, guanidium hydrochloride and water and used in the product screen that followed.

Example 5.4.2: Product Screen

The washed beads from the prescreen were swelled overnight in binding buffer 100 µM solution of anchor-3C was incubated for thirty minutes at 4° C. with 50 nM Akt2 in binding buffer. The solution was added to the beads and shaken at 4° C. for two hours. The protocol for the N-tL product screen was followed. The blue hit beads were picked up manually, stringently washed with DMF, guanidium hydrochloride and water, and sequenced on the Edman Sequencer. The sequences are recorded in Table 6.

TABLE 6

Hit sequences from C terminal triligand (C-tL) screen. Consensus motifs are bold fonts.

| L-Az4 | X1 | X2 | X3 | X4 | X5 | |
|---|---|---|---|---|---|---|
| L-Az4 | h | d | G | s | q | SEQ ID NO: 66 |
| L-Az4 | h | d | G | w | w | SEQ ID NO: 67 |
| L-Az4 | h | d | G | i | v | SEQ ID NO: 68 |
| L-Az4 | h | d | G | d | w | SEQ ID NO: 69 |
| L-Az4 | h | d | G | G | —* | SEQ ID NO: 70 |
| L-Az4 | h | d | G | d | r | SEQ ID NO: 71 |
| L-Az4 | h | d | G | G | f | SEQ ID NO: 72 |

TABLE 6-continued

Hit sequences from C terminal triligand (C-tL) screen. Consensus motifs are bold fonts.

| L-Az4 | X1 | X2 | X3 | X4 | X5 | |
|---|---|---|---|---|---|---|
| L-Az4 | h | d | G | G | e | SEQ ID NO: 73 |
| L-Az4 | h | d | G | s | f | SEQ ID NO: 74 |
| L-Az4 | h | d | G | q | k | SEQ ID NO: 75 |
| L-Az4 | h | d | G | s | a | SEQ ID NO: 76 |
| L-Az4 | h | d | G | k | f | SEQ ID NO: 77 |
| L-Az4 | r | l | e | a | v | SEQ ID NO: 78 |

\* no signal

Figure 20C:
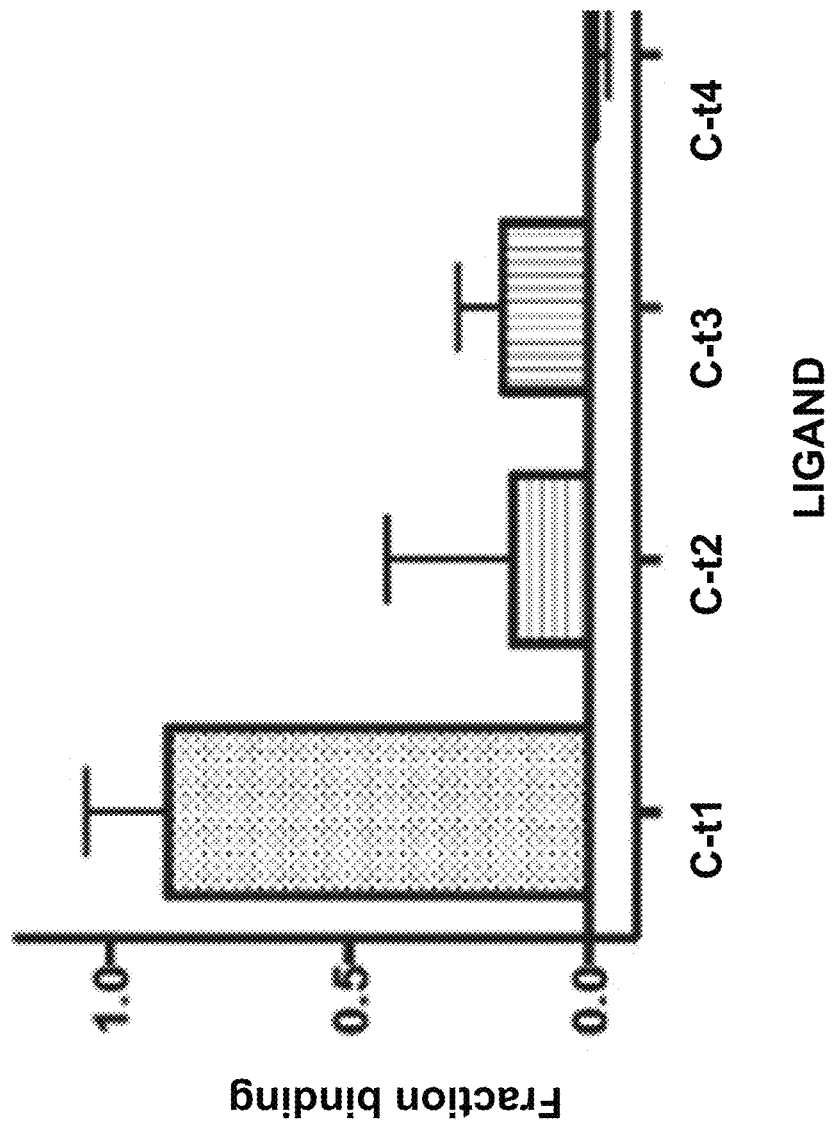

Selection of the final C terminal triligand C-tL: Four triligand candidates were synthesized with (L-Az4)-hdGGf (SEQ ID NO:25) (C41), (L-Az4)-hdGsf (SEQ ID NO:74) (C-t2), (L-Az4)-hdGww (SEQ ID NO:67) (C-t3), (L-Az4)-hdGkf (SEQ ID NO:77) (C-t4) as the 3° peptide arm. Binding of the candidates to the target peptide epitope was determined in an ELISA assay (FIG. 20C) and the ligand C-t1 emerged as the best binder. C-t1 was chosen as the C terminal triligand C-tL.

Example 6: Epitope/Protein Selectivity Assay 1.25 µM biotinylated ligand was prepared by diluting the 1 mM stock in binding buffer (25 mM tris chloride, pH=7.4, 150 mM NaCl, 0.1% BSA, 0.05% Tween 20). The prepared ligand solution or 0.125% DMSO in buffer (buffer control) was immobilized on a High Capacity Streptavidin 96 well plate (Thermo Scientific). After washing away the excess ligand, the plate was blocked overnight with 1% BSA/25 mM tris chloride, pH=7.4/150 mM NaCl, 0.05% Tween 20. 2.5 µM solutions of the $His_6$ (SEQ ID NO:28) tagged target phosphopeptide epitope Akt2 amino acids 450-481, $His_6$ (SEQ ID NO:28) tagged Akt1 amino acids 449-480, $His_6$ (SEQ ID NO:28) tagged Akt3 amino acids 448-479 were added to each of the wells. Following three washes with the binding buffer, the plate was treated for an hour with a 1:1000 dilution of anti $His_6$ (SEQ ID NO:28) mouse monoclonal antibody. A 1:10,000 dilution of goat anti mouse antibody-Horse Radish Peroxide conjugate in binding buffer was added to the wells. The plates were washed four times, five minutes each, with 0.05% Tween 20/TBS (25 mM tris chloride, pH=7.5, 150 mM NaCl) and once with TBS (25 mM tris chloride, pH=7.5, 150 mM NaCl). Color was developed by adding TMB substrate (KPL) to each well. The reaction was quenched with 0.5 M $H_2SO_4$. The A450 measured on a 96-well plate reader. The Net A450 was obtained by subtracting the absorbance value for the blank control (no immobilized ligand) from each of the triplicate values obtained for the ligand-epitope interaction. The selectivity assay with full length $His_6$ (SEQ ID NO:28) tagged Akt1, Akt2 and Akt3 was performed following the same protocol, using 25 nM protein instead of 2.5 µM $His_6$ tagged peptide epitope.

Example 7: Measurement of Binding Affinity of N-tL by Surface Plasmon Resonance A Biacore T100 machine was used for SPR experiments. A Streptavidin Chip (Series S, G.E. Healthcare) was conditioned as per manufacturer's recommendation. A stock of 1 mM biotinylated ligand was diluted into HBSP+ Buffer (G.E. Healthcare) to a final concentration of 100 nM and ~150 RU was immobilized on the chip. Serial dilutions of the Akt2 protein were made in HBSP+ buffer for the experiment with the immobilized N-tL. The solution was flowed over the chip at 50 µL/min. Binding and dissociation were carried out at 10° C. with a contact time of 350 sec, a dissociation time of 390 sec, and a stabilization time of 200 sec, with buffer blanks between each concentration. The response was double corrected, using an unmodified reference flow cell and the response for the 0 concentration of Akt2 on the sample flow cell. The data was fitted to the kinetic Langmuir 1:1 binding model using the Biacore Evaluation software for T100 to calculate the dissociation constant.

Example 8: OVCAR3 Lysate Pull-Down Assay

OVCAR3 cells (ATCC) were grown in RPMI-1640 media containing 20% fetal bovine serum. Passage three cells were grown to ~80% confluence. Cells were lysed with lysis buffer (10 mM Tris-Cl (pH=7.5), 100 mM NaCl, 1% (v/v) Triton X-100, 0.1% SDS (w/v), 0.5% deoxycholate, 1 mM DTT, 1 mM EDTA, 1× PhosStop phosphatase inhibitors (Roche), 1× Complete protease inhibitors (Roche)) and the amount of protein measured using BCA Protein Assay Kit (Pierce Biotechnologies, Inc). Streptavidin-agarose resin solution (EMD) was swelled in TBST (25 mM tris chloride, pH=7.5, 150 mM NaCl, 0.05% Tween-20). Each of the biotinylated ligands was immobilized on the Streptavidin-agarose resin by adding 7.2 µL of 1 mM ligand stock (DMSO) to 10 µL of the swelled streptavidin-agarose resin. For the blank control, the resin was treated with 7.2 µL of 1 mM biotinylated acyl glycine. Biotinylated pS473 antibody (Cell Signaling) was added in a 1:200 ratio as per vendor's suggestion. After shaking overnight at 4° C., 50 µM D-biotin was added to the resin to block any remaining sites. The resin was washed with TBST five times, for fifteen minutes each. The resin was then swelled in binding buffer for two hours. To each of the immobilized ligands, 200 µL OVCAR3 cell lysate (1.9 mg/ml) was added. The tubes were shaken at 4° C. for 18 hours. The beads were extensively washed, three times for fifteen minutes in binding buffer, three times (fifteen minutes) in TBST, and three times (fifteen minutes) in TBS to remove unbound proteins. The resin bound proteins were eluted by adding 40 µL of 2×SDS-PAGE sample loading buffer (BioRad) and heating at 95° C. for five minutes. A 1:10 diluted sample of lysate in sample loading buffer was prepared by mixing 1 µL of the sample with 9 µL sample loading buffer and denaturing the sample by heating at 95° C. for five minutes. 10 µL of each sample was loaded on a 12% SDS-PAGE gels (BioRad) and run for 80 minutes at 110 volts. Three identical gels were loaded and run at the same time. One gel was used for Coomassie staining with Coomassie Fluor Orange Protein Gel Stain (Molecular Probes) following the manufacturer's protocol. The two other gels were transferred to nitrocellulose membranes by the semidry transfer method, blocked for two hours at 4° C. with 5% non-fat milk, and treated overnight at 4° C. with a 1:1000 dilution of pan-Akt rabbit monoclonal antibody (Cell Signaling Technology) and a 1:1000 dilution of pS473 Akt rabbit monoclonal antibody (Cell Signaling Technology), respectively, in 0.5% non-fat milk. The membranes were washed and treated for an hour with a 1:10,000 dilution of monoclonal mouse anti-rabbit-HRP secondary antibody (Cell Signaling Technology) in 0.5% milk. After five washes of five minutes each with TBST and one wash of five minutes with TBS, the blots were developed with West Dura ECL substrate (Thermo Scientific) and imaged on film.

Example 9: Non-Radioactive Kinase Assay to Evaluate Effect of Ligands on Akt2 Kinase Activity The non-radioactive kinase assay kit for Akt2 was purchased from Cell Signaling. Ligand solutions were made in DMSO. Kinase reactions were set up in 1× kinase buffer (25 mM trisHCl (pH 7.5), 10 mM $MgCl_2$, 0.01% Triton-X, 1× Complete protease inhibitor (Roche), 1× Phosstop phosphatase inhibitor (Roche)), each 25 µL reaction mixture containing 400 ng Akt2, 400 ng GST-GSK-3α/β fusion protein, 500 mM ATP and 0.5 µL of peptide solutions in DMSO or DMSO only. Reactions were allowed to proceed for 30 minutes at 30° C. A reaction mixture was also prepared using a 1:2.5 dilution of anti pS473 antibody (Cell Signaling) in the kinase buffer instead of the peptide ligand or DMSO. The reactions were quenched by adding 12.5 µL of 2×SDS sample loading buffer and heating at 95° C. for five minutes. 10 µL from each sample was loaded on an any kD SDS gel (BioRad) and run for an hour at 110 volts. Following semidry transfer of the gel to a nitrocellulose membrane, the membrane was blocked in 5% nonfat milk/TBST for an hour at 4° C., and treated overnight at 4° C. with a 1:200 dilution of Phospho GSK-3α/β Ser (21/9) rabbit antibody (Cell Signaling) in 0.5% milk/TBST. Following washes, the membrane was treated with a 1:2000 dilution of mouse anti-rabbit-HRP antibody for an hour at 4° C. After four five minute washes with TBST, and one five minute wash with TBS, the membrane was treated with West Dura ECL substrate (Thermo Scientific) and imaged on film.

Figure 18A:
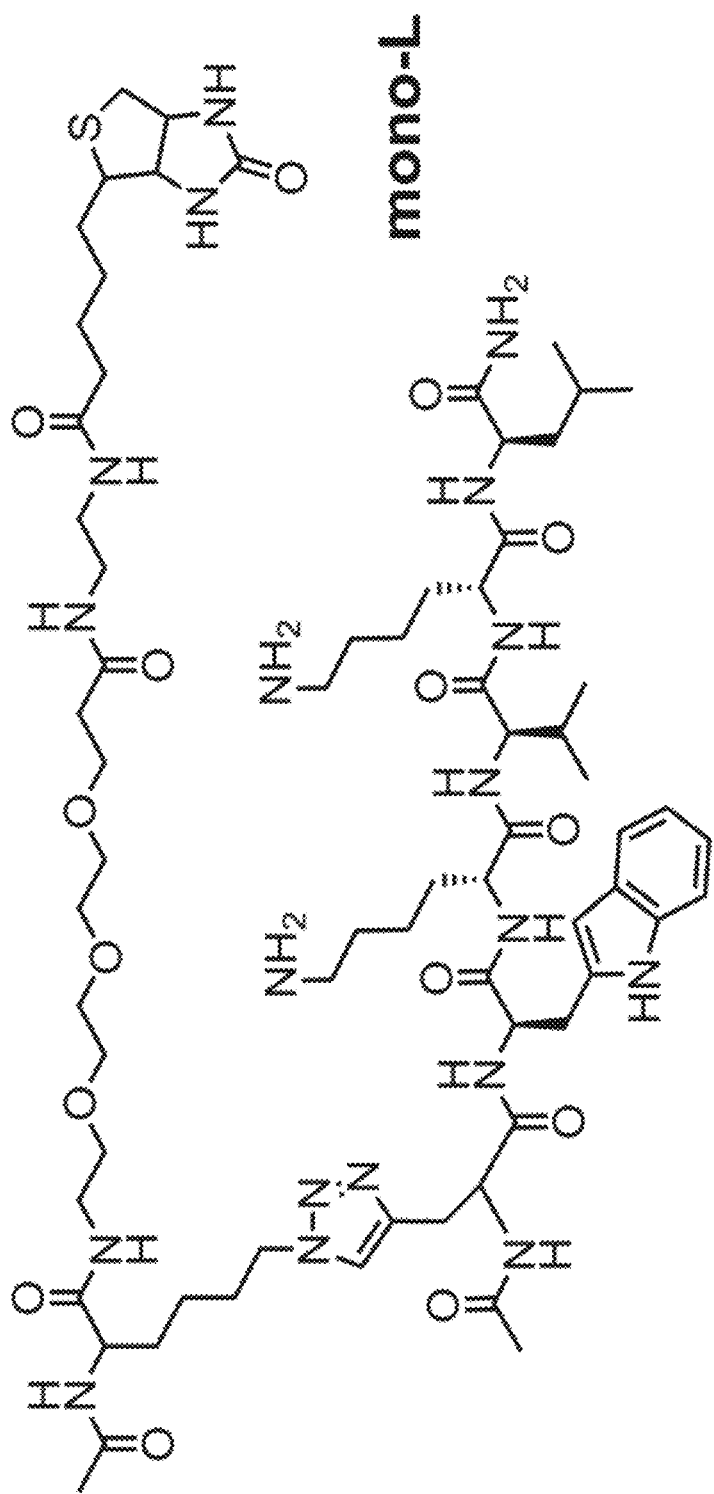
FIGS. 18A-E: Molecular structure of various PCC agents.
Figure 21A:
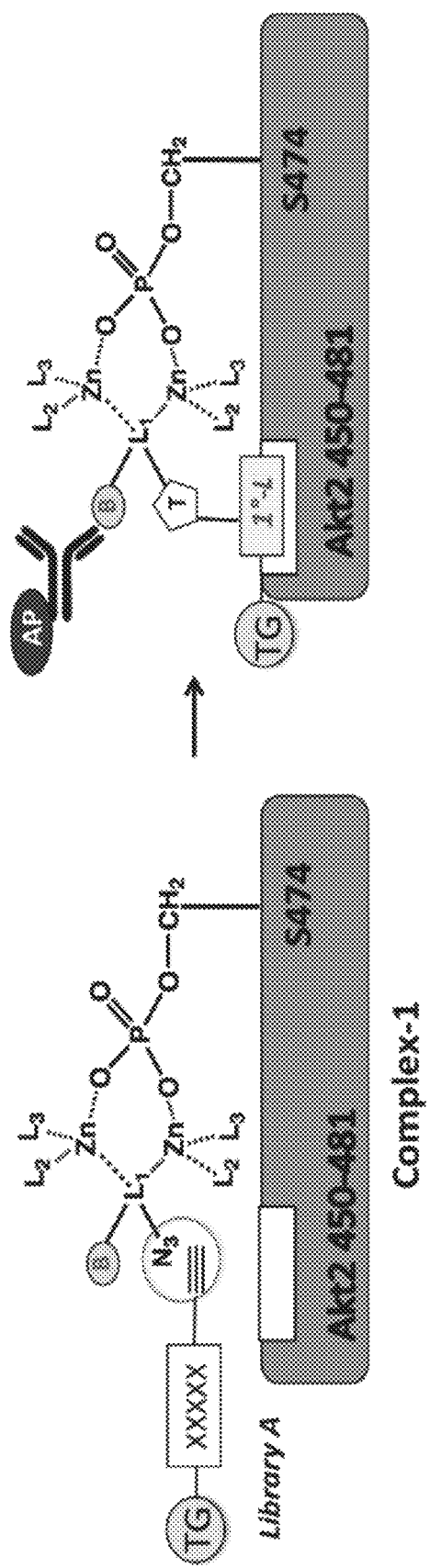
FIG. 21: The screening strategy for developing a PCC agent targeted near Ser474 of Akt2. A. Identification of a 1° ligand. Zn chelator 1 couples to the Akt2 C-terminal fragment through the pS474 to create Complex-1. Complex-1 is screened against Library A to yield 1° ligand candidates, from which a consensus 1° ligand (mono-L) is identified. B. Complex 2 is prepared from 1, mono-L, and the 32-mer pS474 containing polypeptide. Complex-2 is screened against Library B to identify candidate 2° ligands, from which two variations of the consensus biligand (bi-L) were prepared. The first, anchor-3N, was screened against Library A in the presence of full length Akt2 to identify candidate 3° ligands, from which a consensus N-terminal triligand, N-tL, was identified. Anchor-3C was similarly utilized to identify a consensus C-terminal triligand, C-tL.

Complex 1 was subjected to an in situ click screen (FIG. 21A) against a large one-bead-one-compound (OBOC) library (Library A) of acetylene-presenting hexameric peptides to identify an initial (1°) peptide ligand. See Table 1 for all OBOC libraries used here. The peptides were built from D-stereoisomers of the natural amino acids, to ensure protease stability in the final capture agent. The selectivity of this multistep screen was such that it produced two hit beads, which both sequenced to yield the same peptide ((D-Pra)-wkvkl (SEQ ID NO:4); D-Pra=D-propargylglycine). This 1° ligand, mono-L, (FIG. 18A), was found to have ~3 µM affinity by single-component immunoassay and to have sufficient selectivity to immunoprecipitate Akt from OVCAR3 cancer cell lysate, when immobilized on streptavidin agarose resin.

Figure 18B:
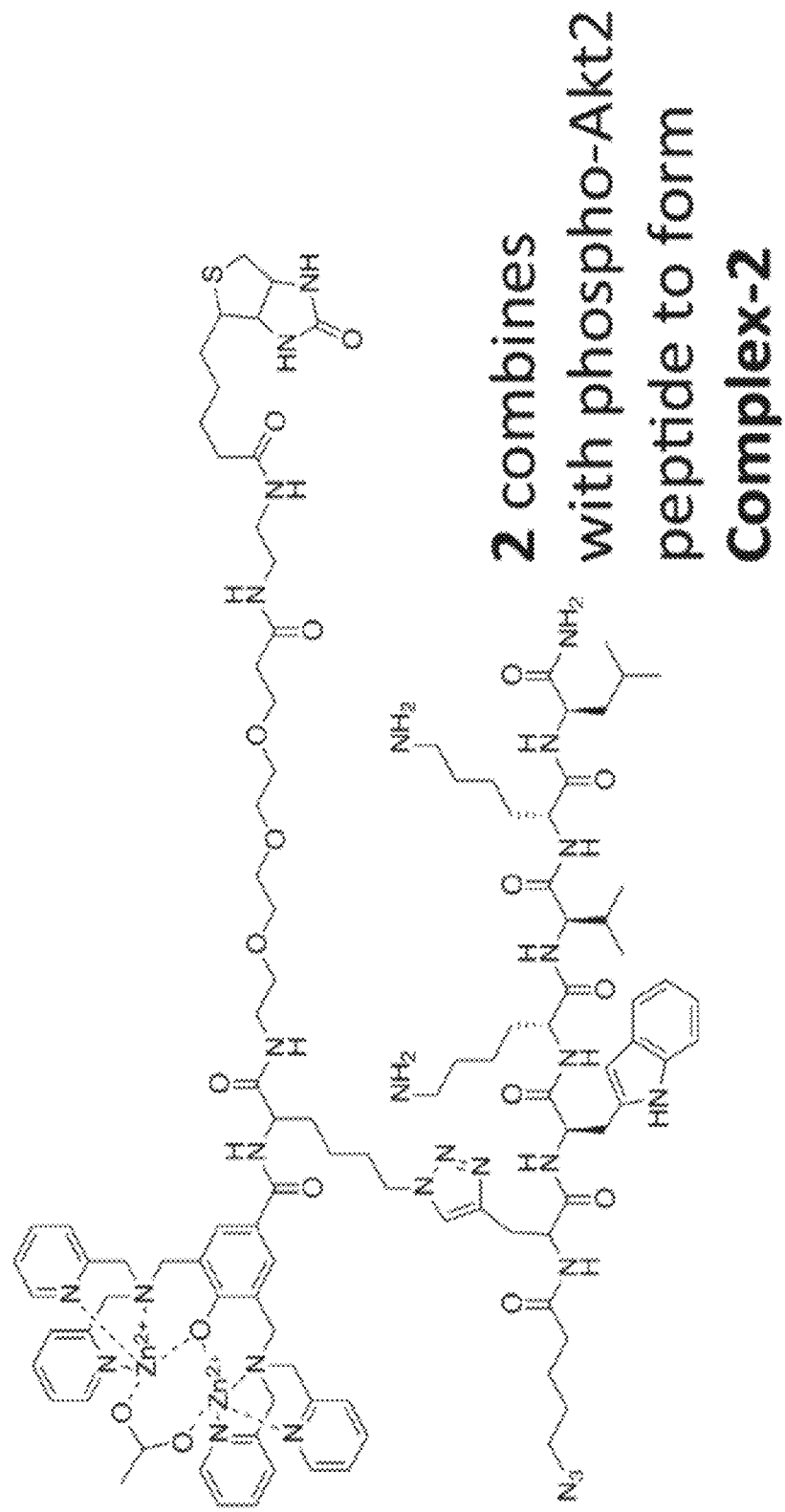
Figure 18C:
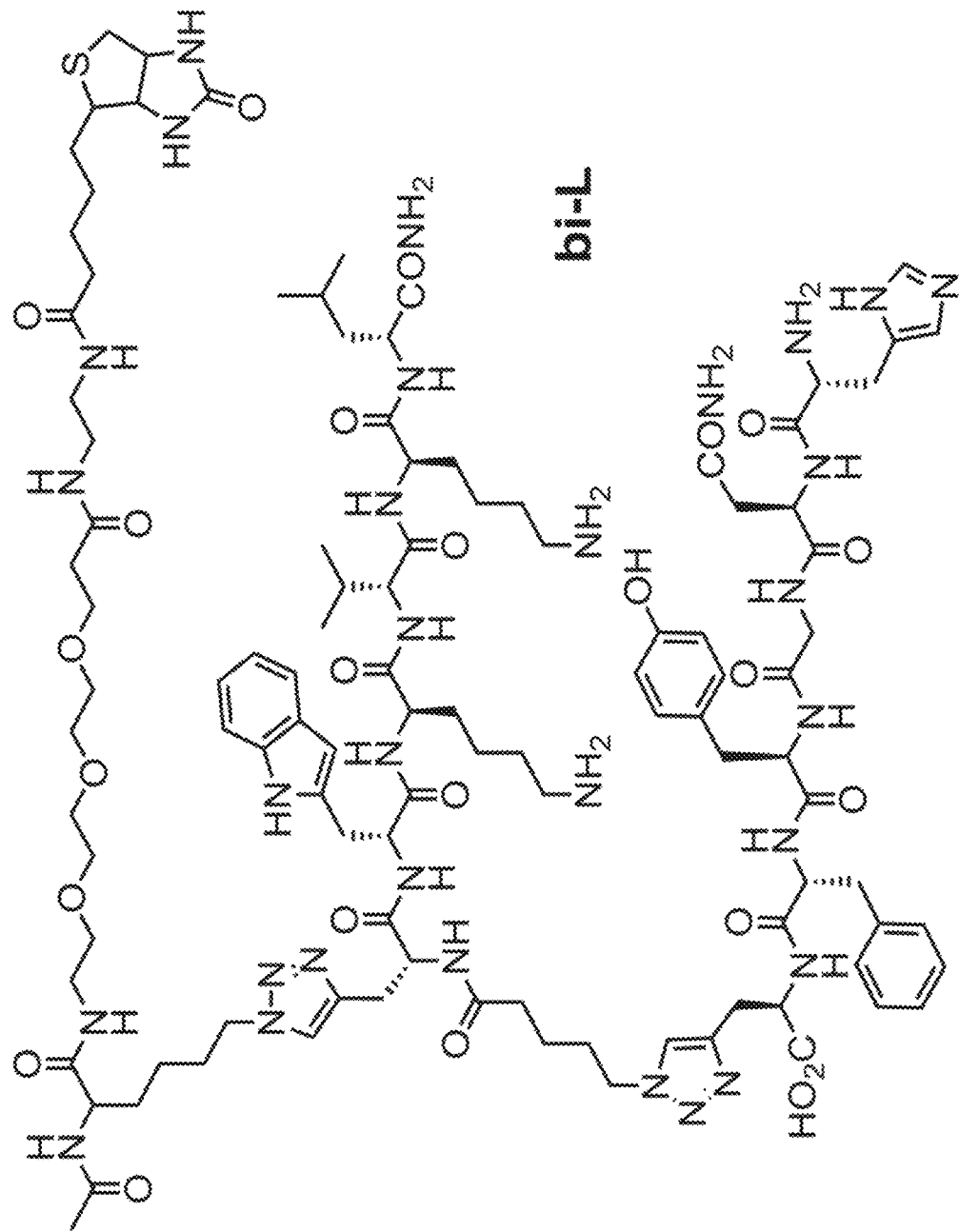
Figure 21B:
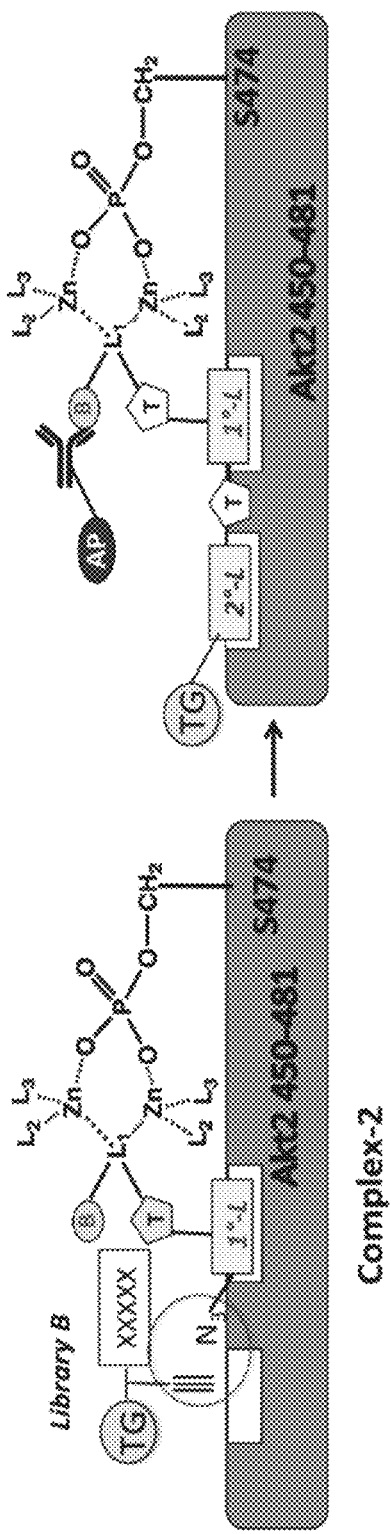

This strategy was iterated to identify candidate 2° ligands. Complex-2 was prepared from the Zn-chelator 1, the 1° ligand sequence, and the 32-mer polypeptide (FIG. 18B, FIG. 21B). Multi-step screens against Library B were carried out to eliminate background binders, and to identify 2° ligand candidates. The motif hnGxx was observed across several candidate 2° ligands (see Table 2, Table 3 and FIG. 19 for a listing and statistical analysis of those hit sequences). Biligand candidates were synthesized by linking the 1° and 2° peptides using Cu(I) catalyzed click chemistry, and then tested for affinity and specificity (FIG. 20A). The best performing biligand (FIG. 18C) exhibited a ~1 µM affinity, and higher selectivity to immunoprecipate Akt from OVCAR3 cell lysate.

Figure 18D:
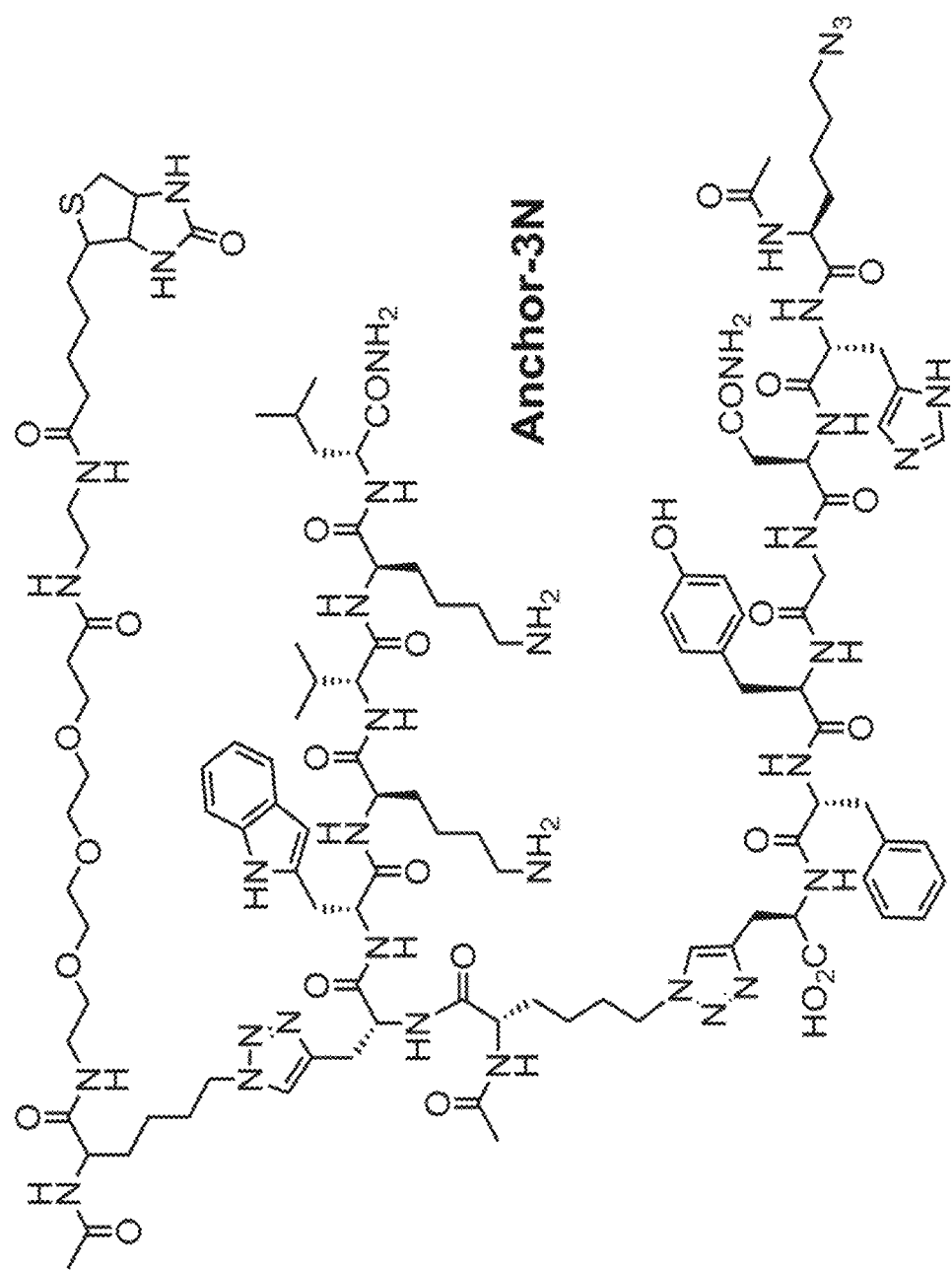
Figure 18E:
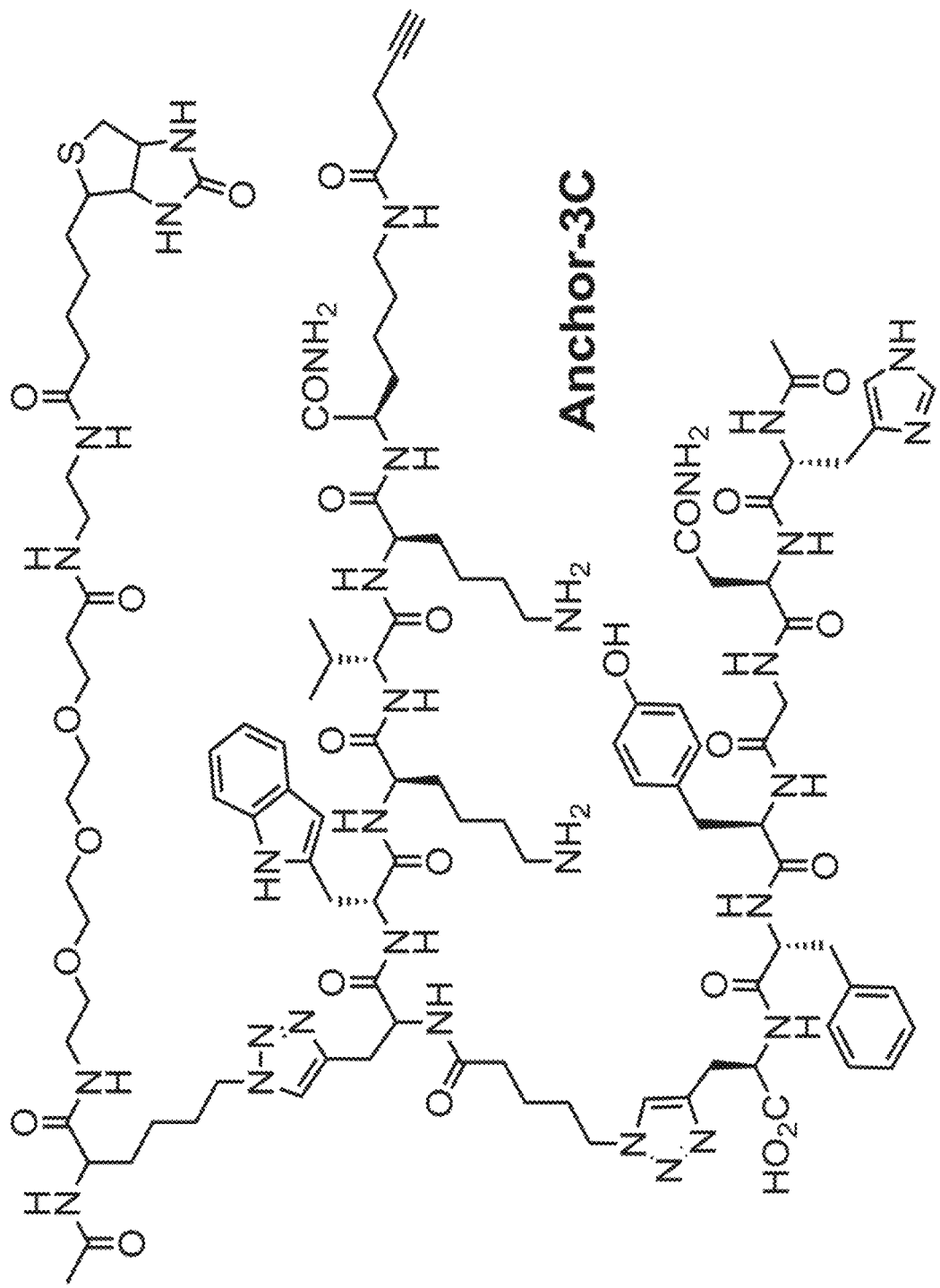
Figure 21C:
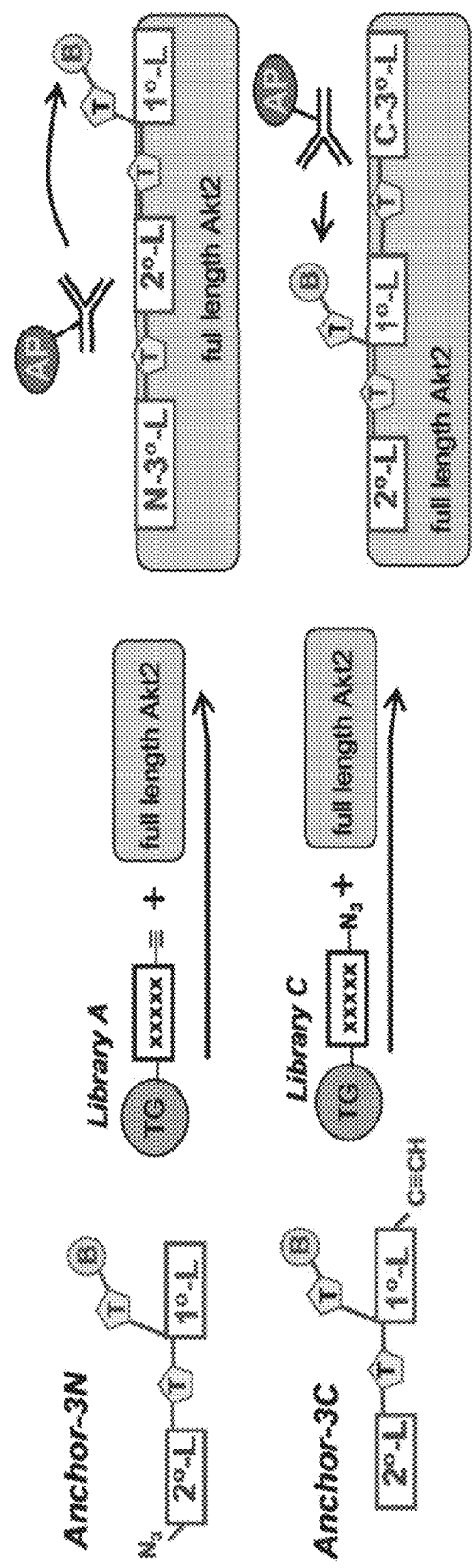
Figure 22A:
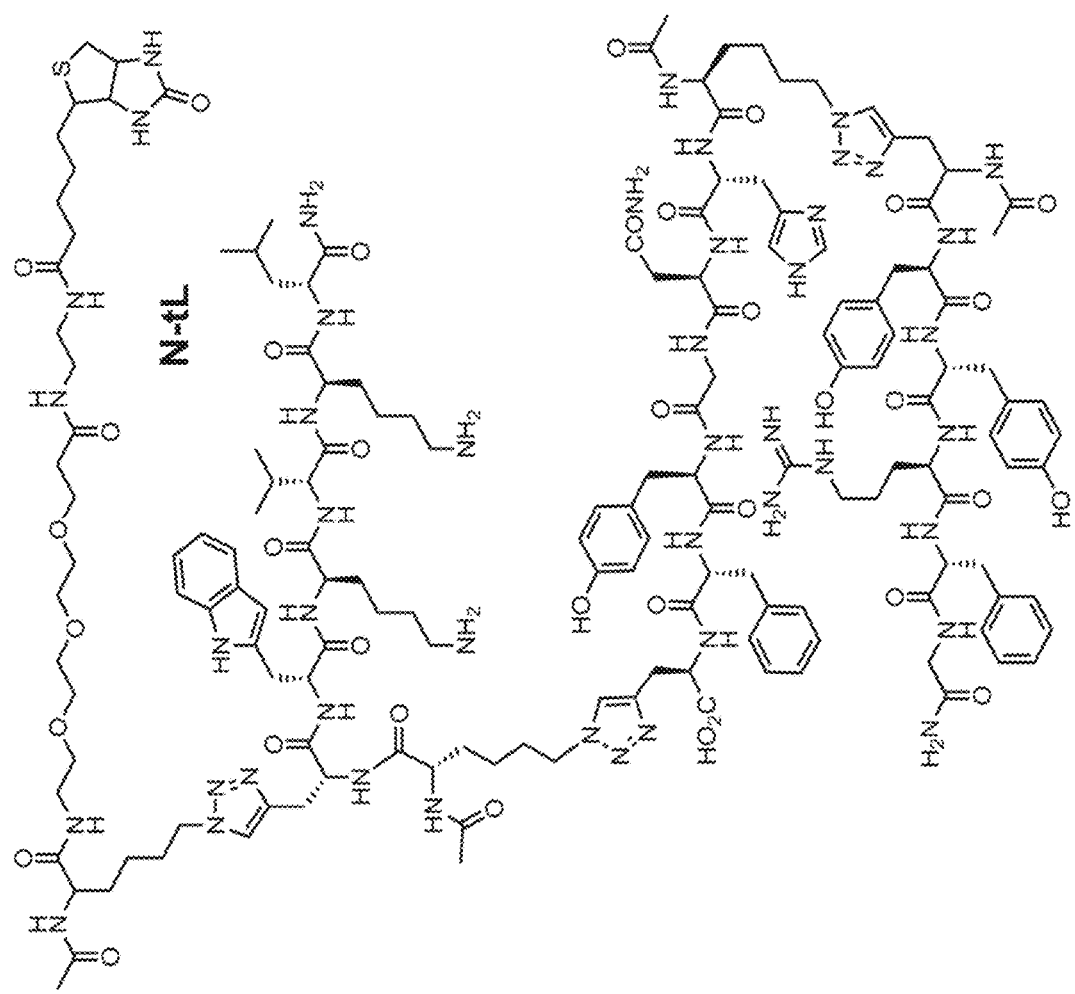
FIG. 22: Molecular structures of N-tL (A) and the C-tL (B) developed against the C-terminal epitope of Akt2 near the p-S474 residue. The 1° and 2° ligand branches are common to both PCC Agents, and are drawn in red and blue, respectively. The polyethylene-glycol-linked biotin groups were included in the development process, and so do not represent interfering perturbations.
Figure 22B:
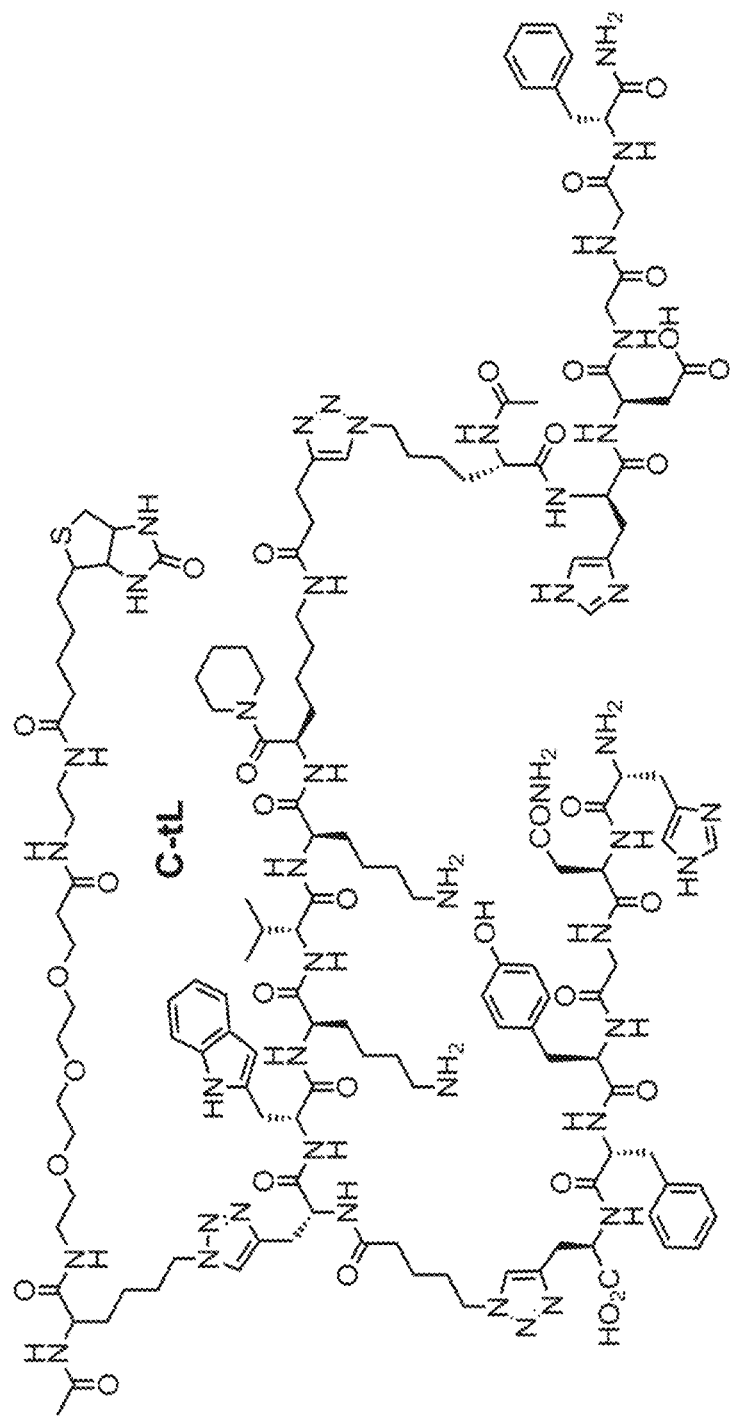

The biligand was expanded into two triligands via in situ click screens that utilized full-length active Akt2, two biligand-derived anchors anchor-3N (FIG. 18D) and anchor-3C (FIG. 18E), but no Zn chelator (FIG. 21C). An N-terminal triligand (N-tL; FIG. 1A) was developed by screening for 3° ligands that click to the N-terminus of the anchor-3N, while a C-terminal triligand (C-tL; FIG. 22B) was similarly developed by identifying 3° ligands that click to the C-terminus of the anchor-3C. All hit sequences assays used to guide the selection of the two best triligands are provided in Tables 4-6 and FIGS. 20B, 20C. The best 3° ligand for the C-tL (hdGGf (SEQ ID NO:79)) is somewhat similar to the 2° ligand sequence, perhaps indicating competition for the same site on the protein. The N-tL and C-tL yielded $EC_{50}$ values from single component ELISA assays of 19 and 125 nM, respectively (FIG. 23A). The $EC_{50}$ value for the N-tL (19 nM) compares well against the dissociation constant ($K_D$) value (25 nM) obtained using Surface Plasmon Resonance (FIG. 24).

Figure 23B:
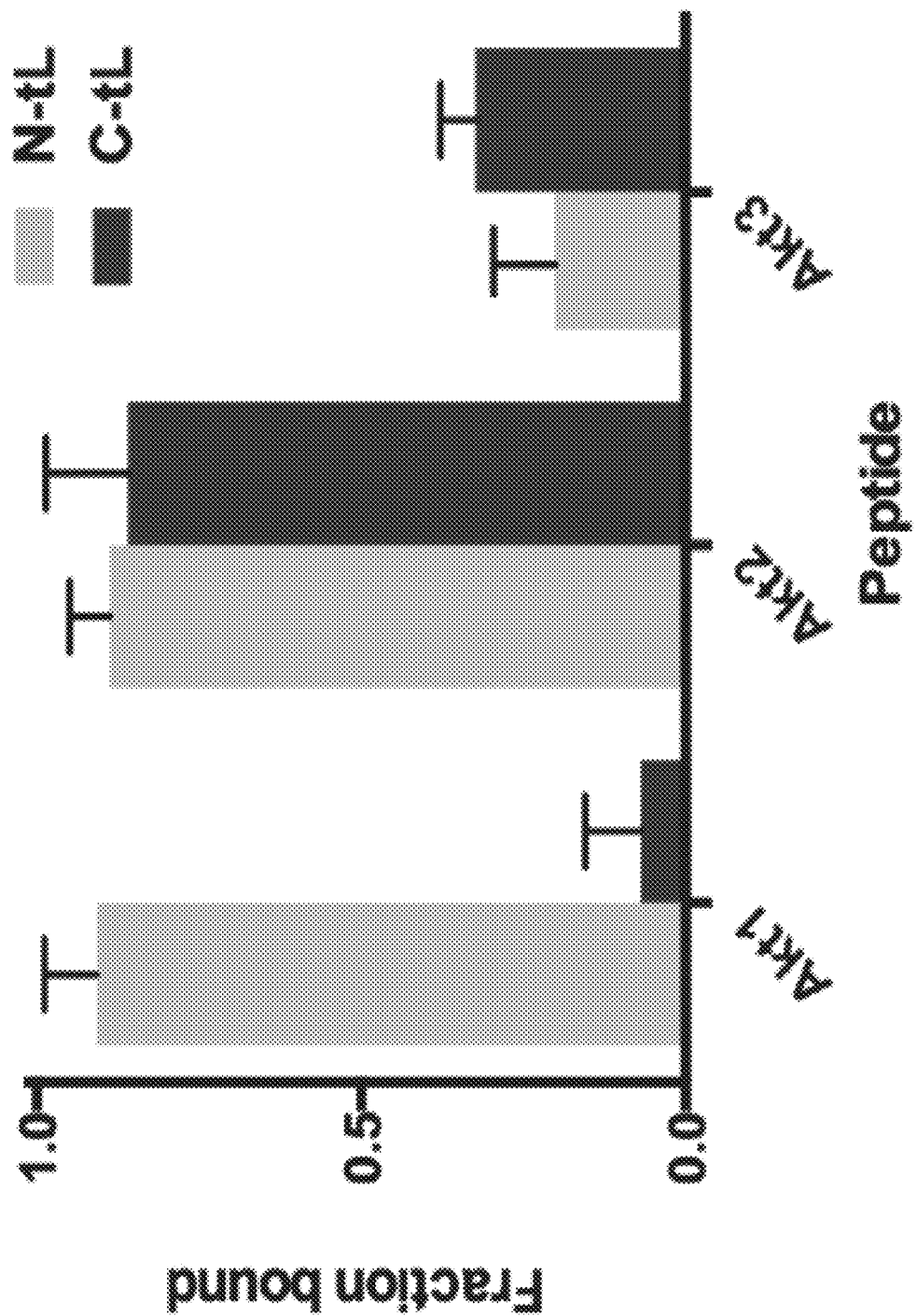
FIG. 23: A. ELISA assays in which the PCC Agents are utilized as either as surface-localized capture agents (for N-tL, C-tL) or as the detection agent (for mono-L, bi-L). Such assays provide relative affinity measurements, which are given as EC50 values in the key. B. C-tL has significant selectivity for the Akt2 epitope (450-481) compared to the corresponding regions in Akt1 (449-480) and Akt3 (448-479). C. C-tL distinguishes the full length Akt2 from isoform proteins Akt1 and Akt3. D. The 32 amino acid long C terminal fragment from Akt2, Akt1 and Akt3. The hydrophobic motif is highlighted in blue. pS refers to phosphoserine. E. C-tL is selective for pAkt2 over inactive Akt2. F. Selectivity assays: Biotinylated ligands or biotinylated pS473 antibody is immobilized on streptavidin-agarose and treated with OVCAR3 cell lysate. The eluents are stained with a pan-Akt antibody or pS473 Akt antibody. N-tL immunoprecipitates more Akt, irrespective of its phosphorylation state, but C-tL and N-tL immunoprecipitate comparable amounts of active pS473 Akt.
Figure 23C:
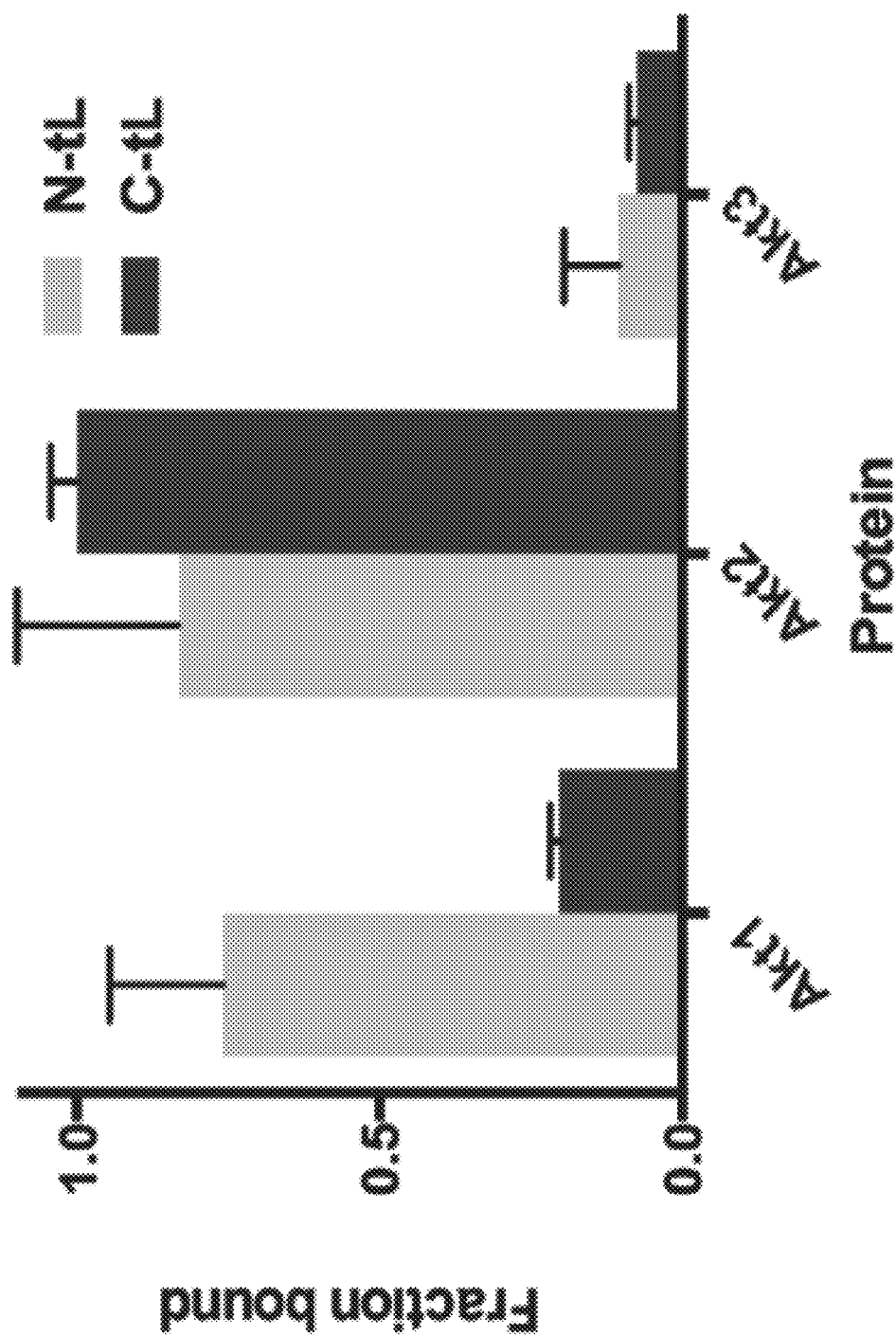
Figure 23F:
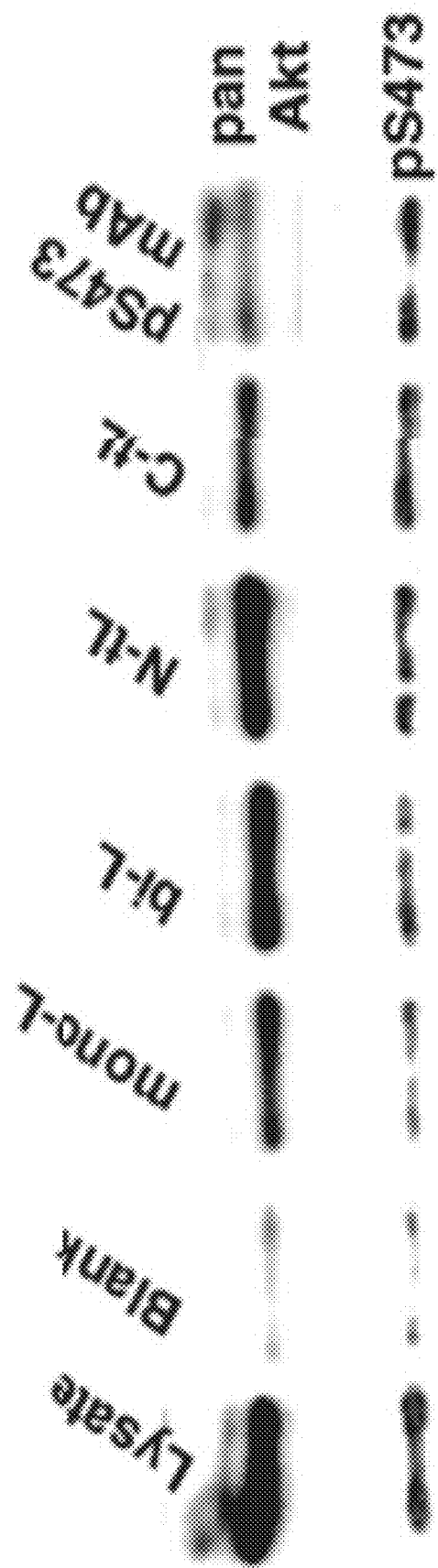
Figure 24:
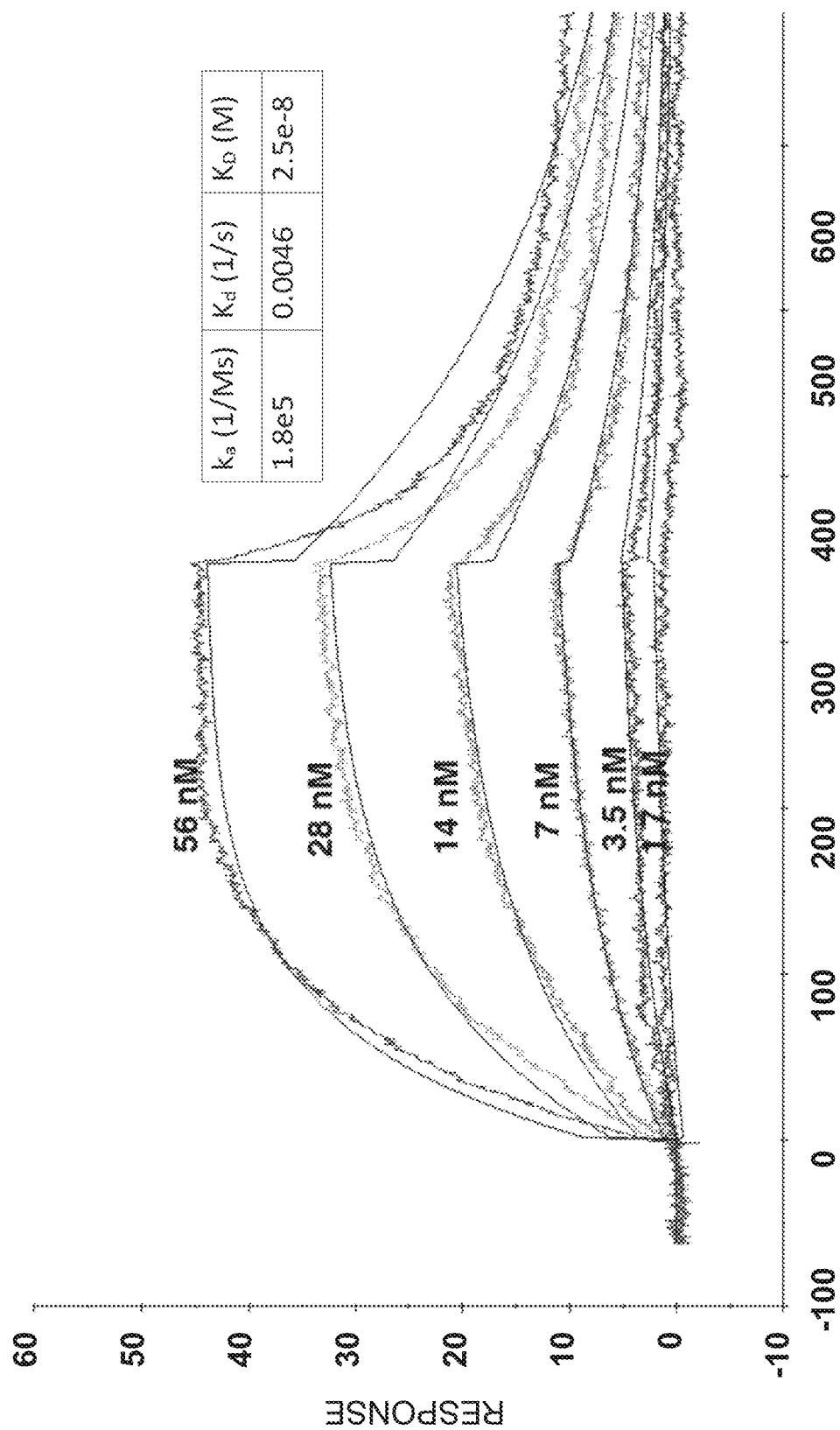
FIG. 24: Binding affinities of N-tL from Surface Plasmon Resonance (SPR) experiment. Sensorgrams from Surface Plasmon Resonance (SPR) experiment, immobilizing N-tL on SA chip and using Akt2 protein as the analyte. A. The data were fit to a simple 1:1 binding model using global analysis in Biacore T100 Evaluation software. The equilibrium dissociation constant KD is 25 nM, which is in close agreement with the ELISA EC50 value of 19 nM.
Figure 25:
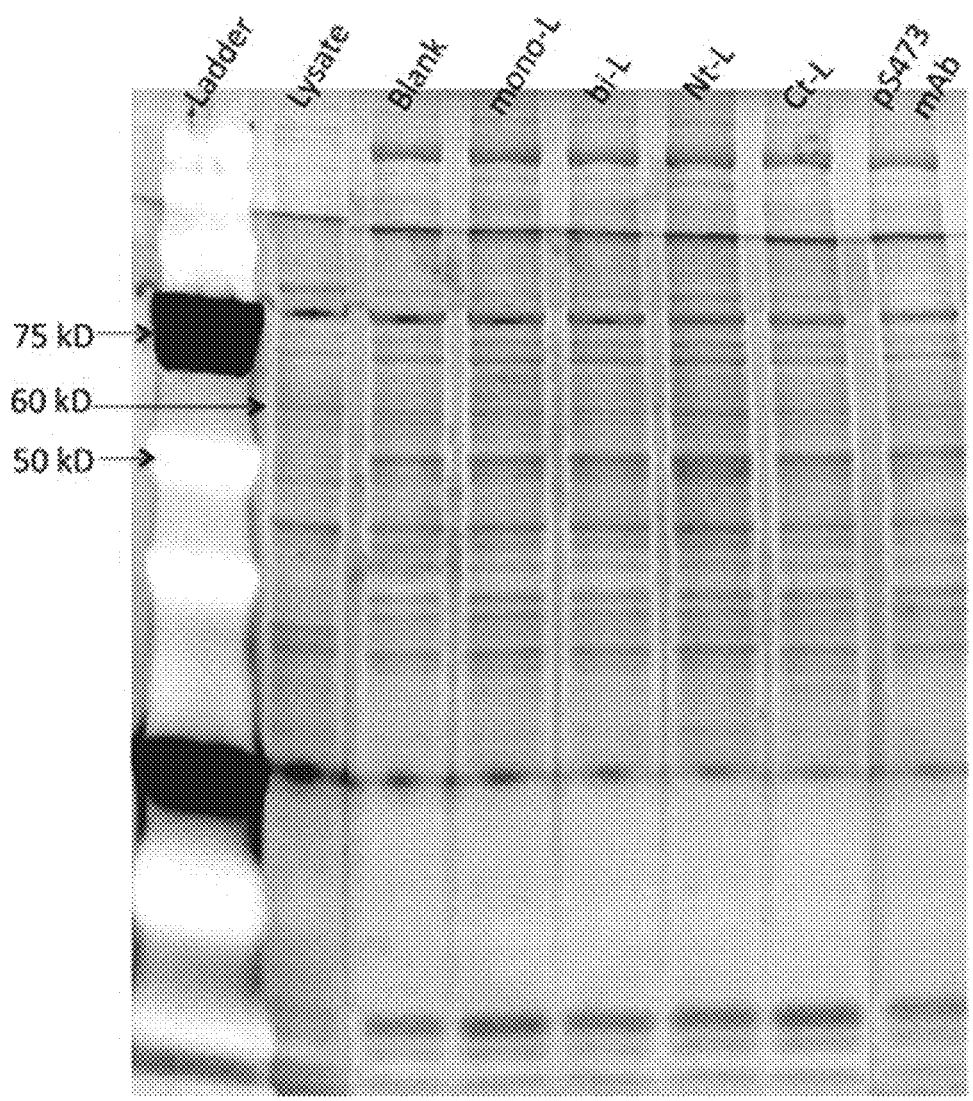
FIG. 25: Coomassie staining of gel from immunoprecipitation by different ligands/antibody. The biotinylated ligands (blank, mono-L, bi-L, N-tL, C-tL) or biotinylated antibody (pS473 mAb) are immobilized on streptavidin-agarose beads. The cell lysate (lysate) is directly diluted in the sample buffer and ran as a control. The band at 60 kD is for the Akt protein. All the eluted samples (blank to pS473 mAb) have similar non-specific protein pulldown.

Both triligands were tested for binding selectivity by comparing against the C-terminal 32-mer fragments of Akt1, Akt2, and Akt3, as well as those full-length proteins (FIGS. 23B, 23C). ELISA-type assays were done in triplicate against a single concentration of the $His_6$ (SEQ ID NO:28) tagged peptide or the $His_6$ (SEQ ID NO:28) tagged full protein. Akt1, Akt2 and Akt3 are >85% identical in the kinase domain and are highly homologous near the S474 residue (FIG. 23D). Both triligands exhibit selectivity at the peptide and full protein level, with the C-tL exhibiting 5:1 and 10:1 selectivity over full-length Akt1 and Akt3 respectively. This result confirms the selectivity of the epitope targeting approach. The selectivity of the triligands against p-Akt2 relative to Akt2 was also tested, and a high (5:1) selectivity for only the C-tL (FIG. 23E) was found, which was also observed for immunoprecipitation assays. For those assays, the biotinylated ligands, or the biotinylated pS473 mAb were immobilized on streptavidin agarose resin and treated with OVCAR3 cell lysate overnight. After stringent washing, the samples were eluted off the beads and run on a gel. When the eluted proteins (Coomassie stain FIG. 25), were treated with a pan Akt antibody that detects all Akt isoforms, the increased affinity from mono-L to N-tL is evident, while C-tL has lower signal than N-tL. But when the eluent is treated with an antibody specific for phosphorylated S473 (S474 in Akt2), C-tL shows an increased immunoprecipitation of p-Akt2.

Figure 26A:
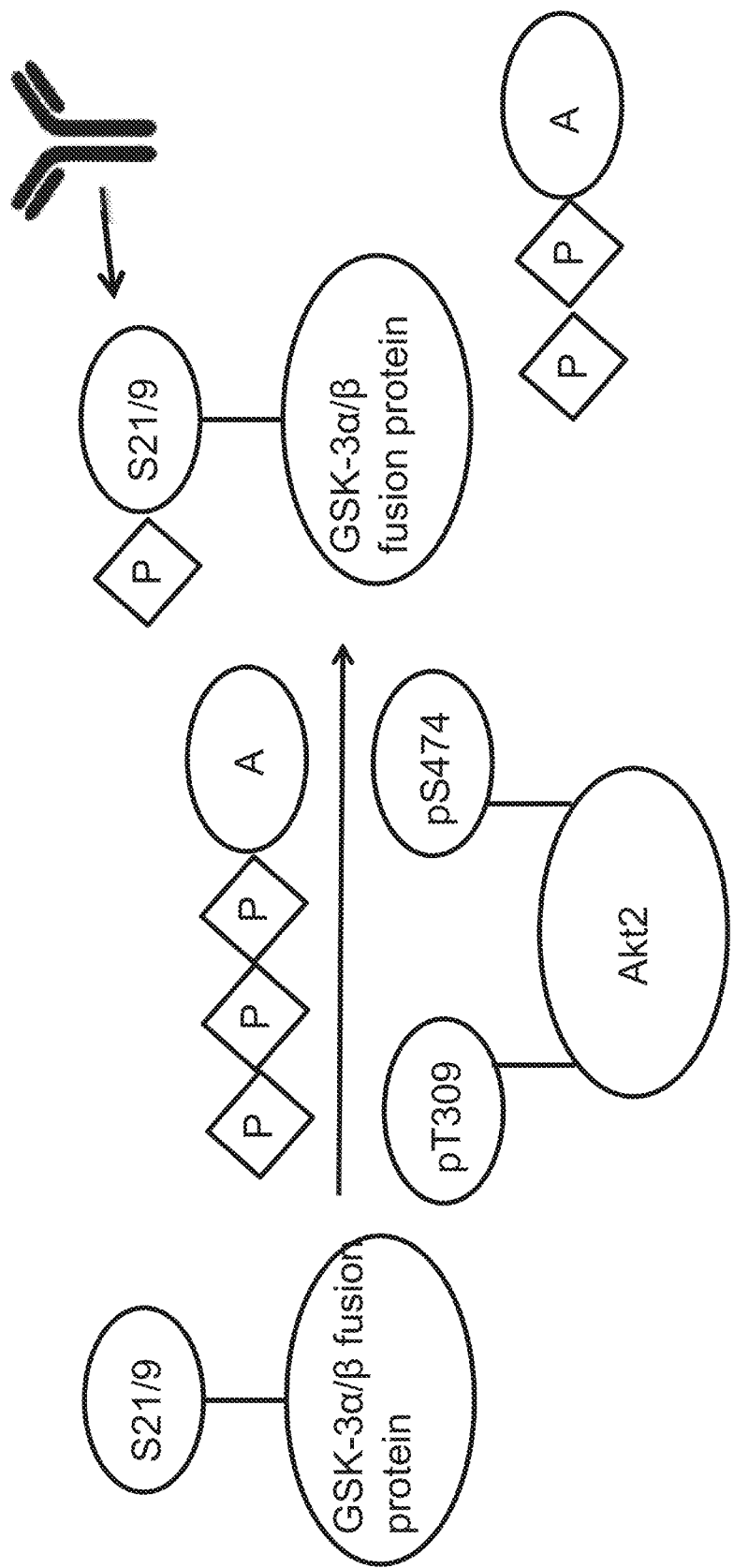
FIG. 26: The influence of the PCC Agents on the enzymatic activity of active Akt2. A. The activity of Akt2 directly influences the phosphorylation of the GSK-3α/β fusion protein at Ser9/Ser21. Thus, the level of phospho-GSK-3α/β provides a readout for the activation or inhibition Akt2 by a molecular probe. B. Western blot analysis of p-GSK-3α/β levels show that, relative to the DMSO control, the N-tL and the commercial anti-phospho-S473 antibody activate Akt above baseline. The C-tL inhibits Akt2 kinase activity.
Figure 27:
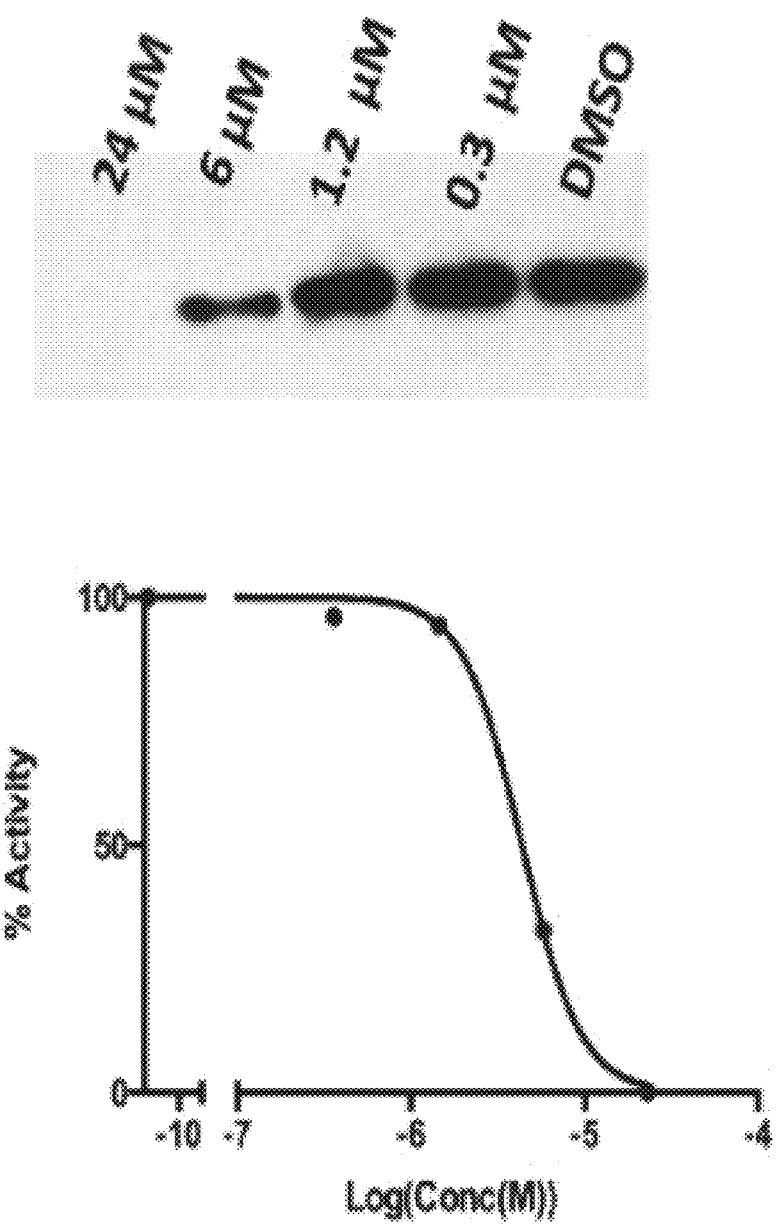
FIG. 27: Inhibition of kinase activity of the Akt2 protein when treated with C-tL. Inhibition of kinase activity of the Akt2 protein when treated with C-tL. The in vitro phosphorylation of GSK3α/β substrate by active Akt2 is inhibited when treated with increasing concentrations of the C-tL ligand. The solutions were run on a gel and visualized by treatment with pGSK3α/β Ser 21/9 antibody. The western blot image was scanned and the signal corresponding to different concentrations of C-tL was quantitated using ImageJ. The density was normalized to the signal for no inhibitor (DMSO control) to generate an activity percentage value curve in graphPad Prism 6.0. An EC50 value of 4 μM is obtained from the curve using non-linear regression.

A non-radioactive Akt2 kinase assay kit was utilized to estimate the influence of the ligands on the kinase activity of Akt2. For this assay, active Akt2 is combined with its downstream effector Glycogen Synthetase Kinase (GSK)-3α/β substrate, ATP, and one of the peptide ligands, or DMSO control. The level of phosphorylation of GSK-3α/β provides a readout for the Akt2 kinase activity (FIG. 26A). The N-tL was found to activate Akt2, as did the commercial pS473 antibody (FIG. 26B). By contrast, the C-tL inhibits Akt2, with an $EC_{50}$ of around 4 µM, as estimated from the Western blotting assays of the Akt2 induced phosphorylation of the GSK-3α/β substrate, at varying C-tL concentrations (FIG. 27). Thus, the enzymatic activity of Akt2 is hypersensitive to perturbations near the C-terminus. This delicately balanced structure-function relationship between S474 and the Akt enzymatic activity apparently works in both directions: ATP-competitive inhibitors like A-443654 cause paradoxical hyper-phosphorylation of Akt at both Thr308 and Ser473, and thus lead to protein reactivation after inhibitor dissociation.

Example 10: Development and Characterization of Tri_a and Tr_i

Two PCC agent triligands, tri_a and tri_i, which were developed using iterative in situ click chemistry from the same epitope targeted 5-mer peptide anchor ligand, were respectively shown to activate and inhibit Akt enzymatic activity in in vitro kinase assays. The modularity of these synthetic PCC Agents was utilized to promote their delivery into live carcinoma cell lines. The previously observed allosteric activating and inhibiting effects of tri_a and tri_i on Akt kinase activity was found to translate into live cells. Both PCC agents were modified to deliver destruction signals to the Akt protein within the cells, allowing the activation, inhibition, or destruction of a protein target using variations of a single synthetic ligand.

Example 11: Experimental Methods

Example 11.1: General Protocol for Solid Phase Peptide Synthesis

Peptides were synthesized on Rink Amide MBHA, Biotin Novatag, and Sieber Amide resin either manually, on a Liberty1 Microwave Peptide Synthesizer (CEM), or on a Titan 357 Automatic Peptide Synthesizer (AAPPTec). Peptide coupling reactions were done in NMP with 2 equivalents of amino acid, 2 equivalents of HATU and 6 equivalents of N,N-Diisopropylethylamine (Sigma). For removal of Na-Fmoc protecting groups, a solution of 20% piperidine in NMP was used.

Example 11.2: Acylation

The resin was treated twice for ten minutes with a solution of anhydrous acetic anhydride and DIEA in NMP (acetic anhydride:DIEA:Peptide; 40:20:1) at room temperature. Excess reagent was removed by washing five times successively with NMP.

Example 11.3: Cleavage of Side Chain Protected Peptides

The peptides were synthesized on Sieber Amide resin and cleaved by washing three times for one minute with 1% TFA/DCM, and finally washed with DCM. The acidic peptide solution was neutralized using 2 equivalents of DIEA followed by removal of the solvent by rotary evaporation. The remaining semisolid was dissolved in filtered DMSO, HPLC grade acetonitrile and double distilled water, and purified via HPLC.

Example 11.4: Cleavage of Side Chain Deprotected Biotin Linker Peptide

The peptides were synthesized on Biotin Novatag resin. The dried resin was then treated with a TFA cleavage solution of 95% TFA, 2.5% $H_2O$, and 2.5% triethylsilane for two hours at room temperature. The cleavage solution was filtered to remove the resin and added dropwise to an ice-cooled solution of diethyl ether.

Example 11.5: Cleavage of TAT-Containing Peptides

TAT-containing peptides were synthesized on Rink Amide MBHA resin. The dried resin was then incubated with a TFA cleavage solution of 80% TFA, 10% thioanisole, 5% $H_2O$, 5% triethylsilane for 3 hours at room temperature. The cleavage solution was filtered to remove the resin and added dropwise to a cooled solution of diethyl ether.

Example 11.6: HPLC Purification of Peptides

All peptides were purified using a preparative or semi-preparative scale HPLC with a C18 reverse phase column. A gradient of double distilled water and HPLC grade acetonitrile and 0.1% TFA was used for all purifications.

Example 11.7: Protocol for On-Bead Copper (Cu) Catalyzed Azide Alkyne Cycloaddition (CuAAC) Click Reaction On-bead Cu catalyzed click reactions were performed with the azide on bead and the alkyne in solution. The resin was treated with 2 equivalents of the relevant alkyne, 1.5 equivalents of CuI (Sigma) and 2.5 equivalents of ascorbic acid (Sigma), in a solution of 20% piperidine in DMF. The reaction was performed overnight at room temperature. Excess copper was removed from the resin by washing with a Cu chelating solution (5% (w/v) sodium diethyl dithiocarbamate, 5% (v/v) DIEA in DMF).

Example 11.8: Removal of Dde Protecting Group

For removal of Dde protecting groups, resin-bound peptide was washed with a solution of 2% hydrazine in DMF three times for ten minutes.

Example 11.9: Mass Spectrometry Analysis

All intermediate and final peptides were analyzed via MALDI-TOF-MS using a Voyager DE-PRO MALDI TOF-MS system (Applied Biosystems). Peptides were dissolved in 50:50 water/acetonitrile with 0.1% trifluoroacetic acid at a final concentration of 10 μmol/μL. 1 μL of the peptide sample was then added to 10 μL of a saturated solution of MALDI matrix, either α-cyano-4-hydroxycinnamic acid or Sinapinic Acid, in 50:50 water/acetonitrile with 0.1% trifluoroacetic acid and analyzed via MALDI-TOF MS.

Example 11.10: Biological Assays and Microscopy

Example 11.10.1: Cell Culture

All cell lines were purchased from American Type Culture collection and cultured under conditions specified by the provider.

Example 11.10.1: Immunoblotting

Western blots were performed according to standard protocols. Briefly, cells were lysed with cell lysis buffer (Cell Signaling Technology) containing protease and phosphatase inhibitors (Cell Signaling Technology). Cell lysates were quantified with a Bradford protein assay (Thermo Scientific) and prepared for gel electrophoresis in Laemmli sample buffer and reducing agent. 20 μg of cell lysate were added to precast polyacrylamide gels (Bio-Rad) and proteins were separated by electrophoresis followed by transfer to PVDF membrane. Membranes were then blocked and probed with primary antibodies followed by horseradish peroxidase-conjugated secondary antibodies. The following antibodies were used according to manufacturer protocol: p-GSK3β (Cell Signaling, 9323), GSK3 β (Cell Signaling, 12456), AKT (Cell Signaling, 4691), p-AKT (S473) (Cell Signaling, 4060), Actin (Cell Signaling, 8456), HRP-linked Anti-rabbit IgG (Cell Signaling, 7074). The bands were visualized by chemiluminescence (Thermo Scientific).

Example 11.10.2: XTT Assay

The XTT assay kit was purchased from Cell Signaling Technology (#9095) and used according to manufacturer protocol. Briefly, 1×10⁴ cells were seeded in a 96-well plate. The following day, cells were serum starved and treated with capture agent. Following treatment, the XTT tetrazolium salt was added to the media and after 1 hour the absorbance at 450 nm was measured in a 96-well plate reader.

Example 11.10.3: In-Cell ELISA Assay

In-cell ELISA kits were purchased from Thermo Scientific (#62215) and used according to manufacturer protocol. Briefly, 1×10⁴ cells were seeded in 384-well plates and allowed to attach overnight. The following day, cells were serum starved and treated with capture agent. Following capture agent treatment, cells were fixed, permeablized, blocked, and then stained with primary and HRP-conjugated secondary antibody and developed with colorimetric peroxidase substrate. The absorbance was measured at 450 nm to quantify the protein.

Example 11.10.4: Fluorescence Microscopy

Cells were seeded onto chambered coverglass slides (Sigma) and allowed to attach overnight. The following day, cells were serum starved and treated with fluorescent capture agent. Live cells were then imaged using a Zeiss LSM 5 Exciter microscope.

Example 12: Synthesis of N-Terminal Activating Triligand

Figure 28:
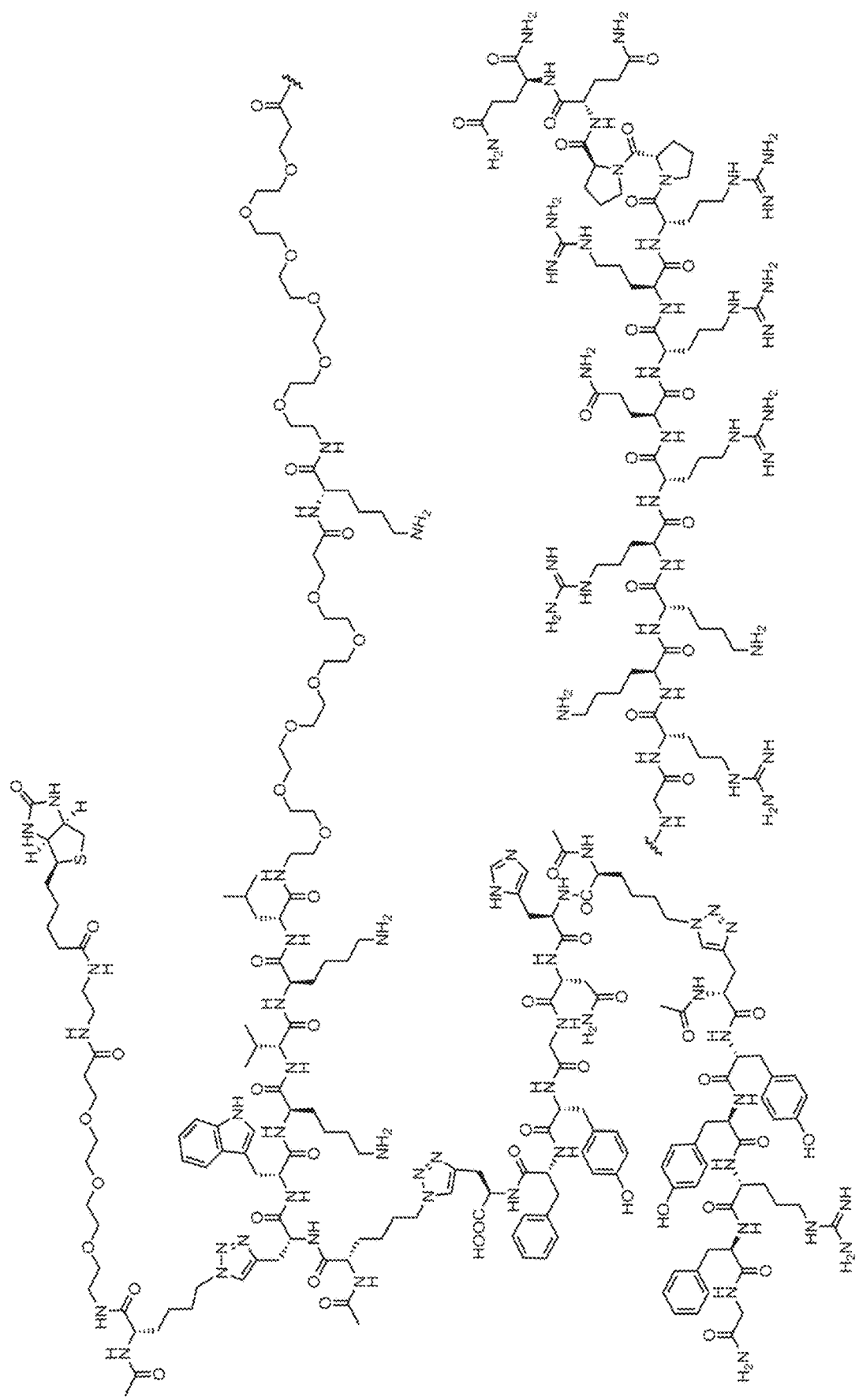
FIG. 28: The structure of the N-terminal triligand conjugated to HIV-1 Tat 48-61 used for activation assays (see Example 16).

For the synthesis of the N-terminal triligand the HIV-TAT sequence $H_2N$-GRKKRRQRRRPPQQ-$CONH_2$ (SEQ ID NO:16) was synthesized on rink amide MBHA resin using standard SPPS conditions. Fmoc-Peg5-COOH was then coupled to the N-terminus of the resin-bound TAT peptide with 1.5 equivalents of Peg5, 1.5 equivalents of HATU and 4.5 equivalents of DIEA. Following the Peg5 coupling and subsequent Fmoc deprotection Fmoc-Lysine(Dde)-OH was then coupled using standard conditions. After the Lys(Dde) coupling and deprotection a second Peg5 group was added. The N-terminal triligand was then synthesized on the resin bound Peg5-Lys(Dde)-Peg5-TAT peptide as described above. The Dde group was then removed and the peptide was either cleaved/deprotected and purified for assays or further modified at the epsilon amino group of the lysine side chain at the linker region. The TAT-conjugated triligands (FIG. 28) were cleaved from the resin in 80:10:5:5 TFA:thioanisole:TES:H2O for 2.5 hours. Expected [M+H]+=6047.1, Observed [M+H]+=6049.9

Example 13: Synthesis of Fluorescently Labeled N-Terminal Activating Triligand

Figure 29:
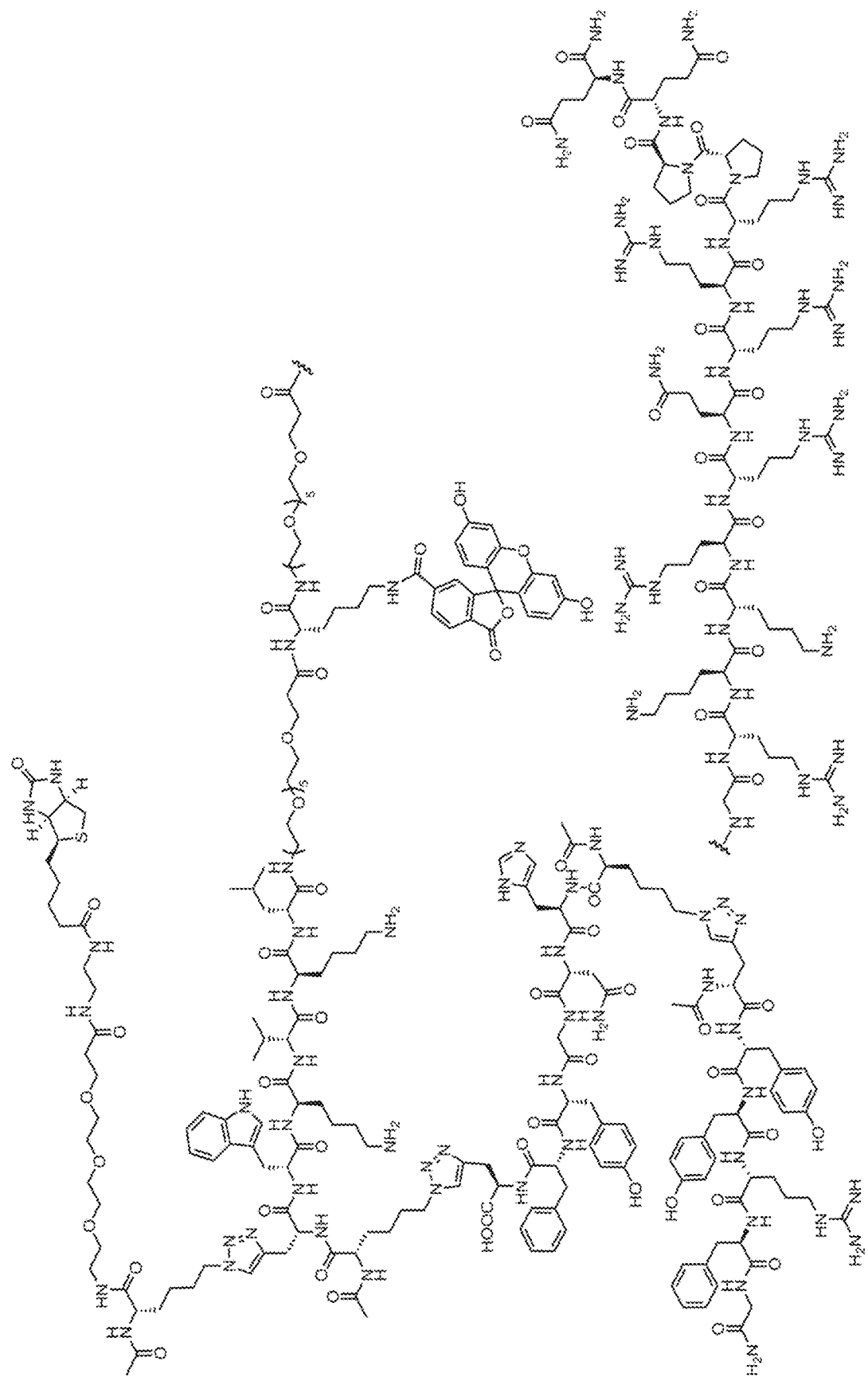
FIG. 29: The structure of the fluorescein-labeled N-terminal triligand used for imaging experiments (see Example 16). Fluorescein was added to the ε-amino group of a lysine residue in the linker region.

To resin-bound N-terminal triligand described above, 5-Carboxyfluorescein was coupled to the epsilon amino group of the lysine side chain at the linker region. The coupling reaction was performed with 1:1.5:1.5:4.5 ratios of peptide:5-Carboxyfluorescein:HATU:DIEA. The peptide (FIG. 29) was then cleaved and purified with the same conditions as the unlabeled N-terminal triligand. MALDI-TOF MS: Expected [M+H]+=6407.4, Observed [M+H]+=6408.7

Example: 14: Synthesis of N-Terminal Triligand with Hif-1α Degradation Signal

Figure 30:
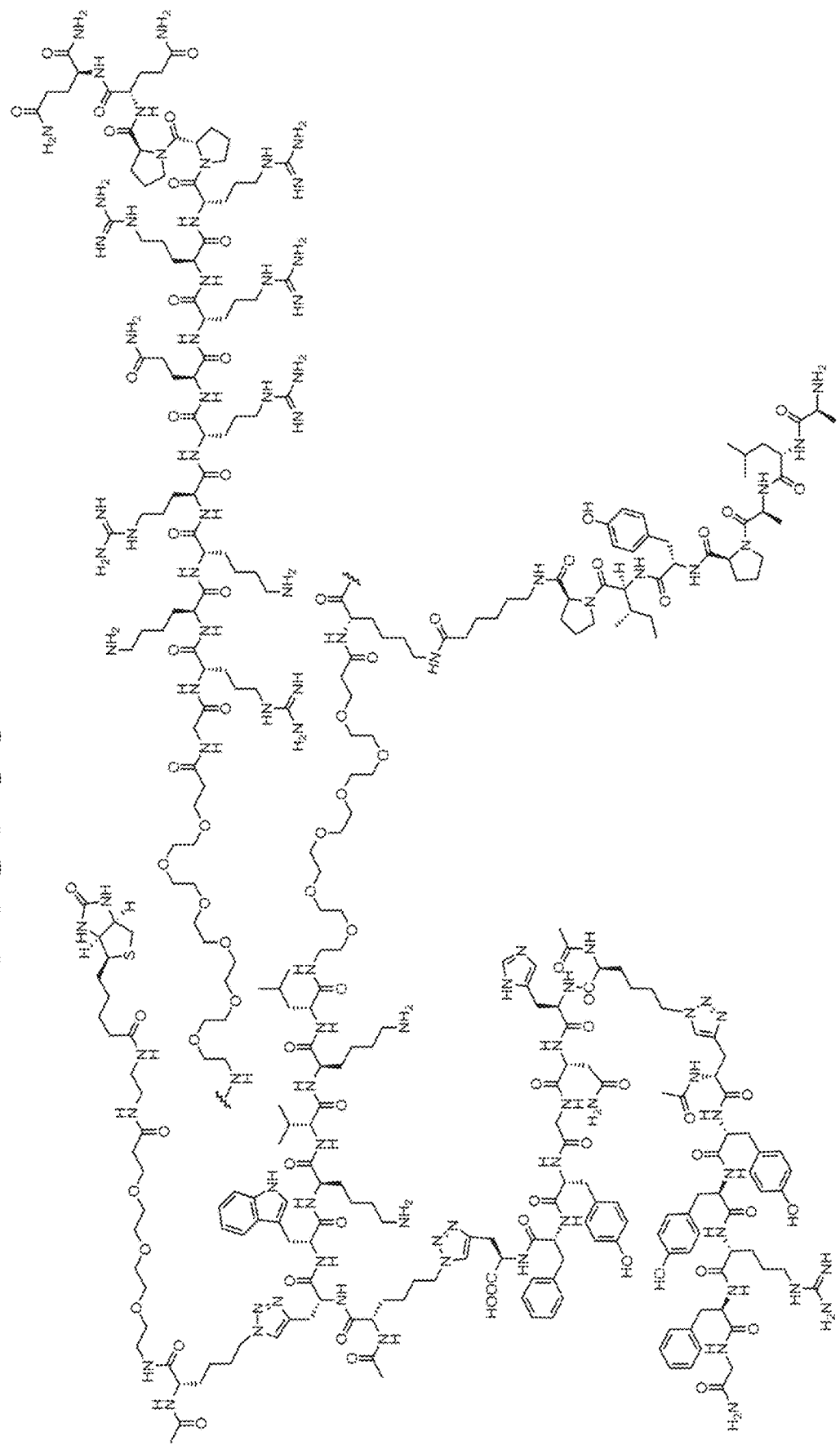
FIG. 30: The structure of the N-terminal triligand functionalized with the ubiquitination tag used in the degradation assays (see Example 16).

To resin-bound N-terminal triligand previously described, 6 aminohexanoic acid (Ahx) followed by the Hif-1α degradation peptide ALAPYIP (SEQ ID NO:27) were coupled to the epsilon amino group of the lysine side chain at the linker region using standard SPPS conditions. The peptide (FIG. 30) was then cleaved and purified with the same conditions as the unlabeled N-terminal triligand. MALDI-TOF MS: Expected [M+H]+=6885.1, Observed [M+H]+=6885

Figure 31:
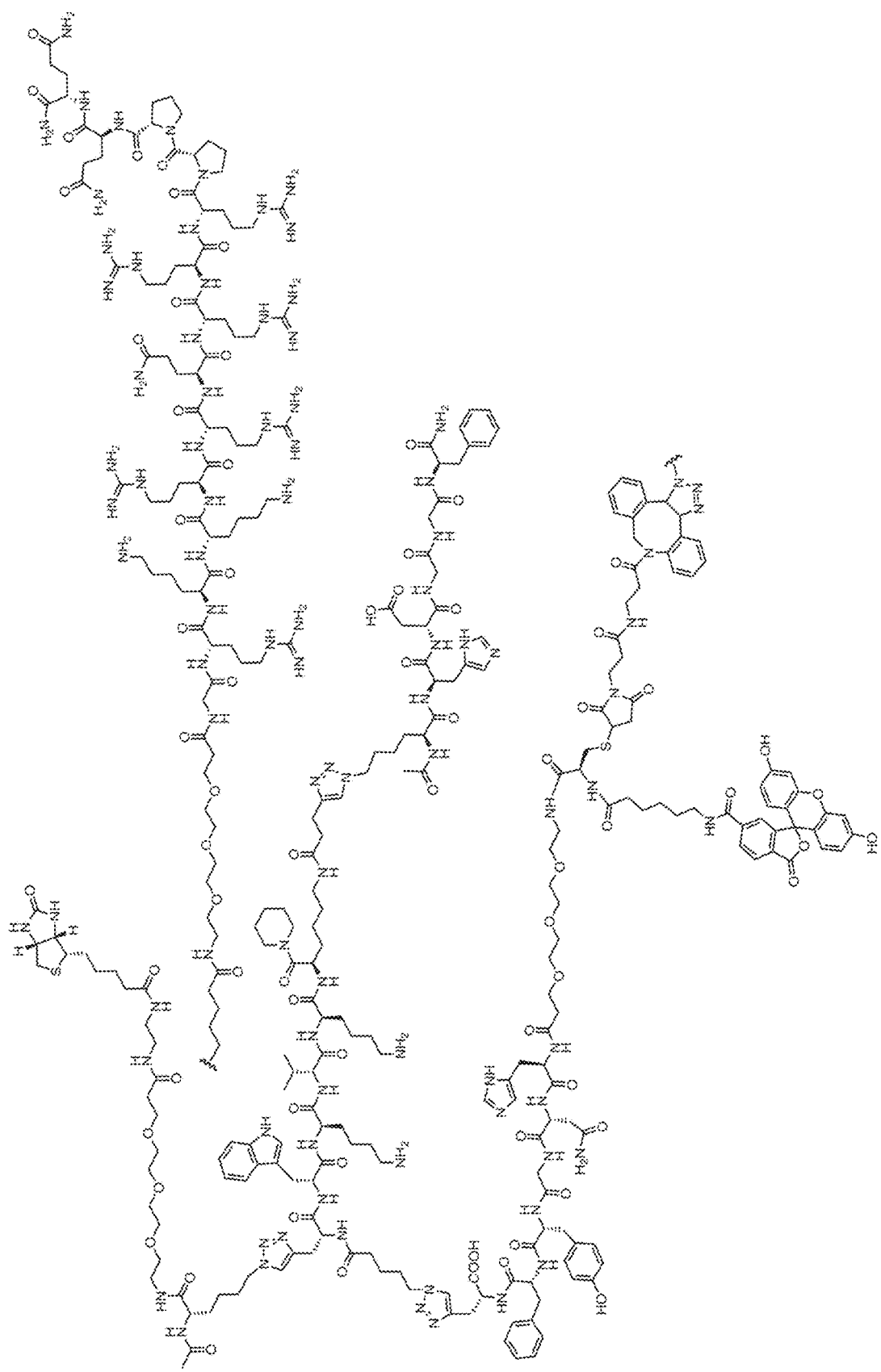
FIG. 31: The structure of the C-terminal triligand used in inhibition experiments (see Example 16). The C-terminal triligand includes a fluorescein label.

Unlabeled C-terminal triligand (FIG. 31) was synthesized as previously reported. Fmoc-Peg2-COOH was then coupled to the N-terminus of the resin-bound peptide with molar ratios of 1:1.5:1.5:4.5 peptide:Peg2:HATU:DIEA. Cysteine followed by Ahx were then coupled using standard conditions and 5-carboxyfluorescein was coupled as before resulting in compound 1. Fluorescent C-terminal triligand was then cleaved with 95:2.5:2.5 TFA:H2O:TES and HPLC purified. Dibenzocyclooctyne-maleimide (Sigma) was then coupled to the cysteine thiol group as reported to yield cyclooctyne C-terminal triligand 2.

Azide-containing TAT peptide 3 was synthesized using standard conditions and Fmoc-Peg2-COOH was coupled as before followed by addition of 5-azidopentanoic acid using standard coupling conditions. Resin-bound 3 was then cleaved and purified with conditions mentioned above. Peptides 2 and 3 were then clicked together as reported resulting in C-terminal triligand 4, which was then isolated by HPLC purification. MALDI-TOF MS: Expected [M+H]+=6599.3, Observed [M+H]+=6599.1

Example 15: Synthesis of C-Terminal Triligand with Hif-1α Degradation Signal

Figure 32:
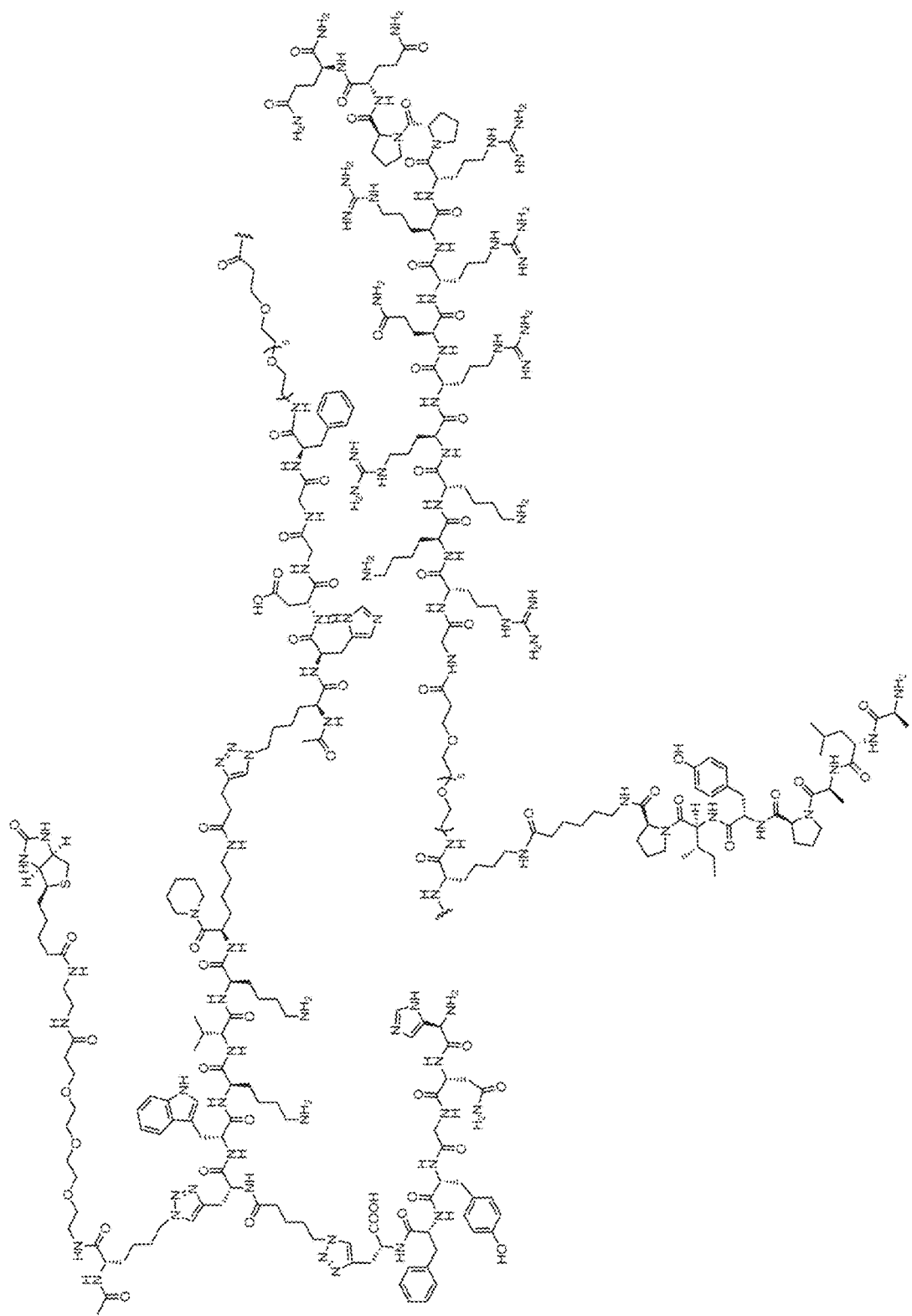
FIG. 32: The structure of the C-terminal triligand (blue) functionalized with the ubiquitination tag used in the degradation assays (see Example 16).

Resin-bound HIV-TAT peptide H2N-Peg5-Lys(Dde)-Peg5-GRKKRRQRRRPPQQ-CONH2 (SEQ ID NO:80) was synthesized as described above. The C-terminal triligand (FIG. 32) was then synthesized onto the TAT peptide as before. The ε-amino group of the Lys(Dde) in the linker region was then deprotected and the degradation sequence Ahx-ALAPYIP (SEQ ID NO:81) was added by SPPS as with the N-terminal triligand. [M+H]+=6641.81, Observed [M+H]+=6641.89.

Example 16: In Vitro Assays

Figure 33A:
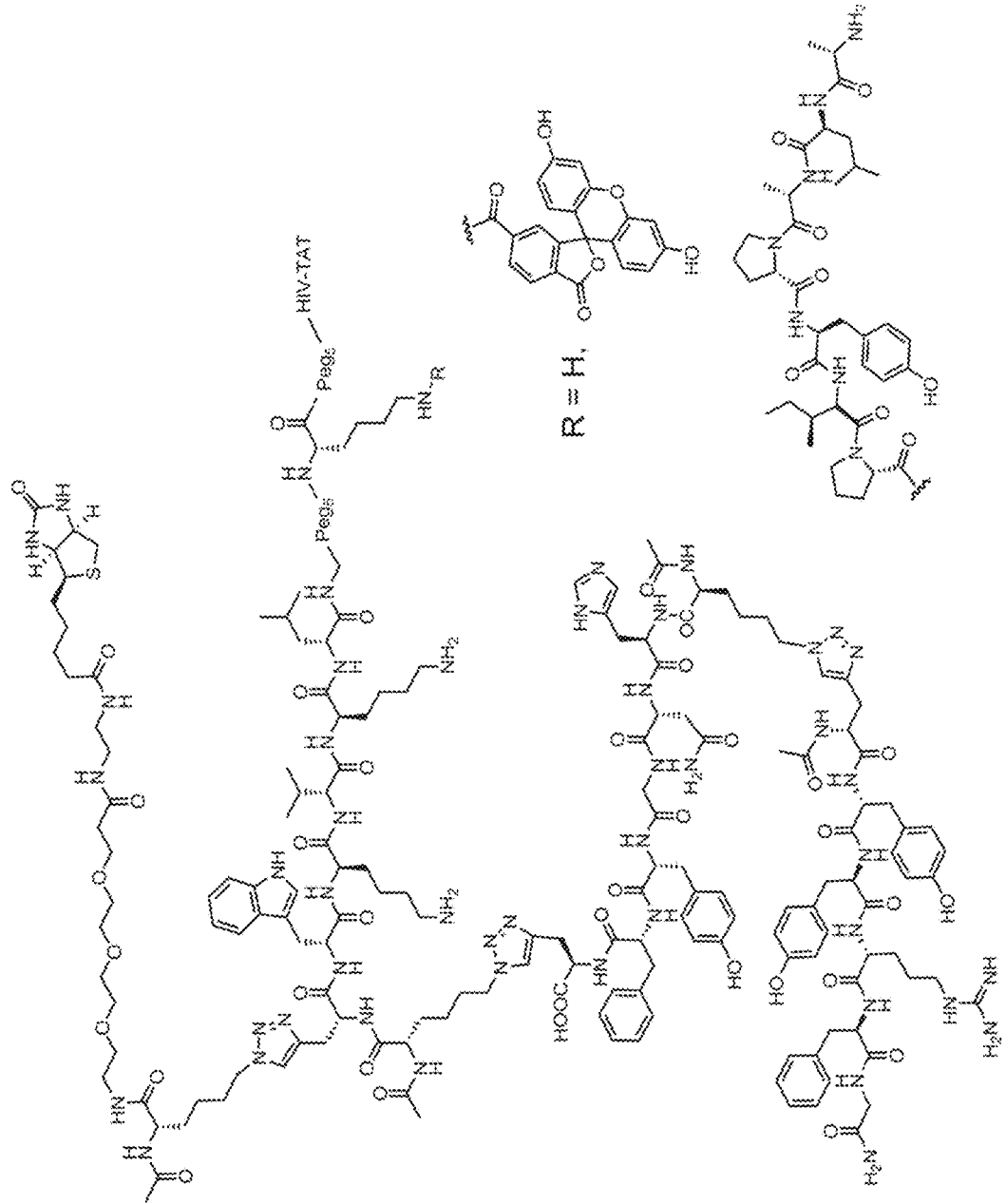
FIG. 33: A. Structure of Akt-activating N-terminal triligand, tri_a. The lysine residue between the PEG spacers can be further functionalized to include a fluorescein or the degradation-inducing Hif-1a peptide. B. Live cell confocal images of the fluorescein labeled capture agent delivered into U87 cells.
Figure 33B:
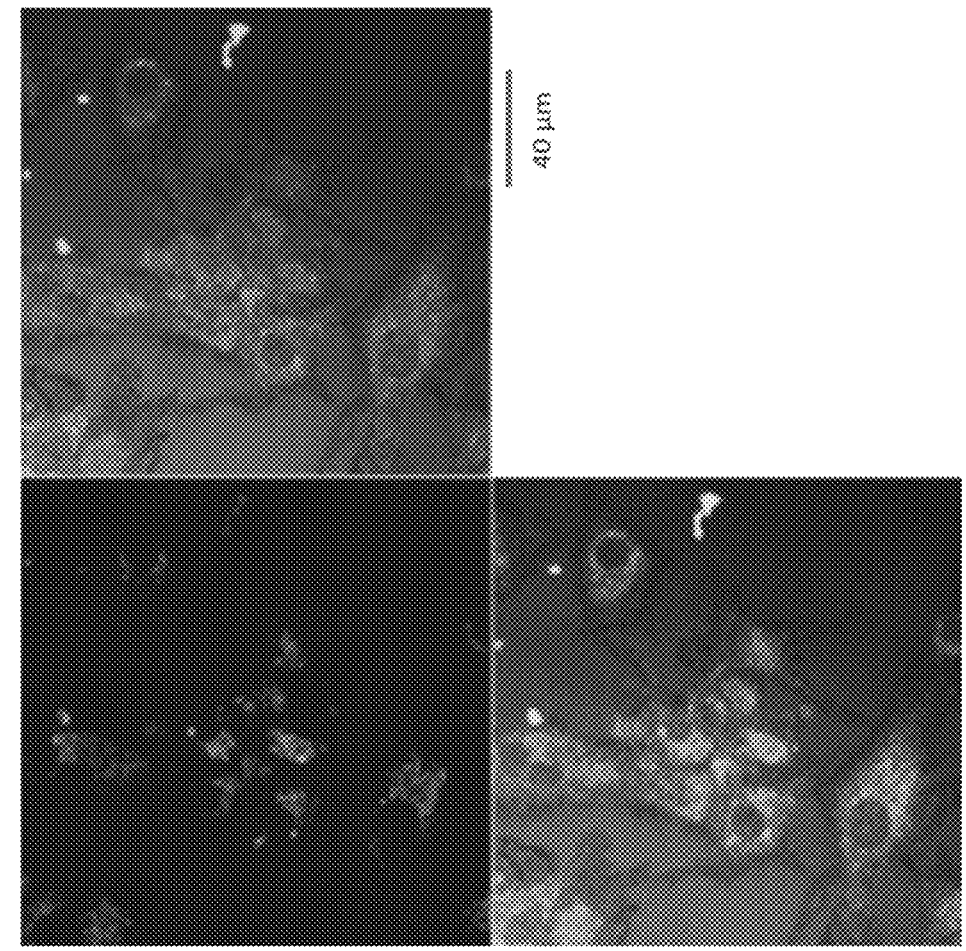

To investigate whether the PCC agents bind to Akt in live cells, the PCC agent was conjugated to the HIV TAT peptide, a cell penetrating peptide (CPP). Several studies have shown that CPPs efficiently penetrate cell membranes and allow CPP-bound molecules to enter cells. FIG. 33a shows the structure of TAT-conjugated tri_a, where the TAT sequence is separated from the capture agent by two PEG spacers placed on either side of a protected-lysine residue. This permits further functionalization as desired through the side chain via the ε-amino group (adding a dye, signaling peptide, etc.). To validate cellular uptake, U87 cells were treated with fluorescein-labeled tri_a (FIG. 33b) and simultaneous fluorescence and transmission images were acquired. U87 cells are particularly useful for imaging since they grow in a uniform monolayer. The molecule was able to efficiently penetrate the cell membrane and enter the cells. No fluorescence signals were detected outside the cells.

Figure 34A:
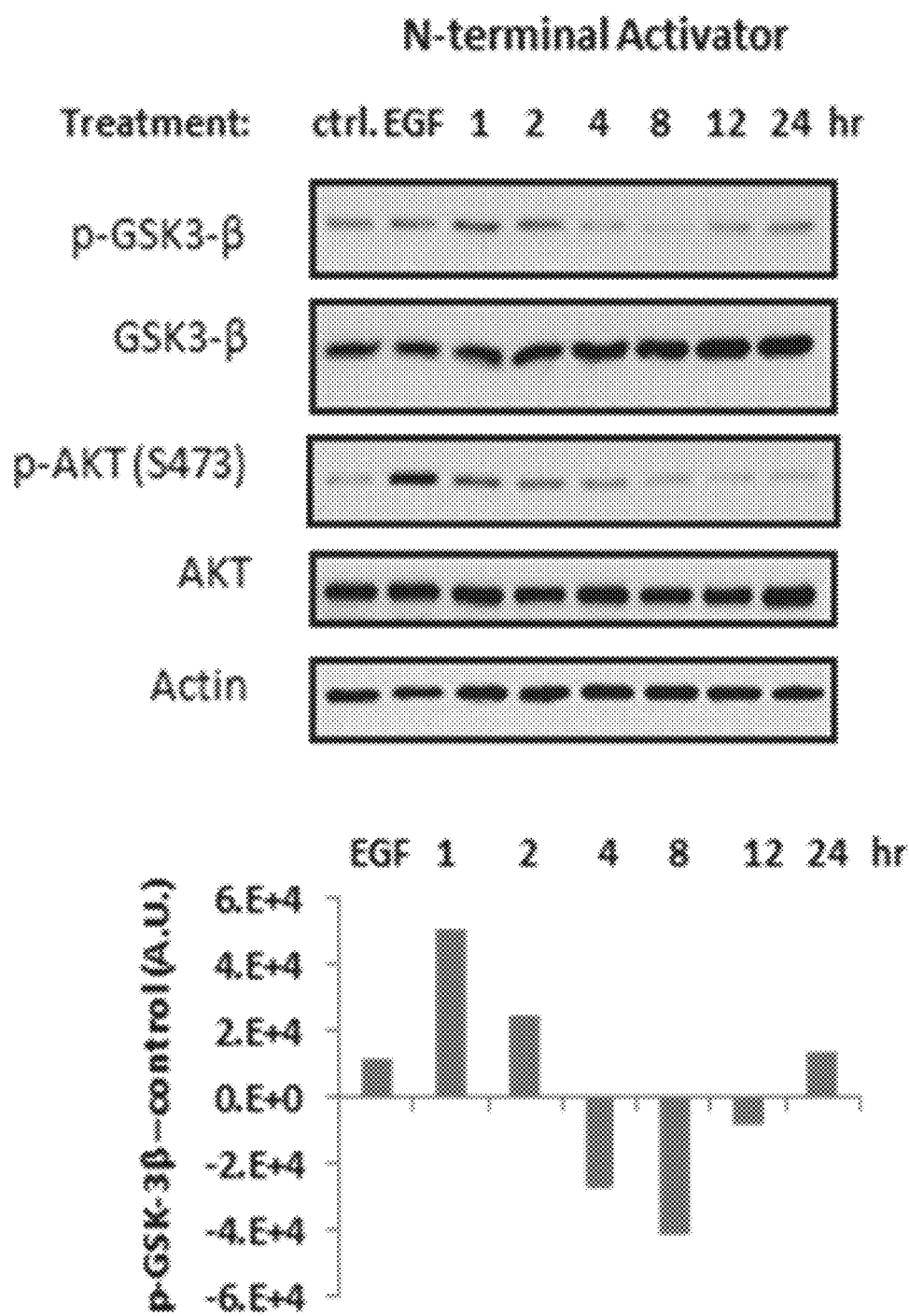
FIG. 34: (a) Western blots of SKOV3 cells treated with 50 μM tri_a Akt-activating capture agent. Densitometry was performed on the p-GSK-3β blot and the untreated control group was subtracted from the other samples and plotted on the graph below. The highest level of GSK3B phosphorylation is seen after 1 hour treatment with the capture agent. (b) XTT assay results from OVCAR and SKOV3 cells treated with 50 μM activating capture agent. Each cell line shows a significant increase in viability after 1 day treatment followed by a decline.
Figure 34B:
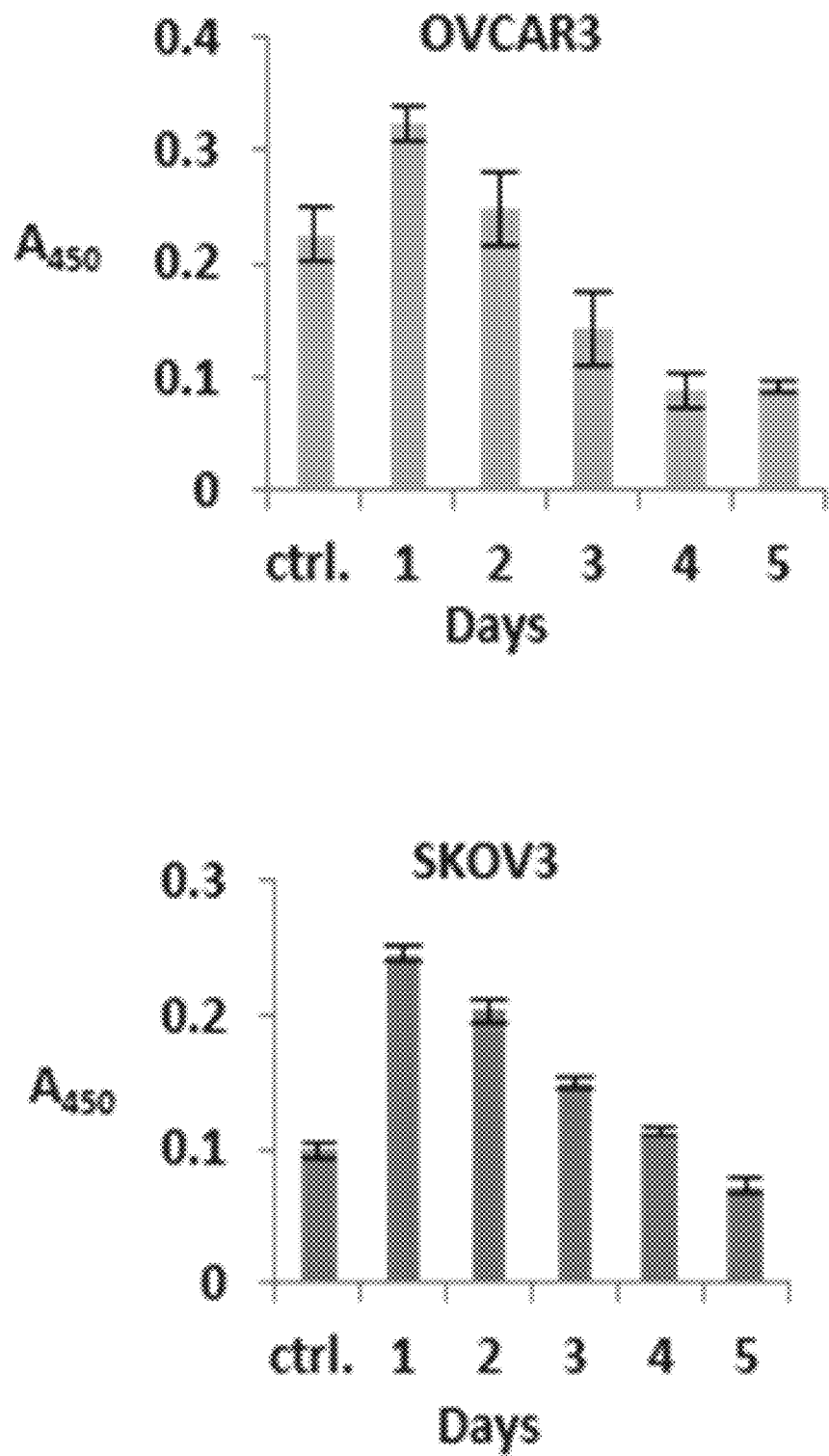

Once it was confirmed that the TAT-bound capture agent was entering cells, cellular assays were performed to assess the effects on the Akt signaling pathway. One particular Akt substrate is glycogen synthase kinase, GSK-3β, and its enzymatic activity can be monitored by studying GSK-3β phosphorylation. As ovarian cancer frequently displays aberrant Akt signaling, SKOV3 ovarian cancer cells were treated with TAT-coupled tri_a for various time intervals. They were then lysed simultaneously, and the relative levels of various proteins were measured via western blotting (FIG. 34a). Both untreated cells and EGF-stimulated cells were used as controls. The level of phospho (p)-GSK-3β was seen to increase after 1 hour of treatment, decrease over the next few hours, and finally increase once more—perhaps alluding to a feedback mechanism in the cell. The 1-hour treatment point shows a clear increase in the p-GSK-3β level relative to the untreated and EGF-stimulated cells, indicating that the capture agent is binding Akt and stimulating its enzymatic activity in cells. The p-Akt level initially increases and then steadily decreases over time. Notably, EGF-stimulated cells display a large increase in p-Akt, but the corresponding level of p-GSK-3β in EGF-stimulated cells is still lower than the initial levels in cells treated with tri_a.

XTT cell viability assays were also performed to assess the effects of Akt activation on the number of viable cells in a cell population. Dehydrogenase enzymes in live cells reduce XTT tetrazolium salt to a vividly colored formazan dye that can be used to quantify the number of viable cells. It was found that tri_a has a dramatic effect on both OVCAR3 and SKOV3 cell lines. Interestingly, the OVCAR3 cell viability appears to oscillate upon treatment. A sharp increase after 24 hours is followed by a steady decrease before finally stabilizing—once more suggesting a possible feedback mechanism. SKOV3 cells show an initial spike in cell viability after 24 hours, followed by a linear decrease with time. For the greater part of the time course, the number of live cells is consistently higher than the control. This could suggest that the cells are adapting to the effects of tri_a over time.

An increase in cell number after treatment with tri_a is consistent with previous studies that show that Akt activation promotes cell cycle progression during the G1 and G2 phases of the cell cycle. Additionally, activated Akt is known to be anti-apoptotic through direct inhibition of the pro-apoptotic Bad protein by phosphorylation at Ser 136, as well as pro-apoptotic transcription factors such as the FoxO and Myc family proteins. Such enhanced cell viability can be used in beneficial ways. Many pathological disorders are associated with aberrant cell death signaling, including various neurodegenerative diseases. Akt activation was recently shown to prevent neuronal cell death. Thus, an Akt activator might prove useful as a tool and potential therapeutic for disease-associated apoptosis abnormalities.

Figure 35A:
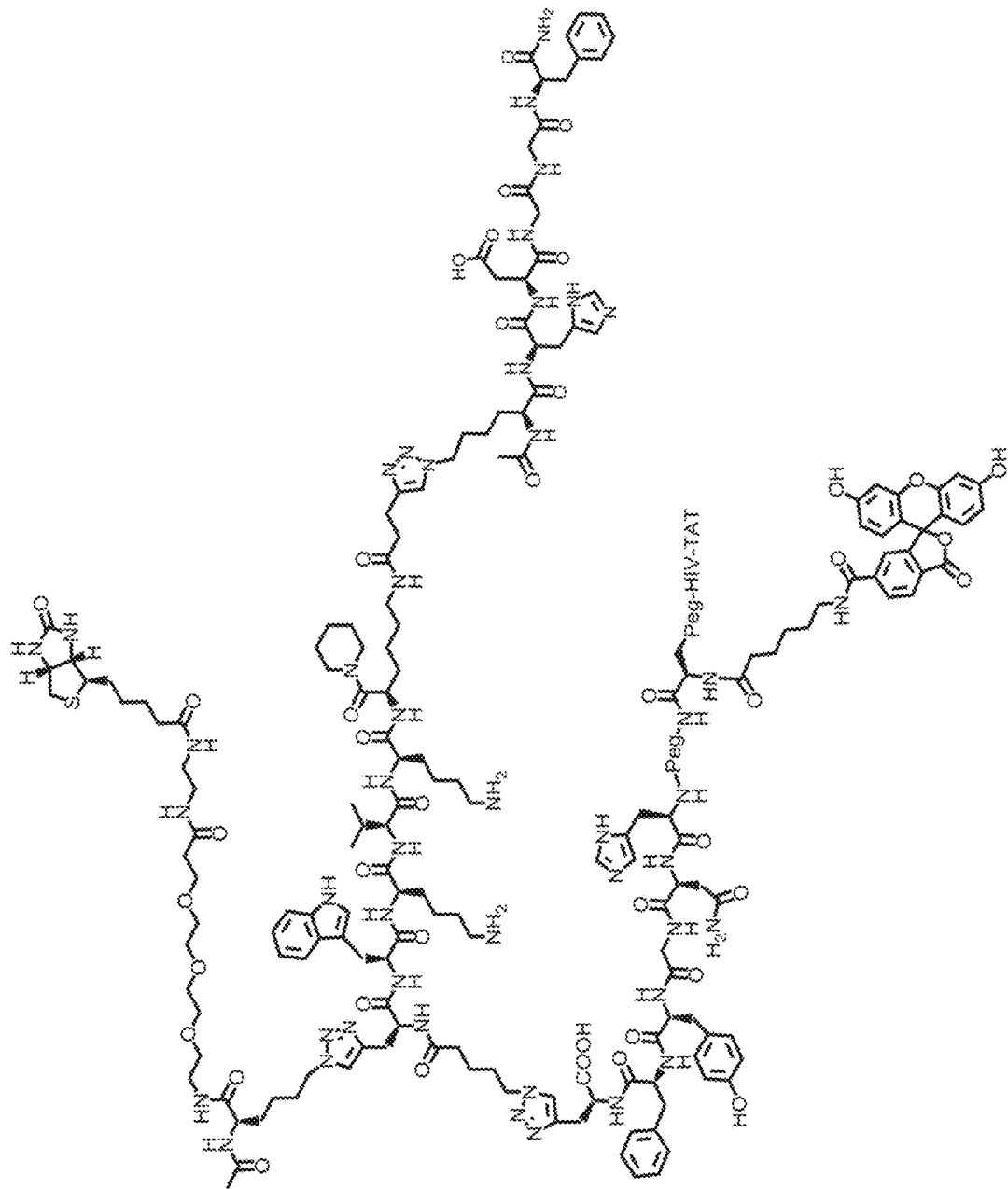
FIG. 35: (a) Chemical structure of Akt-inhibiting C-terminal triligand, tri_i. (b) Western blots of SKOV3 cells treated with 50 μM tri_i Akt-inhibiting capture agent. Cells were pretreated with inhibitor for various times, simultaneously stimulated with 100 ng/mL EGF for 10 minutes then lysed. 1, 6 and 12 hour inhibitor treatments show less phospho-GSK-3β than EGF stimulation alone. Densitometry was performed on the p-GSK-3β blot and the untreated control group was subtracted from the other samples and plotted on the graph below. (c) XTT assay results from OVCAR and SKOV3 cells treated with 50 μM tri_i capture agent. Each cell line shows a significant decrease in viability after 1 day treatment.
Figure 35B:
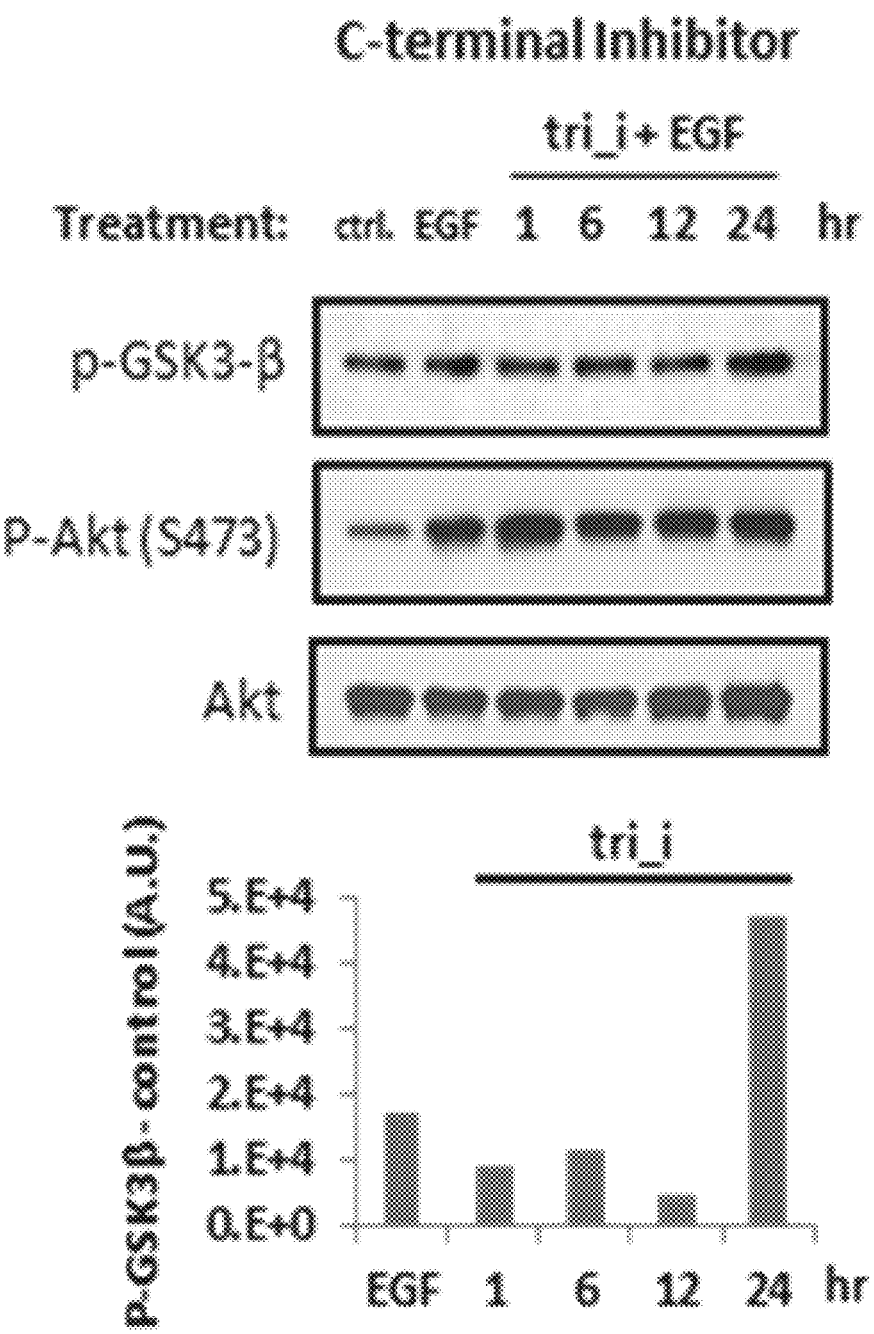

Similarly, the TAT-modified tri_i inhibits both phosphorylation of GSK3-β and cancer cell viability (FIG. 35). SKOV3 cells were pretreated with 50 μM tri_i for various times, before being simultaneously stimulated with EGF for 10 minutes and lysed (FIG. 35b). Stimulation of all cells with EGF to increase phosphorylation of GSK3-β provides a more stringent control for assessing the efficacy of the tri_i inhibitor. Cells pretreated with tri_i for 1, 6 and 12 hours and then stimulated with EGF show less phospho-GSK3-β than untreated cells stimulated with EGF alone. Cells treated for 24 hours with tri_i, however, show a dramatic increase in levels of phospho-GSK3-β. This remains consistent with our findings that a feedback mechanism may eventually be triggered by PCC treatment. Similar to tri_a, tri_i inhibition of Akt appears to be independent of Akt phosphorylation at Ser473.

Figure 35C:
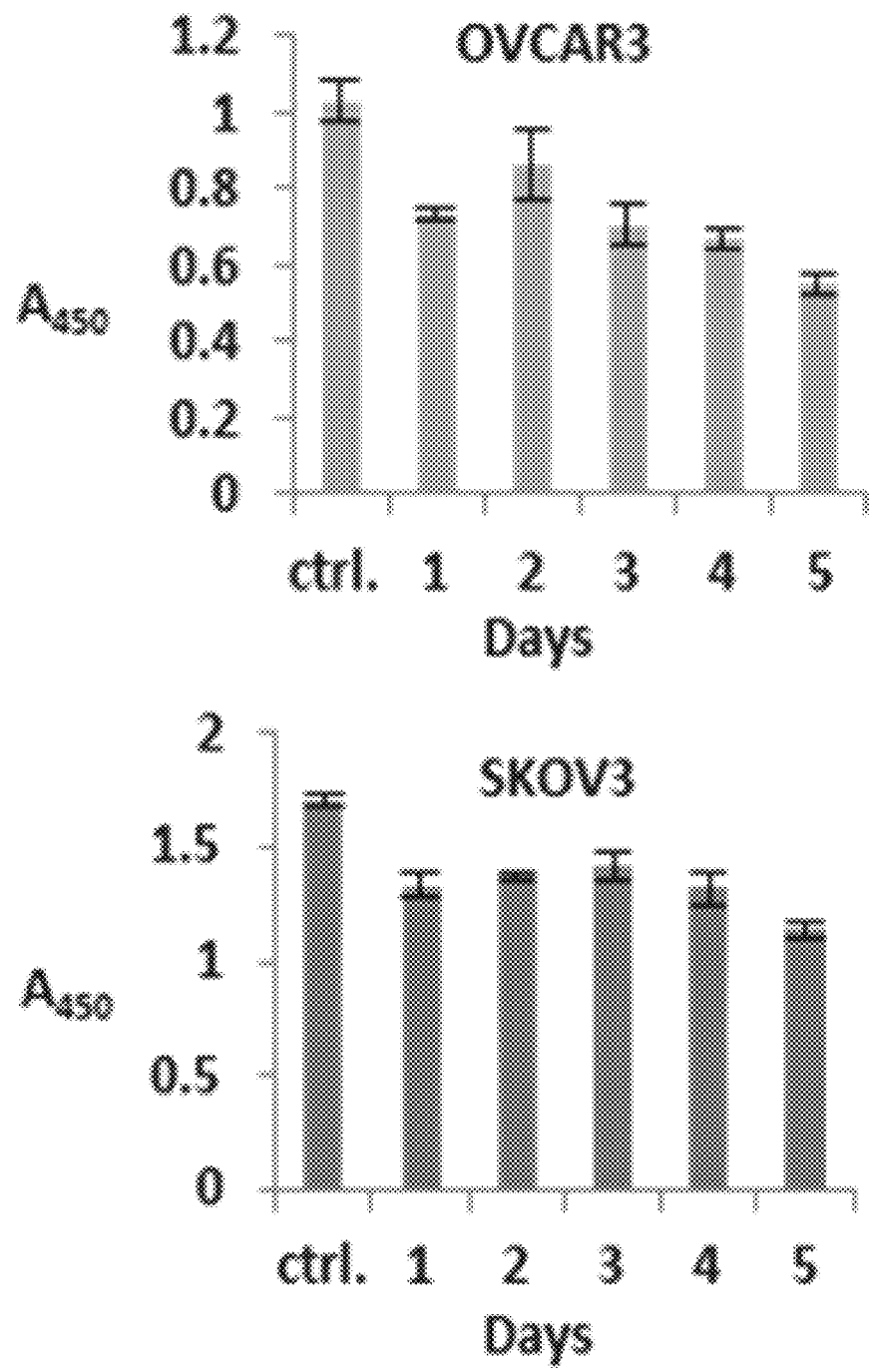

Additionally, tri_i also inhibits cell proliferation. XTT data shows an initial drop in cell viability after 24 hours, followed by an increase before finally decreasing again. SKOV3 cells show an initial drop in cell viability and remain consistently lower than untreated cells for 5 days (FIG. 35c). The results from the XTT assays are consistent with the expected phenotypic outcome of Akt inhibition.

In addition to controlling Akt enzymatic activity with PCC agents, chemical functionality can be encoded into these molecules. For instance, the orthogonally-protected lysine residue in the linker region was the site of fluorescein incorporation for imaging studies. The linker region can also serve as a programmable module in which one can potentially encode any cellular signal. Cells utilize chemical signals to catalyze many processes that are necessary for life.

Another example of using cellular signals to control proteins is the recent development of proteolysis targeting chimeric molecules, or protacs. Protacs utilize the quality-control machinery of the cell by artificially targeting proteins for proteasomal degradation. The tri_a and tri_i PCC agents were turned into protacs by encoding a peptide ligand for the E3 ubiquitin ligase von Hippel Lindau protein, VHL. This was accomplished by encoding the VHL binding site from hypoxia-inducible factor 1-alpha (Hif-1α) protein onto the capture agents. It is hypothesized that capture agent-induced recruitment of VHL to Akt could result in ubiquitination and proteasomal degradation of Akt.

Figure 36A:
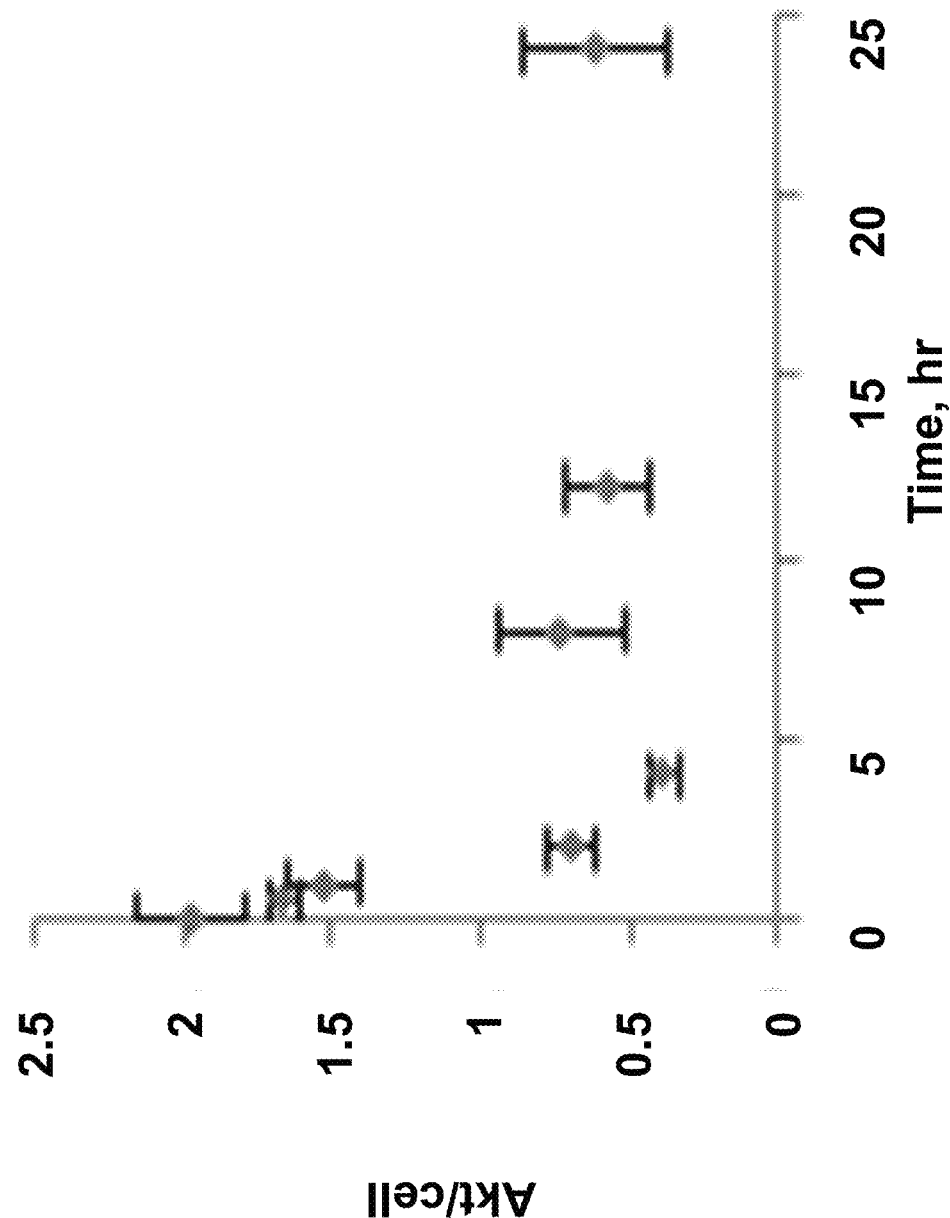
FIG. 36: (a) In-cell ELISA measurement of Akt in OVCAR3 cells treated tri_a functionalized with the degradation-inducing Hif-1α sequence for various times. (B) In-cell ELISA measurement of Akt in OVCAR3 cells after treatment with 100 μM tri_i-protac for various times. (C) In-cell ELISA measurement of Akt after 4 hour treatment with tri_a-protac at various doses. Results show dose-dependent degradation of Akt with an EC50 value of 128±19 µM.
Figure 36C:
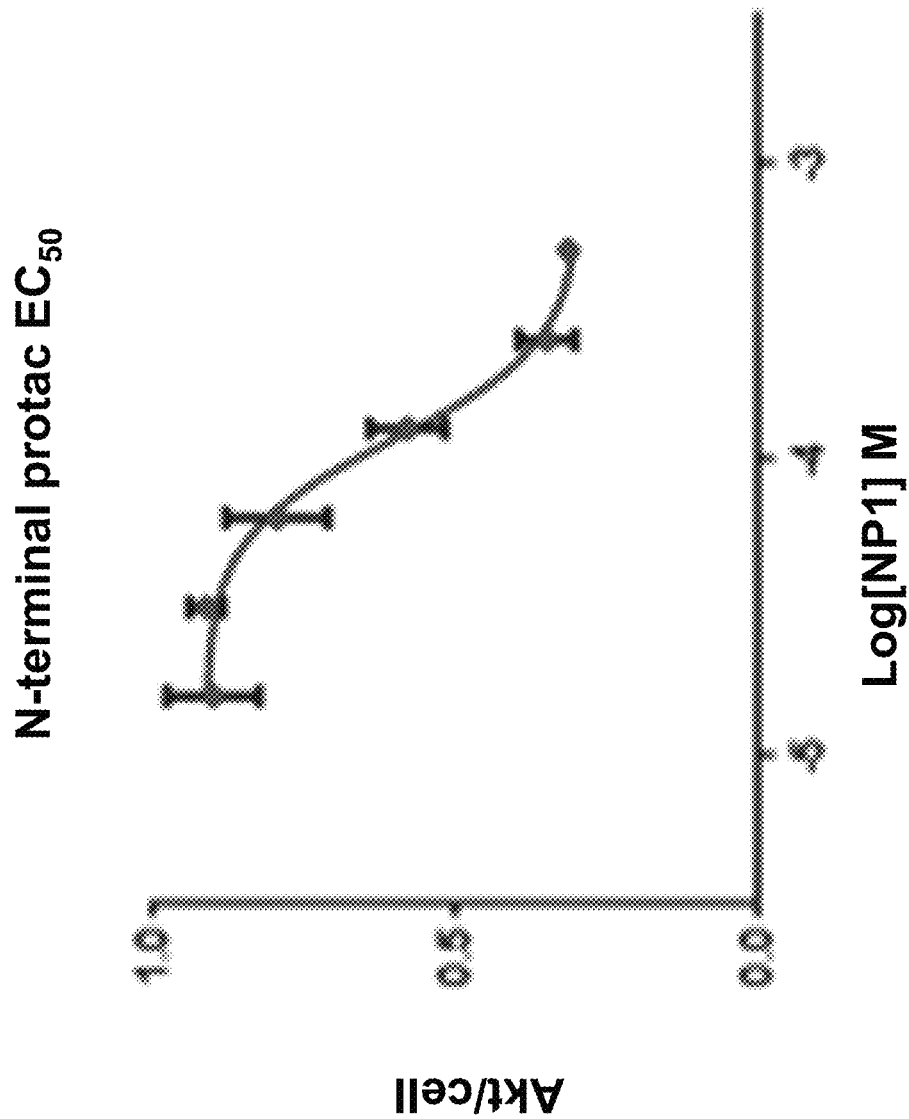

Both activating and inhibiting capture agents were able to induce Akt degradation when functionalized with the Hif-1α sequence (FIG. 36). OVCAR3 cells were treated with tri_a-protac over 24 hours and Akt was seen to decrease after 30 minutes, reaching a nadir after 4 hours (FIG. 36a). Similarly, tri_i-protac also reduced the amount of Akt per cell over time with a nadir reached after 8 hours (FIG. 36b). A dose-dependent decrease in Akt upon treatment with the tri_i-protac was also observed, which has an EC50 of 128±19 μM (FIG. 36c). Previous protacs were developed by adding a degradation signal to a modified protein ligand or previously discovered inhibitors. Here both an activator and an inhibitor were turned into successful protacs, indicating that ubiquitination and degradation can be induced regardless of the activation state of the target protein.

What is claimed is:

1. A capture agent, wherein the capture agent comprises an anchor ligand, a secondary ligand, and a tertiary ligand, wherein the capture ligand binds to residues 450-481 of phosphorylated Akt2, wherein the anchor ligand comprises an amino acid sequence wkvk (SEQ ID NO:1) or wkvkl (SEQ ID NO:2), wherein the anchor ligand, the secondary ligand, and the tertiary ligand each bind to Akt2, wherein the secondary ligand is identified by contacting an anchor ligand selection block and a plurality of first candidate peptides with Akt2, wherein (a) the anchor ligand selection block comprises the anchor ligand and an azido group and the first candidate peptides each comprise a peptide and an alkynyl group or (b) the anchor ligand selection block comprises the anchor ligand and an alkynyl group and the first candidate peptides each comprise a peptide and an azido group, whereby a biligand is formed by a disubstituted 1,2,3-triazole linkage being formed between the anchor ligand selection block and one of the first candidate peptides by the azido group or alkynyl group of the anchor ligand selection block and the alkynyl group or azido group of the one of the first candidate peptides being brought in close proximity by binding to the Akt2, wherein the candidate peptide with which the triazole linkage is formed with the anchor ligand selection block is identified as the secondary ligand of the capture agent, wherein the peptides of the first candidate peptides comprise 5 to 7 amino acid residues, wherein the amino acid residues are independently selected from the non-natural (D) sterioisomers of the 20 natural amino acids, excluding cysteine and methionine, wherein the tertiary ligand is identified by contacting a biligand selection block and a plurality of second candidate peptides with Akt2, wherein (a) the biligand selection block comprises the biligand and an azido group and the second candidate peptides each comprise a peptide and an alkynyl group or (b) the biligand selection block comprises the biligand and an alkynyl group and the second candidate peptides each comprise a peptide and an azido group, whereby a triligand is formed by a disubstituted 1,2,3-triazole linkage being formed between the biligand selection block and one of the second candidate peptides by the azido group or alkynyl group of the biligand selection block and the alkynyl group or azido group of the one of the second candidate peptides being brought in close proximity by binding to the Akt2, wherein the candidate peptide with which the triazole linkage is formed with the biligand selection block is identified as the tertiary ligand of the capture agent, wherein the peptides of the second candidate peptides comprise 5 to 7 amino acid residues, wherein the amino acid residues are independently selected from the non-natural (D) sterioisomers of the 20 natural amino acids, excluding cysteine and methionine.

2. The capture agent of claim 1, wherein the anchor ligand comprises an amino acid sequence wkvk (SEQ ID NO:1).

3. The capture agent of claim 1, wherein the secondary ligand comprises the amino acid sequence selected from hnGxx (SEQ ID NO:5), hnGii-(D-Pra) (SEQ ID NO:35), hnGre-(D-Pra) (SEQ ID NO:37), hrytG-(D-Pra) (SEQ ID NO:38), vnrrf-(D-Pra) (SEQ ID NO:39), hnGGd-(D-Pra) (SEQ ID NO:36), ayphf-(D-Pra) (SEQ ID NO:40), Gfrrf-(D-Pra) (SEQ ID NO:41), rGffl-(D-Pra) (SEQ ID NO:42), hnGyG-(D-Pra) (SEQ ID NO:22), vyyrh-(D-Pra) (SEQ ID NO:43), hnGai-(D-Pra) (SEQ ID NO:24), fhyyy-(D-Pra) (SEQ ID NO:44), fyhkh-(D-Pra) (SEQ ID NO:45), pfqhf-(D-Pra) (SEQ ID NO:46), shfyt-(D-Pra) (SEQ ID NO:47), vhGaa-(D-Pra) (SEQ ID NO:48), yhqyG-(D-Pra) (SEQ ID NO:49), wherein each x is independently selected from non-natural (D) stereoisomers of the 20 natural amino acids, excluding cysteine and methionine.

4. The capture agent of claim 3, wherein the secondary ligand comprises the amino acid sequence hnGxx (SEQ ID NO:5).

5. The capture agent of claim 4, wherein the secondary ligand comprises an amino acid sequence selected from the group consisting of hnGyG (SEQ ID NO:6), hnGyf (SEQ ID NO:7), hnGre (SEQ ID NO:8) and hnGai (SEQ ID NO:9).

6. The capture agent of claim 5, wherein the secondary ligand comprises an amino acid sequence of hnGyf (SEQ ID NO:7).

7. The capture agent of claim 1, wherein the tertiary ligand comprises the amino acid sequence hdGxx (SEQ ID NO:10), wherein each x is independently selected from non-natural (D) stereoisomers of the 20 natural amino acids, excluding cysteine and methionine.

8. The capture agent of claim 1, wherein the tertiary ligand comprises an amino acid sequence selected from hdGGf (SEQ ID NO:79), yyrfG (SEQ ID NO:11) and ssGry (SEQ ID NO:12).

9. The capture agent of claim 1, wherein the anchor ligand and secondary ligand are linked together via a 1,4-substituted-1,2,3-triazole residue (Tz4) or via a 1,5-substituted-1,2,3-triazole residue (Tz5).

10. The capture agent of claim 1, wherein the tertiary ligand is covalently bound to the secondary ligand.

11. The capture agent of claim 1, wherein the tertiary ligand is covalently bound to the anchor ligand.

12. The capture agent of claim 1, wherein the capture agent is labeled with a label selected from the group consisting of biotin, copper-DOTA, biotin-PEG3, aminooxyacetate, $^{19}$FB, $^{18}$FB, 5-Carboxyfluorescein, and FITC-PEG3.

13. The capture agent of claim 1, wherein the capture agent is labeled with the detectable moiety consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc $^{110m}$In, $^{11}$C and $^{76}$Br.

14. The capture agent of claim 1, wherein the capture agent further comprises a cell penetrating peptide.

15. The capture agent of claim 14, wherein the cell penetrating peptide is HIV-TAT.

16. A capture agent having the structure:

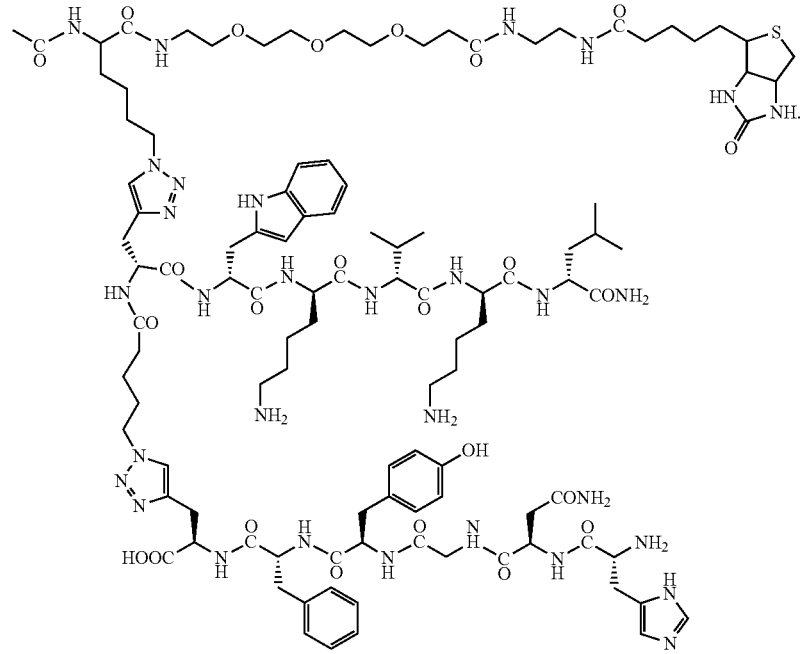

17. A capture agent having the structure:
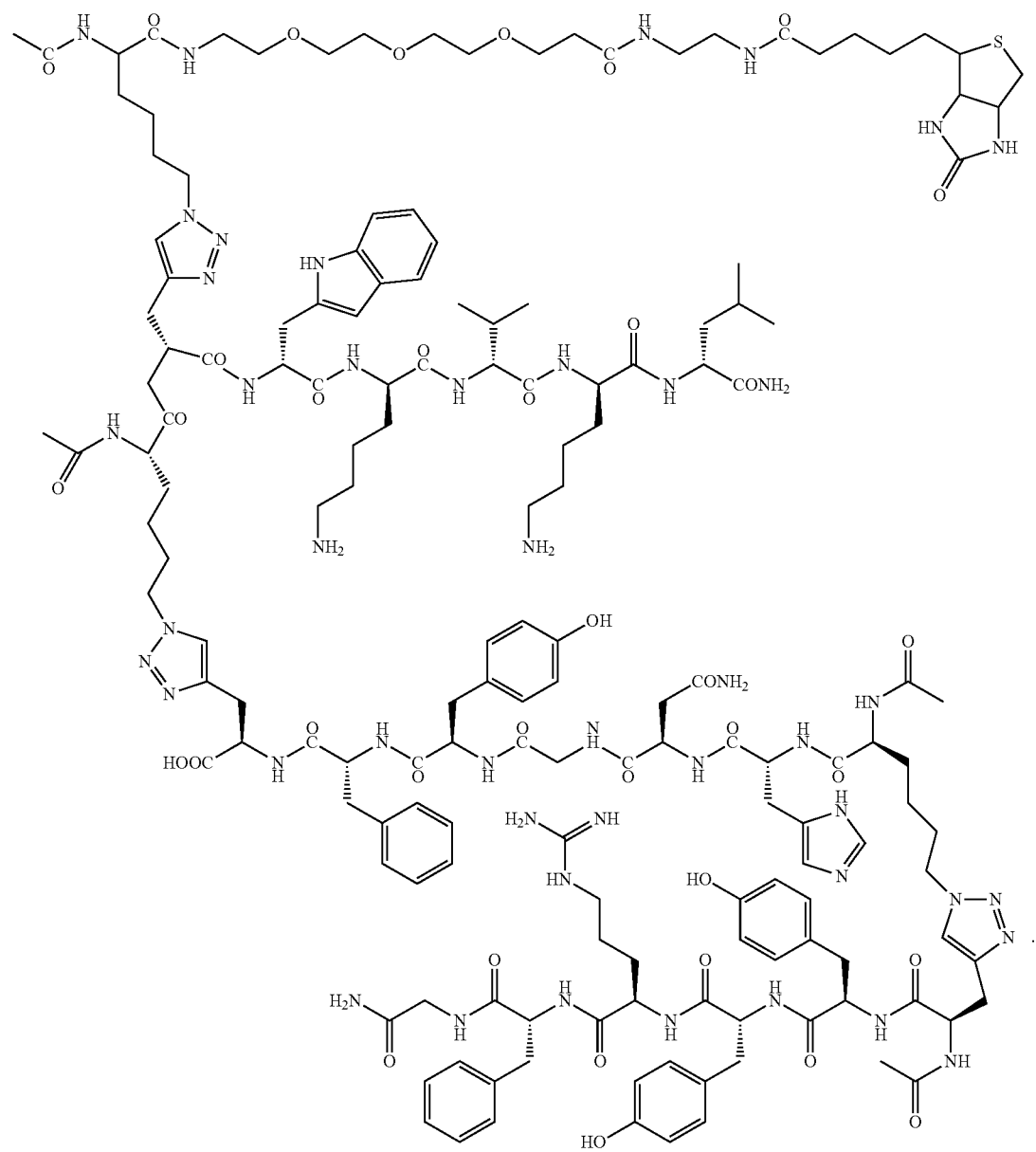

18. A capture agent having the structure:

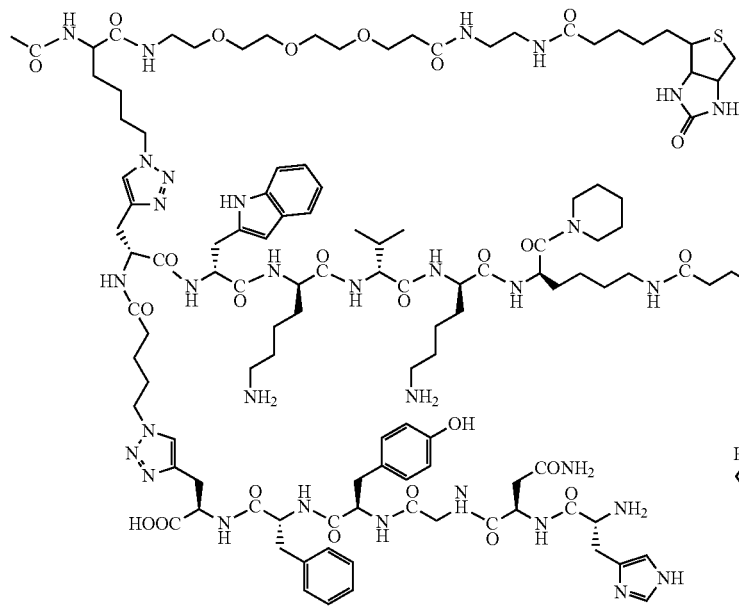
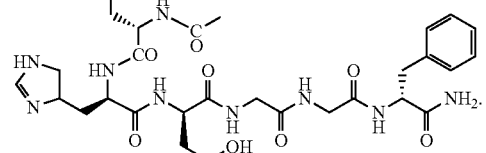

19. A composition comprising two or more capture agents of claim 1.

20. A method for detecting phosphorylated Akt2 in a biological sample, comprising the step of contacting the biological sample with one or more capture agents of claim 1.

21. A method for detecting phosphorylated Akt2 in a biological sample, comprising the step of contacting the biological sample with one or more capture agents of claim 12.

22. A method for detecting phosphorylated Akt2 in a biological sample using an immunoassay, wherein the immunoassay utilizes a capture agent of claim 1.

23. A method of diagnosing a cancer associated with increased Akt2 expression in a subject, the method comprising the steps of:
 a) contacting a biological sample from the subject with one or more capture agents of claim 1, wherein each capture agent is linked to a detectable moiety;
 b) binding antibody in the biological sample to a substrate; and
 c) detecting the moiety linked to the capture agent on the substrate;
 wherein detection of the moiety on the substrate diagnoses cancer associated with increased Akt2 expression in the subject.

24. The method of claim 23, wherein the capture agent is also linked to a cell penetrating peptide.

25. The method of claim 24, wherein the cell penetrating peptide is HIV-TAT.

26. A method of monitoring treatment of a cancer associated with increased Akt2 expression in a subject, comprising the steps of:
 a) contacting a first biological sample from the subject with one or more capture agents of claim 1, wherein each capture agent is linked to a detectable moiety;
 b) detecting the moiety linked to the capture agent, wherein the capture agent is bound to Akt2;
 c) administering a treatment for the cancer associated with increased Akt2 expression to the subject;
 d) contacting a second biological sample from the subject one or more capture agents of claim 1, wherein each capture agent is linked to a detectable moiety; and
 e) detecting the moiety linked to the capture agent, wherein the capture agent is bound to Akt2;
 (f) comparing the level of moiety detected in step (b) with the level of moiety detected in step (d);
 wherein, if less of the moiety is detected in step (e) than in step (b), the treatment is improving cancer in the subject.

27. The method of claim 26, wherein the capture agent is also linked to a cell penetrating peptide.

28. The method of claim 27, wherein the cell penetrating peptide is HIV-TAT.

29. A method of detecting Akt2 in a biological sample, comprising the steps of:
 a) contacting the sample with a capture agent of claim 1, wherein the capture agent is linked to a detectable moiety; and
 b) detecting the moiety linked to the capture agent, wherein the capture agent is bound to Akt2; and
 wherein detection of the moiety indicates the presence of Akt2 in the subject.

30. The method of claim 29, wherein the capture agent is also linked to a cell penetrating peptide.

31. The method of claim 30, wherein the cell penetrating peptide is HIV-TAT.

32. A multiplex capture agent comprising two or more capture agents of claim 1, wherein the multiplex capture agent specifically binds Akt2.

33. The capture agent of claim 1, further comprising a tag that encodes a cellular signal to control an Akt protein.

34. The capture agent of claim 33, wherein the tag targets the Akt protein for proteosomal degradation.

35. The capture agent of claim 34, wherein the tag targets the Akt protein for ubiquitination.

36. The capture agent of claim 35, wherein the capture agent is a proteolysis targeting chimeric molecule (protac).

37. The capture agent of claim 35, wherein the Akt protein is Akt2.

38. The capture agent of claim 36, wherein the tag is the Hif-1α degradation peptide ALAPYIP (SEQ ID NO:27).

39. A method of treating a cancer associated with increased Akt2 expression and/or activity in a subject in need thereof, comprising administering a therapeutically effective amount of a capture agent of claim 1.

40. The method of claim 39, wherein the capture agent is also linked to a cell penetrating peptide.

41. The method of claim 40, wherein the cell penetrating peptide is HIV-TAT.

42. A method of inhibiting Akt2 activity in a subject comprising administering to the subject a capture agent of claim 1.

43. The method of claim 42, wherein the capture agent is also linked to a cell penetrating peptide.

44. The method of claim 43, wherein the cell penetrating peptide is HIV-TAT.

45. A method of imaging a cancer associated with increased Akt2 expression and/or activity in a subject in need thereof, comprising administering an effective amount of a capture agent of claim 1.

46. The method of claim 45, wherein the capture agent is also linked to a cell penetrating peptide.

47. The method of claim 46, wherein the cell penetrating peptide is HIV-TAT.

48. The capture agent of claim 1, wherein the anchor ligand comprises an amino acid sequence wkvkl (SEQ ID NO:2).

49. The capture agent of claim 1, wherein the tertiary ligand comprises an amino acid sequence selected from hdGxx (SEQ ID NO:10), (D-Pra)-[k/l]fqfr (SEQ ID NO:50), (D-Pra)-r[d/n]rfr (SEQ ID NO:51), (D-Pra)-yvyrf (SEQ ID NO:52), (D-Pra)-ssGry (SEQ ID NO:14), (D-Pra)-yyrfg (SEQ ID NO:13), (D-Pra)-sfrrf (SEQ ID NO:53), (D-Pra)-svrfr (SEQ ID NO:54), (D-Pra)-i[k/l]rra (SEQ ID NO:55), (D-Pra)-r[q/t][k/l]wr (SEQ ID NO:56), (D-Pra)-r[q/t]srr (SEQ ID NO:57), (D-Pra)-rriyy (SEQ ID NO:58), (D-Pra)-rfGr[q/t] (SEQ ID NO:59), (L-Az4)-hdGsq (SEQ ID NO:66), (L-Az4)-hdGww (SEQ ID NO:67), (L-Az4)-hdGiv (SEQ ID NO:68), (L-Az4)-hdGdw (SEQ ID NO:69), (L-Az4)-hdGG (SEQ ID NO:70), (L-Az4)-hdGdr (SEQ ID NO:71), (L-Az4)-hdGGf (SEQ ID NO:72), (L-Az4)-hdGGe (SEQ ID NO:73), (L-Az4)-hdGsf (SEQ ID NO:74), (L-Az4)-hdGqk (SEQ ID NO:75), (L-Az4)-hdGsa (SEQ ID NO:76), (L-Az4)-hdGkf (SEQ ID NO:77), and (L-Az4)-rleav (SEQ ID NO:78), wherein each x is independently selected from non-natural (D) stereoisomers of the 20 natural amino acids, excluding cysteine and methionine.

50. A capture agent, wherein the capture agent comprises an anchor ligand, a secondary ligand, and a tertiary ligand, wherein the capture ligand binds to residues 450-481 of phosphorylated Akt2,
 wherein the anchor ligand comprises an amino acid sequence wkvk (SEQ ID NO:1) or wkvkl (SEQ ID NO:2),
 wherein the secondary ligand comprises the amino acid sequence selected from hnGxx (SEQ ID NO:5), hnGii-(D-Pra) (SEQ ID NO:35), hnGre-(D-Pra) (SEQ ID NO:37), hrytG-(D-Pra) (SEQ ID NO:38), vnrrf-(D-Pra) (SEQ ID NO:39), hnGGd-(D-Pra) (SEQ ID NO:36), ayphf-(D-Pra) (SEQ ID NO:40), Gfrrf-(D-Pra) (SEQ ID NO:41), rGffl-(D-Pra) (SEQ ID NO:42), hnGyG-(D-Pra) (SEQ ID NO:22), vyyrh-(D-Pra) (SEQ ID NO:43), hnGai-(D-Pra) (SEQ ID NO:24), fhyyy-(D-Pra) (SEQ ID NO:44), fyhkh-(D-Pra) (SEQ ID NO:45), pfqhf-(D-Pra) (SEQ ID NO:46), shfyt-(D-Pra) (SEQ ID NO:47), vhGaa-(D-Pra) (SEQ ID NO:48), and yhqyG-(D-Pra) (SEQ ID NO:49), wherein each x is independently selected from non-natural (D) stereoisomers of the 20 natural amino acids, excluding cysteine and methionine,
 wherein the tertiary ligand comprises an amino acid sequence selected from hdGxx (SEQ ID NO:10), (D-Pra)-[k/l]fqfr (SEQ ID NO:50), (D-Pra)-r[d/n]rfr (SEQ ID NO:51), (D-Pra)-yvyrf (SEQ ID NO:52), (D-Pra)-ssGry (SEQ ID NO:14), (D-Pra)-yyrfg (SEQ ID NO:13), (D-Pra)-sfrrf (SEQ ID NO:53), (D-Pra)-svrfr (SEQ ID NO:54), (D-Pra)-i[k/l]rra (SEQ ID NO:55), (D-Pra)-r[q/t][k/l]wr (SEQ ID NO:56), (D-Pra)-r[q/t]srr (SEQ ID NO:57), (D-Pra)-rriyy (SEQ ID NO:58), (D-Pra)-rfGr[q/t] (SEQ ID NO:59), (L-Az4)-hdGsq (SEQ ID NO:66), (L-Az4)-hdGww (SEQ ID NO:67), (L-Az4)-hdGiv (SEQ ID NO:68), (L-Az4)-hdGdw (SEQ ID NO:69), (L-Az4)-hdGG (SEQ ID NO:70), (L-Az4)-hdGdr (SEQ ID NO:71), (L-Az4)-hdGGf (SEQ ID NO:72), (L-Az4)-hdGGe (SEQ ID NO:73), (L-Az4)-hdGsf (SEQ ID NO:74), (L-Az4)-hdGqk (SEQ ID NO:75), (L-Az4)-hdGsa (SEQ ID NO:76), (L-Az4)-hdGkf (SEQ ID NO:77), and (L-Az4)-rleav (SEQ ID NO:78), wherein each x is independently selected from non-natural (D) stereoisomers of the 20 natural amino acids, excluding cysteine and methionine.

51. A capture agent, wherein the capture agent comprises an anchor ligand, a secondary ligand, and a tertiary ligand, wherein the capture ligand binds to residues 450-481 of phosphorylated Akt2,
 wherein the secondary ligand comprises the amino acid sequence selected from hnGxx (SEQ ID NO:5), hnGii-(D-Pra) (SEQ ID NO:35), hnGre-(D-Pra) (SEQ ID NO:37), hrytG-(D-Pra) (SEQ ID NO:38), vnrrf-(D-Pra) (SEQ ID NO:39), hnGGd-(D-Pra) (SEQ ID NO:36), ayphf-(D-Pra) (SEQ ID NO:40), Gfrrf-(D-Pra) (SEQ ID NO:41), rGffl-(D-Pra) (SEQ ID NO:42), hnGyG-(D-Pra) (SEQ ID NO:22), vyyrh-(D-Pra) (SEQ ID NO:43), hnGai-(D-Pra) (SEQ ID NO:24), fhyyy-(D-Pra) (SEQ ID NO:44), fyhkh-(D-Pra) (SEQ ID NO:45), pfqhf-(D-Pra) (SEQ ID NO:46), shfyt-(D-Pra) (SEQ ID NO:47), vhGaa-(D-Pra) (SEQ ID NO:48), and yhqyG-(D-Pra) (SEQ ID NO:49), wherein each x is independently selected from non-natural (D) stereoisomers of the 20 natural amino acids, excluding cysteine and methionine.

52. The capture agent of claim 51, wherein the tertiary ligand comprises an amino acid sequence selected from hdGxx (SEQ ID NO:10), (D-Pra)-[k/l]fqfr (SEQ ID NO:50), (D-Pra)-r[d/n]rfr (SEQ ID NO:51), (D-Pra)-yvyrf (SEQ ID NO:52), (D-Pra)-ssGry (SEQ ID NO:14), (D-Pra)-yyrfg (SEQ ID NO:13), (D-Pra)-sfrrf (SEQ ID NO:53), (D-Pra)-svrfr (SEQ ID NO:54), (D-Pra)-i[k/l]rra (SEQ ID NO:55), (D-Pra)-r[q/t][k/l]wr (SEQ ID NO:56), (D-Pra)-r[q/t]srr (SEQ ID NO:57), (D-Pra)-rriyy (SEQ ID NO:58), (D-Pra)-rfGr[q/t] (SEQ ID NO:59), (L-Az4)-hdGsq (SEQ ID NO:66), (L-Az4)-hdGww (SEQ ID NO:67), (L-Az4)-hdGiv (SEQ ID NO:68), (L-Az4)-hdGdw (SEQ ID NO:69), (L-Az4)-hdGG (SEQ ID NO:70), (L-Az4)-hdGdr (SEQ ID NO:71), (L-Az4)-hdGGf (SEQ ID NO:72), (L-Az4)-hdGGe (SEQ ID NO:73), (L-Az4)-hdGsf (SEQ ID NO:74), (L-Az4)-hdGqk (SEQ ID NO:75), (L-Az4)-hdGsa (SEQ ID NO:76), (L-Az4)-hdGkf (SEQ ID NO:77), and (L-Az4)- rleav (SEQ ID NO:78), wherein each x is independently selected from non-natural (D) stereoisomers of the 20 natural amino acids, excluding cysteine and methionine.

53. A capture agent, wherein the capture agent comprises an anchor ligand, a secondary ligand, and a tertiary ligand, wherein the capture ligand binds to residues 450-481 of phosphorylated Akt2,
wherein the tertiary ligand comprises an amino acid sequence selected from hdGxx (SEQ ID NO:10), (D-Pra)-[k/l]fqfr (SEQ ID NO:50), (D-Pra)-r[d/n]rfr (SEQ ID NO:51), (D-Pra)-yvyrf (SEQ ID NO:52), (D-Pra)-ssGry (SEQ ID NO:14), (D-Pra)-yyrfg (SEQ ID NO:13), (D-Pra)-sfrrf (SEQ ID NO:53), (D-Pra)-svrfr (SEQ ID NO:54), (D-Pra)-i[k/l]rra (SEQ ID NO:55), (D-Pra)-r[q/t][k/l]wr (SEQ ID NO:56), (D-Pra)-r[q/t]srr (SEQ ID NO:57), (D-Pra)-rriyy (SEQ ID NO:58), (D-Pra)-rfGr[q/t] (SEQ ID NO:59), (L-Az4)-hdGsq (SEQ ID NO:66), (L-Az4)-hdGww (SEQ ID NO:67), (L-Az4)-hdGiv (SEQ ID NO:68), (L-Az4)-hdGdw (SEQ ID NO:69), (L-Az4)-hdGG (SEQ ID NO:70), (L-Az4)-hdGdr (SEQ ID NO:71), (L-Az4)-hdGGf (SEQ ID NO:72), (L-Az4)-hdGGe (SEQ ID NO:73), (L-Az4)-hdGsf (SEQ ID NO:74), (L-Az4)-hdGqk (SEQ ID NO:75), (L-Az4)-hdGsa (SEQ ID NO:76), (L-Az4)-hdGkf (SEQ ID NO:77), and (L-Az4)-rleav (SEQ ID NO:78), wherein each x is independently selected from non-natural (D) stereoisomers of the 20 natural amino acids, excluding cysteine and methionine.

54. A capture agent, wherein the capture agent comprises an anchor ligand, a secondary ligand, and a tertiary ligand, wherein the capture ligand binds to residues 450-481 of phosphorylated Akt2, wherein the anchor ligand comprises an amino acid sequence wkvk (SEQ ID NO:1) or wkvkl (SEQ ID NO:2), wherein the secondary ligand comprises an amino acid sequence selected from the group consisting of hnGyG (SEQ ID NO:6), hnGyf (SEQ ID NO:7), hnGre (SEQ ID NO:8) and hnGai (SEQ ID NO:9), wherein the tertiary ligand comprises an amino acid sequence selected from hdGGf (SEQ ID NO:79), yyrfG (SEQ ID NO:11) and ssGry (SEQ ID NO:12),
wherein the anchor ligand, the secondary ligand, and the tertiary ligand each bind to Akt2.

55. A capture agent, wherein the capture agent comprises an anchor ligand, a secondary ligand, and a tertiary ligand, wherein the capture ligand binds to residues 450-481 of phosphorylated Akt2, wherein the anchor ligand comprises an amino acid sequence wkvk (SEQ ID NO:1) or wkvkl (SEQ ID NO:2),
wherein the anchor ligand, the secondary ligand, and the tertiary ligand each bind to Akt2,
wherein the secondary ligand is identified by contacting an anchor ligand selection block and a plurality of first candidate peptides with Akt2, wherein (a) the anchor ligand selection block comprises the anchor ligand and an azido group and the first candidate peptides each comprise a peptide and an alkynyl group or (b) the anchor ligand selection block comprises the anchor ligand and an alkynyl group and the first candidate peptides each comprise a peptide and an azido group, whereby a biligand is formed by a disubstituted 1,2,3-triazole linkage being formed between the anchor ligand selection block and one of the first candidate peptides by the azido group or alkynyl group of the anchor ligand selection block and the alkynyl group or azido group of the one of the first candidate peptides being brought in close proximity by binding to the Akt2, wherein the candidate peptide with which the triazole linkage is formed with the anchor ligand selection block is identified as the secondary ligand of the capture agent,
wherein the tertiary ligand is identified by contacting a biligand selection block and a plurality of second candidate peptides with Akt2, wherein (a) the biligand selection block comprises the biligand and an azido group and the second candidate peptides each comprise a peptide and an alkynyl group or (b) the biligand selection block comprises the biligand and an alkynyl group and the second candidate peptides each comprise a peptide and an azido group, whereby a triligand is formed by a disubstituted 1,2,3-triazole linkage being formed between the biligand selection block and one of the second candidate peptides by the azido group or alkynyl group of the biligand selection block and the alkynyl group or azido group of the one of the second candidate peptides being brought in close proximity by binding to the Akt2, wherein the candidate peptide with which the triazole linkage is formed with the biligand selection block is identified as the tertiary ligand of the capture agent.

* * * * *

UNITED STATES PATENT AND TRADEMARK OFFICE
CERTIFICATE OF CORRECTION

| | | |
|---|---|---|
| PATENT NO. | : 11,371,994 B2 | Page 1 of 1 |
| APPLICATION NO. | : 14/485243 | |
| DATED | : June 28, 2022 | |
| INVENTOR(S) | : James R. Heath et al. | |

It is certified that error appears in the above-identified patent and that said Letters Patent is hereby corrected as shown below:

In the Specification

Column 1, Lines 13-16, replace the paragraph:
"This invention was made with government support Grant No. CA119347 awarded by the National Institutes of Health and Grant No. W911NF-09-D-001 awarded by the U.S. Amy. The government has certain rights in the invention." with "This invention was made with government support under Grant No. CA119347 awarded by the National Institutes of Health and under Grant No. W911NF-09-D-0001 awarded by the U.S. Army. The government has certain rights in the invention."

Signed and Sealed this
Second Day of May, 2023

Katherine Kelly Vidal
*Director of the United States Patent and Trademark Office*